US011511069B2

(12) United States Patent
Jackson et al.

(10) Patent No.: US 11,511,069 B2
(45) Date of Patent: Nov. 29, 2022

(54) HUMIDIFICATION SYSTEM

(71) Applicant: Fisher & Paykel Healthcare Limited, Auckland (NZ)

(72) Inventors: John James Jackson, Auckland (NZ); Barry Shack Manon, Auckland (NZ); Victor Rosales Corrales, Auckland (NZ); Stefan Leo Van Workum, Auckland (NZ); Michael John Andresen, Auckland (NZ); Stephen David Evans, Auckland (NZ); Mark Samuel Hamilton, Auckland (NZ); Paul Fleming Buckley, Auckland (NZ); Jason Allan Klenner, Auckland (NZ); Hamish Osborne, Auckland (NZ); Samuel Graham Boggs, Auckland (NZ); James William Stanton, Auckland (NZ); Joseph Nathaniel Griffiths, Auckland (NZ); Jonathan Andrew George Lambert, Auckland (NZ); Nicholas Edward Vaughan, Auckland (NZ); James Owen Kehoe, Auckland (NZ); Francisco Ernesto De La Peña De La Fuente, Auckland (NZ); Nicholas James Michael McKenna, Auckland (NZ); Rachael Porter, Auckland (NZ); Simon Mordechai Stam, Auckland (NZ); David Robert Kemps, Auckland (NZ); Edwin Joseph Lyons, Auckland (NZ); Madeleine Bess Martin, Auckland (NZ); Ada Yiwen Shou, Auckland (NZ); Huang-Ku Liu, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 469 days.

(21) Appl. No.: 15/021,616

(22) PCT Filed: Sep. 15, 2014

(86) PCT No.: PCT/NZ2014/000202
§ 371 (c)(1),
(2) Date: Mar. 11, 2016

(87) PCT Pub. No.: WO2015/038014
PCT Pub. Date: Mar. 19, 2015

(65) Prior Publication Data
US 2016/0228671 A1    Aug. 11, 2016

Related U.S. Application Data

(60) Provisional application No. 62/032,462, filed on Aug. 1, 2014, provisional application No. 61/971,474, filed (Continued)

(51) Int. Cl.
*A61M 16/16* (2006.01)
*A61M 16/10* (2006.01)
(Continued)

(52) U.S. Cl.
CPC ...... *A61M 16/161* (2014.02); *A61M 16/0816* (2013.01); *A61M 16/0833* (2014.02); (Continued)

(58) Field of Classification Search
CPC .. A61M 11/04; A61M 11/041; A61M 11/042; A61M 11/044; A61M 16/10; (Continued)

(56) References Cited

U.S. PATENT DOCUMENTS 1,154,259 A    9/1915  Light
1,163,657 A *  12/1915 Hadaway ............. A61M 11/041
                                              261/104
(Continued)

FOREIGN PATENT DOCUMENTS

AU    2007317198    5/2008
AU    2010206053    2/2011
(Continued)

OTHER PUBLICATIONS

Dysart K et al. Research in high flow therapy: mechanisms of action. Respir Med. Oct. 2009;103(10):1400-5.*
(Continued)

*Primary Examiner* — Justine R Yu
*Assistant Examiner* — Matthew R Moon
(74) *Attorney, Agent, or Firm* — Knobbe, Martens, Olson & Bear, LLP

(57) ABSTRACT

A humidification system can include a heater base, a chamber, and a breathing circuit. The heater base includes a heater plate positioned in a recessed region, and a heat conductive portion of the chamber is configured to contact the heater plate. The heater base includes a guard configured to control movement of the chamber into and out of the recessed
(Continued)

region. The guard includes an anti-racking mechanism. The chamber includes an inlet port, an outlet port. A downward extension extends into the chamber from the inlet port, and a baffle is disposed at a lower end of the downward extension. A component of the breathing circuit can include a conduit hanging end cap for shipping and storage. The end cap can include a hanging component to allow the breathing circuit component to be hung from a medical stand. The system can detect when breathing circuits are connected in reverse.

29 Claims, 40 Drawing Sheets

Related U.S. Application Data on Mar. 27, 2014, provisional application No. 61/877,736, filed on Sep. 13, 2013, provisional application No. 61/877,622, filed on Sep. 13, 2013, provisional application No. 61/877,566, filed on Sep. 13, 2013.

(51) Int. Cl.
  *A61M 16/08* (2006.01)
  *A61M 16/00* (2006.01)

(52) U.S. Cl.
  CPC ...... *A61M 16/0875* (2013.01); *A61M 16/109* (2014.02); *A61M 16/1095* (2014.02); *A61M 16/16* (2013.01); *A61M 16/108* (2014.02); *A61M 16/1085* (2014.02); *A61M 16/168* (2014.02); *A61M 2016/0033* (2013.01); *A61M 2205/02* (2013.01); *A61M 2205/0216* (2013.01); *A61M 2205/123* (2013.01); *A61M 2205/14* (2013.01); *A61M 2205/17* (2013.01); *A61M 2205/18* (2013.01); *A61M 2205/21* (2013.01); *A61M 2205/3334* (2013.01); *A61M 2205/3368* (2013.01); *A61M 2205/502* (2013.01); *A61M 2205/6018* (2013.01); *A61M 2205/6027* (2013.01); *A61M 2205/6045* (2013.01); *A61M 2209/06* (2013.01); *A61M 2209/08* (2013.01)

(58) Field of Classification Search
  CPC .............. A61M 16/16; A61M 16/109; A61M 16/0066; A61M 16/1075–1085; A61M 16/161–168; A61M 2205/21; A61M 2205/36; A61M 2205/3653; H05B 2203/016; H05B 3/03
  USPC .......... 261/142; 219/385, 538–546; 126/113; 338/322
  See application file for complete search history.

(56) References Cited

U.S. PATENT DOCUMENTS

| | | | | |
|---|---|---|---|---|
| 2,448,388 | A * | 8/1948 | Percy | A47J 27/004 |
| | | | | 219/433 |
| 2,634,311 | A | 4/1953 | Darling | |
| 2,745,074 | A | 5/1956 | Darling | |
| 3,163,707 | A | 12/1964 | Darling | |
| 3,283,580 | A | 11/1966 | Jacob | |
| 3,394,954 | A | 7/1968 | Sarns | |
| 3,485,237 | A | 12/1969 | Bedford | |
| 3,582,094 | A | 6/1971 | Whittaker | |
| 3,588,859 | A | 6/1971 | Petree | |
| 3,638,926 | A | 2/1972 | Melville et al. | |
| 3,659,604 | A | 5/1972 | Melville et al. | |
| 3,703,892 | A | 11/1972 | Meyers | |
| 3,777,298 | A | 12/1973 | Newman | |
| 3,808,573 | A * | 4/1974 | Cappell | H05B 3/06 |
| | | | | 338/249 |
| 3,891,827 | A * | 6/1975 | Wyse | H05B 3/16 |
| | | | | 392/477 |
| 3,903,742 | A | 9/1975 | Colton | |
| 3,954,920 | A | 5/1976 | Heath | |
| 3,987,133 | A | 10/1976 | Andra | |
| 3,990,727 | A | 11/1976 | Gallagher | |
| 4,028,444 | A | 6/1977 | Brown et al. | |
| 4,038,519 | A | 7/1977 | Foucras | |
| 4,060,576 | A | 11/1977 | Grant | |
| 4,111,197 | A | 9/1978 | Warncke et al. | |
| 4,139,762 | A | 2/1979 | Pohrer et al. | |
| 4,172,709 | A | 10/1979 | Kippel et al. | |
| 4,183,248 | A | 1/1980 | West | |
| 4,311,900 | A * | 1/1982 | Hummel | H01C 3/18 |
| | | | | 219/530 |
| 4,333,451 | A | 6/1982 | Paluch | |
| 4,473,923 | A | 10/1984 | Neroni et al. | |
| 4,492,887 | A * | 1/1985 | Baldwin | H02K 9/197 |
| | | | | 310/68 R |
| 4,510,375 | A * | 4/1985 | Inskip | A47J 27/21016 |
| | | | | 219/437 |
| 4,529,867 | A | 7/1985 | Velnosky et al. | |
| 4,545,290 | A | 10/1985 | Lieberman | |
| 4,551,614 | A * | 11/1985 | Johnson | F24C 7/062 |
| | | | | 338/280 |
| 4,564,748 | A | 1/1986 | Gupton | |
| 4,588,425 | A | 5/1986 | Usry et al. | |
| 4,621,632 | A | 11/1986 | Bartels et al. | |
| 4,676,237 | A | 6/1987 | Wood et al. | |
| 4,686,354 | A | 8/1987 | Makin | |
| 4,708,831 | A | 11/1987 | Elsworth et al. | |
| 4,774,032 | A | 9/1988 | Coates et al. | |
| 4,778,017 | A * | 10/1988 | Liang | G01G 21/10 |
| | | | | 177/187 |
| 4,813,280 | A | 3/1989 | Miller, Jr. et al. | |
| 4,844,512 | A | 7/1989 | Gahwiler | |
| 4,942,877 | A | 7/1990 | Sakai et al. | |
| 4,944,310 | A | 7/1990 | Sullivan | |
| 4,967,744 | A | 11/1990 | Chua | |
| 5,031,612 | A | 7/1991 | Clementi | |
| 5,058,588 | A | 10/1991 | Kaestle | |
| 5,060,506 | A | 10/1991 | Douglas | |
| 5,117,819 | A | 6/1992 | Servidio et al. | |
| 5,134,996 | A | 8/1992 | Bell | |
| 5,148,801 | A | 9/1992 | Douwens et al. | |
| 5,213,376 | A | 5/1993 | Szabo | |
| 5,307,243 | A | 4/1994 | Sharp et al. | |
| RE34,599 | E | 5/1994 | Suszynski et al. | |
| 5,349,946 | A * | 9/1994 | McComb | A61M 16/1075 |
| | | | | 128/203.12 |
| 5,357,948 | A | 10/1994 | Eilentropp | |
| 5,359,179 | A * | 10/1994 | Desloge | H05B 3/58 |
| | | | | 219/535 |
| 5,367,604 | A | 11/1994 | Murray | |
| 5,392,770 | A | 2/1995 | Clawson et al. | |
| 5,454,061 | A | 9/1995 | Carlson | |
| 5,483,616 | A | 1/1996 | Chiu et al. | |
| 5,537,996 | A | 7/1996 | McPhee | |
| 5,551,883 | A | 9/1996 | Davis | |
| 5,640,951 | A | 6/1997 | Huddart et al. | |
| 5,660,567 | A | 8/1997 | Nierlich et al. | |
| 5,667,712 | A * | 9/1997 | Sutorius | B29C 45/1782 |
| | | | | 219/535 |
| 5,690,850 | A * | 11/1997 | Anderson | B29C 65/18 |
| | | | | 219/535 |
| 5,720,293 | A | 2/1998 | Quinn et al. | |
| 5,778,872 | A | 7/1998 | Fukunaga et al. | |
| 5,906,201 | A | 5/1999 | Nilson | |
| 5,926,922 | A * | 7/1999 | Stottle | B29C 45/1782 |
| | | | | 24/20 R |
| 5,943,473 | A | 8/1999 | Levine | |
| D419,522 | S | 1/2000 | Kamagai | |
| 6,039,696 | A | 3/2000 | Bell | |
| 6,053,482 | A | 4/2000 | Glenn et al. | |
| 6,078,729 | A | 6/2000 | Kopel | |
| 6,102,037 | A | 8/2000 | Koch | |

(56) References Cited

U.S. PATENT DOCUMENTS

| | | |
|---|---|---|
| 6,105,970 A | 8/2000 | Siegrist et al. |
| 6,126,610 A | 10/2000 | Rich et al. |
| 6,138,674 A | 10/2000 | Gull et al. |
| 6,196,980 B1 | 3/2001 | Akerfeldt et al. |
| 6,201,983 B1 | 3/2001 | Haumann et al. |
| 6,226,451 B1 | 5/2001 | Wong |
| 6,349,722 B1 | 2/2002 | Gradon et al. |
| 6,360,741 B2 | 3/2002 | Truschel |
| 6,402,207 B1 | 6/2002 | Segal et al. |
| 6,435,180 B1 | 8/2002 | Hewson et al. |
| 6,467,477 B1 | 10/2002 | Frank et al. |
| 6,508,249 B2 | 1/2003 | Hoenig |
| 6,511,075 B1 | 1/2003 | Schmidt |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,612,624 B1 | 9/2003 | Segal et al. |
| 6,648,669 B1 | 11/2003 | Kim et al. |
| 6,668,828 B1 | 12/2003 | Figley et al. |
| 6,685,491 B2 | 2/2004 | Gergek |
| 6,827,084 B2 | 12/2004 | Grubb, Jr. |
| 6,874,771 B2 | 4/2005 | Birdsell et al. |
| 6,895,803 B2 | 5/2005 | Seakins et al. |
| 6,918,389 B2 | 7/2005 | Seakins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,327,547 B1 | 2/2008 | Epstein |
| 7,327,949 B1 * | 2/2008 | Cheng ............... A61M 16/1075 128/203.12 |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,478,635 B2 | 1/2009 | Wixey et al. |
| 7,525,663 B2 | 4/2009 | Kwok et al. |
| 7,637,288 B2 | 12/2009 | Kressierer/Huber et al. |
| 7,677,246 B2 | 3/2010 | Kepler et al. |
| 7,766,050 B2 | 8/2010 | Patel |
| 7,794,426 B2 | 9/2010 | Briones et al. |
| 7,814,907 B2 | 10/2010 | Bremmer et al. |
| D628,288 S | 11/2010 | Row et al. |
| 7,827,981 B2 | 11/2010 | Bamford |
| 7,870,857 B2 | 1/2011 | Dhuper et al. |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,049,143 B2 * | 11/2011 | Andel ............... A61M 16/1075 128/203.12 |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,221,530 B2 | 7/2012 | Peter et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,469,025 B2 | 6/2013 | Mayer et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,528,552 B2 | 9/2013 | von Blumenthal |
| 8,544,465 B2 | 10/2013 | Smith et al. |
| 8,550,072 B2 | 10/2013 | Thudor et al. |
| 8,631,789 B2 | 1/2014 | Virr et al. |
| 8,640,696 B2 | 2/2014 | Pujol et al. |
| 8,733,348 B2 | 5/2014 | Korneff et al. |
| 8,733,349 B2 | 5/2014 | Bath et al. |
| 8,770,190 B2 | 7/2014 | Doherty et al. |
| 8,800,970 B2 | 8/2014 | Heine et al. |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,985,105 B2 | 3/2015 | Burton et al. |
| 9,022,946 B2 | 5/2015 | Haque |
| 9,067,036 B2 | 6/2015 | Korneff et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | von Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,517,321 B2 | 12/2016 | Buechi et al. |
| 9,545,493 B2 | 1/2017 | Mayer et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| 9,838,759 B2 | 12/2017 | Kirmse et al. |
| 9,855,398 B2 * | 1/2018 | Klasek ............... A61M 16/0633 |
| 9,861,778 B2 | 1/2018 | Bath et al. |
| 9,937,314 B2 | 4/2018 | Buechi et al. |
| 9,937,316 B2 | 4/2018 | Buechi et al. |
| 9,943,108 B2 * | 4/2018 | Lord ........................ A24F 7/00 |
| 10,046,136 B2 | 8/2018 | Pujol |
| 2001/0017134 A1 | 8/2001 | Bahr |
| 2001/0050080 A1 | 12/2001 | Seakins et al. |
| 2002/0100320 A1 | 8/2002 | Smith et al. |
| 2003/0116556 A1 * | 6/2003 | Li ........................ A47J 27/004 219/433 |

(56) References Cited

U.S. PATENT DOCUMENTS

| | | |
|---|---|---|
| 2003/0148664 A1 | 8/2003 | Cheng |
| 2003/0200727 A1 | 10/2003 | Kim |
| 2003/0236015 A1 | 12/2003 | Edirisuriya et al. |
| 2004/0074493 A1 | 4/2004 | Seakins et al. |
| 2004/0087213 A1 | 5/2004 | Kao |
| 2004/0149284 A1 | 8/2004 | Smith et al. |
| 2004/0221843 A1 | 11/2004 | Baecke |
| 2004/0239001 A1 | 12/2004 | Edirisuriya et al. |
| 2004/0244858 A1 | 12/2004 | Jeong |
| 2006/0030191 A1 | 2/2006 | Tuin et al. |
| 2006/0118113 A1 | 6/2006 | Bremner et al. |
| 2006/0137445 A1 | 6/2006 | Smith et al. |
| 2006/0237012 A1 | 10/2006 | Thudor et al. |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0175473 A1 | 8/2007 | Lewis et al. |
| 2007/0248934 A1 | 10/2007 | Mosimann |
| 2007/0284361 A1 | 12/2007 | Nadjafizadeh et al. |
| 2008/0000474 A1 | 1/2008 | Jochle et al. |
| 2008/0051674 A1 | 2/2008 | Davenport et al. |
| 2008/0066751 A1 | 3/2008 | Polacsek |
| 2008/0105257 A1 | 5/2008 | Klasek et al. |
| 2008/0142019 A1 | 6/2008 | Lewis et al. |
| 2008/0202512 A1 | 8/2008 | Kressierer/Huber et al. |
| 2008/0251073 A1 | 10/2008 | Jassell et al. |
| 2009/0045829 A1* | 2/2009 | Awazu ............... G01R 31/2865 324/762.05 |
| 2009/0050150 A1 | 2/2009 | Rossen et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107980 A1* | 4/2009 | Andel ............... A61M 16/1075 219/443.1 |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0194106 A1 | 8/2009 | Smith et al. |
| 2009/0223514 A1 | 9/2009 | Smith et al. |
| 2009/0301482 A1 | 12/2009 | Burton et al. |
| 2009/0320840 A1 | 12/2009 | Klasek et al. |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0206308 A1* | 8/2010 | Klasek ............... A61M 16/0066 128/203.27 |
| 2010/0242963 A1 | 9/2010 | Brieger et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0049123 A1* | 3/2011 | Frock ............... A21B 3/04 219/393 |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0162647 A1 | 7/2011 | Huby et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0017904 A1 | 1/2012 | Ratto et al. |
| 2012/0060838 A1 | 3/2012 | Laura Lapoint et al. |
| 2012/0073573 A1 | 3/2012 | Thudor et al. |
| 2012/0125333 A1 | 5/2012 | Bedford et al. |
| 2012/0138595 A1* | 6/2012 | Watakabe ............... H05B 3/34 219/528 |
| 2012/0146251 A1* | 6/2012 | Heine ............... A61M 16/1095 261/128 |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0248636 A1 | 10/2012 | Fridberg et al. |
| 2012/0255758 A1 | 10/2012 | Lee |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0081621 A1 | 4/2013 | Korneff et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0239966 A1 | 9/2013 | Klasek et al. |
| 2013/0247905 A1 | 9/2013 | Miller |
| 2013/0255677 A1 | 10/2013 | Varga |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0216446 A1 | 8/2014 | Wruck |
| 2014/0251322 A1 | 9/2014 | Miller |
| 2014/0251331 A1 | 9/2014 | Korneff et al. |
| 2014/0311489 A1 | 10/2014 | Heine et al. |
| 2014/0318536 A1 | 10/2014 | Landis et al. |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0339200 A1 | 11/2016 | Bath et al. |
| 2016/0367776 A1 | 12/2016 | Landis et al. |
| 2016/0367779 A1 | 12/2016 | Landis et al. |
| 2017/0095635 A1 | 4/2017 | Huby |
| 2017/0136198 A1 | 5/2017 | Delangre et al. |
| 2017/0161461 A1 | 6/2017 | Delangre et al. |
| 2017/0173293 A1 | 6/2017 | Osborne et al. |
| 2017/0239432 A1 | 8/2017 | Delangre et al. |
| 2017/0326320 A1 | 11/2017 | Baigent et al. |
| 2018/0028773 A1 | 2/2018 | Jan et al. |
| 2018/0078730 A1 | 3/2018 | Bath et al. |
| 2018/0169361 A1 | 6/2018 | Dennis et al. |
| 2018/0250491 A1 | 9/2018 | Row et al. |

FOREIGN PATENT DOCUMENTS

| | | |
|---|---|---|
| CA | 2495451 | 3/2004 |
| CN | 1598510 | 3/2005 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 102004030747 | 1/2006 |
| DE | 20 2005 008 152.3 | 10/2006 |

(56) References Cited

FOREIGN PATENT DOCUMENTS

| | | |
|---|---|---|
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 759.7 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0201985 | 11/1986 |
| EP | 291921 | 11/1988 |
| EP | 535952 | 4/1993 |
| EP | 0567158 | 10/1993 |
| EP | 0885623 | 12/1998 |
| EP | 1262208 | 12/2002 |
| EP | 1352670 | 10/2003 |
| EP | 1646910 | 4/2006 |
| EP | 1669098 | 6/2006 |
| EP | 1683066 | 7/2006 |
| EP | 1741462 | 1/2007 |
| EP | 1924311 | 5/2008 |
| EP | 2079505 | 7/2009 |
| EP | 2089086 | 8/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2415445 | 2/2012 |
| EP | 2471568 | 7/2012 |
| EP | 2498854 | 9/2012 |
| EP | 2514478 | 10/2012 |
| EP | 2524714 A1 | 11/2012 |
| EP | 2575944 | 4/2013 |
| EP | 2143459 B1 | 8/2013 |
| EP | 2640451 | 9/2013 |
| EP | 2651481 | 10/2013 |
| EP | 2654869 | 10/2013 |
| EP | 2667919 | 12/2013 |
| EP | 2760516 | 8/2014 |
| EP | 2830695 | 2/2015 |
| EP | 2877224 | 6/2015 |
| EP | 3013402 | 5/2016 |
| EP | 3053623 | 8/2016 |
| GB | 1310949 | 3/1973 |
| GB | 1364127 | 8/1974 |
| GB | 2176313 | 12/1986 |
| GB | 2495771 A | 4/2013 |
| JP | 03194747 | 8/1991 |
| JP | H0623051 | 2/1994 |
| JP | 11248076 | 9/1999 |
| JP | 2001095920 | 4/2001 |
| JP | 2003275312 | 3/2003 |
| JP | 4242816 | 3/2009 |
| NZ | 564886 | 2/2011 |
| NZ | 586325 | 1/2012 |
| NZ | 597020 | 6/2013 |
| NZ | 604137 | 6/2014 |
| NZ | 710078 | 1/2017 |
| NZ | 710351 | 1/2017 |
| NZ | 631008 | 7/2017 |
| WO | WO 9718001 | 5/1997 |
| WO | WO 2000/029057 | 5/2000 |
| WO | WO 2001/032069 | 5/2001 |
| WO | WO 0197894 | 12/2001 |
| WO | WO 0266107 | 8/2002 |
| WO | WO 02066106 | 8/2002 |
| WO | WO 2004/011072 | 2/2004 |
| WO | WO 2005/011785 | 2/2005 |
| WO | WO 2005/021076 | 3/2005 |
| WO | WO 2006/092001 A1 | 9/2006 |
| WO | WO 2007/051230 | 5/2007 |
| WO | WO 2008/055307 | 5/2008 |
| WO | WO 2008/055308 | 5/2008 |
| WO | WO 2008/058328 | 5/2008 |
| WO | WO 2008/060295 | 5/2008 |
| WO | WO 2008/076230 | 6/2008 |
| WO | WO 2009/022004 | 2/2009 |
| WO | WO 2009/085995 A1 | 7/2009 |
| WO | WO 2010/031125 | 3/2010 |
| WO | WO 2010/031126 | 3/2010 |
| WO | WO 2010/031126 A1 | 3/2010 |
| WO | WO 2012/065999 | 5/2012 |
| WO | WO 2012/135912 | 10/2012 |
| WO | WO 2012/135912 A1 | 10/2012 |
| WO | WO 2012/164407 | 12/2012 |
| WO | WO 2013/026901 | 2/2013 |
| WO | WO 2013/045575 | 4/2013 |
| WO | WO 2013/049660 | 4/2013 |
| WO | WO 2013/050907 | 4/2013 |
| WO | WO 2013/127474 | 9/2013 |
| WO | WO 2013/147623 A1 | 10/2013 |
| WO | WO 2013/165263 A1 | 11/2013 |
| WO | WO 2014/055407 | 4/2014 |
| WO | WO 2014/077706 | 5/2014 |
| WO | WO 2014/205513 | 12/2014 |
| WO | WO 2015/060729 | 4/2015 |
| WO | WO 2015/160268 | 10/2015 |
| WO | WO 2015/164407 | 10/2015 |
| WO | WO 2016/042522 | 3/2016 |
| WO | WO 2016/089224 | 6/2016 |
| WO | WO 2016/139645 | 9/2016 |
| WO | WO 2017/027906 | 2/2017 |
| WO | WO 2017/126980 | 7/2017 |

OTHER PUBLICATIONS

International Search Report; PCT/NZ2014/000202; dated Jan. 13, 2015; 15 pages.

\* cited by examiner

HUMIDIFICATION SYSTEM

INCORPORATION BY REFERENCE

Any and all applications for which a foreign or domestic priority claim is identified in the Application Data Sheet as filed with the present application are hereby incorporated by reference under 37 CFR 1.57.

The following provisional applications are hereby incorporated by reference in their entirety: the U.S. Provisional Application having the title HUMIDIFICATION SYSTEM and Ser. No. 62/032,462, filed on Aug. 1, 2014; U.S. Provisional Application having the title CONNECTIONS FOR HUMIDIFICATION SYSTEM and Ser. No. 61/877,566, filed on Sep. 13, 2013; the U.S. Provisional Application having the title MEDICAL TUBES AND METHODS OF MANUFACTURE and Ser. No. 61/877,622, filed on Sep. 13, 2013; the U.S. Provisional Application having the title ZONE HEATING FOR RESPIRATORY CIRCUITS and Ser. No. 61/877,736, filed on Sep. 13, 2013; the U.S. Provisional Application having the title HEATING ASSEMBLY and Ser. No. 61/971,474, filed on Mar. 27, 2014.

BACKGROUND

1. Field of the Disclosure

The present disclosure generally relates to humidification systems for providing humidified gases to patients. More particularly, certain features, aspects and advantages of the present disclosure relate to features that improve the performance of such humidification systems.

2. Description of the Related Art

Gas humidification systems deliver heated and humidified gases for various medical procedures, including respiratory treatment, laparoscopy, and the like. While a variety of such systems have been developed, further improvements of such systems are desired.

SUMMARY

One aspect of the present disclosure involves a heater base for supplying humidified gases to a patient or user. The heater base comprises a base portion. The base portion comprises a recessed region. A heater plate is positioned in the recessed region. The heater plate is configured to contact a heat conductive portion of a removable humidification chamber. A guard is configured to control movement of the removable humidification chamber into and out of the recessed region. The guard has a first end and a second end. An anti-racking mechanism cooperates with the guard to cause vertical movement of the first end to translate into coordinated vertical movement of the second end.

In some configurations, the anti-racking mechanism comprises an elongated rod-like member that connects to the first end of the guard and to the second end of the guard.

In some configurations, the elongated rod-like member extends between a first arm and a second arm with the first arm being connected to the first end of the guard and the second arm being connected to the second end of the guard.

In some configurations, the guard comprises a first post near the first end of the guard and a second post near the second end of the guard. The first arm is connected to the first post and the second arm is connected to the second post.

In some configurations, a biasing member is disposed between the guard and another portion of the heater base.

In some configurations, the biasing member comprises at least one compression spring that is mounted between the guard and the another portion of the heater base.

In some configurations, the guard comprises a first support and a second support and the at least one compression spring comprises a first compression spring mounted to the first support and a second compression spring mounted to the second support.

One aspect of the present disclosure involves a chamber for use with a heater base of a humidification system. The chamber comprises an outer wall. An upper wall is connected to the outer wall. The outer wall and the upper wall at least partially define a chamber. An inlet port defines an opening into the chamber through the upper wall. The inlet port has a downward extension that extends below the upper wall into the cavity such that a recess is defined among the downward extension, the upper wall and the outer wall. A baffle is disposed at a lower end of the downward extension.

In some configurations, the baffle extends downward and outward from the lower end of the downward extension such that the baffle directs airflow outward toward the outer wall.

In some configurations, a float is positioned within the cavity and a removable float retainer is configured to extend into the chamber, alongside of the baffle, such that the float retainer can secure the float against movement.

In some configurations, a float is positioned within the cavity. The float comprises a lower surface designed to direct airflow.

In some configurations, the lower surface comprises a recess.

In some configurations, the lower surface comprises a ridge.

In some configurations, the chamber also comprises an outlet port, the outlet port tapering such that at least a portion of the outlet port has a smaller cross-sectional area than an entrance into the outlet port from within the chamber.

Another aspect of the present disclosure involves a conduit hanging end cap for use with a breathing conduit component. The conduit hanging end cap comprises a body configured to be inserted into the conduit component. The body comprises a first end and a second end. The body also comprises a plurality of outer frustoconical tapers positioned between the first end and the second end. A flange extends from the first end of the body. The flange has an outer perimeter that is non-circular and that extends radially outward of a largest portion of the frustoconical tapers.

In some configurations, each of the frustoconical tapers has a widest portion. The flange is closest to the widest part of at least one of the frustoconical tapers compared to the rest of that frustoconical taper.

In some configurations, the conduit hanging end cap further comprises a hanging component extending from the flange.

In some configurations, the hanging component is a loop that extends away from the flange in a direction opposite to the body.

In some configurations, the hanging component comprises a closed loop.

In some configurations, the flange comprises a hexagonal shape.

In some configurations, the end cap is formed of a material that is soft or pliant enough to not cause material damage to a connector of a conduit after connection of the end cap and the connector.

Another aspect of the present disclosure involves a humidification system for humidifying respiratory gases provided to a patient. The humidification system comprises a heater plate. A base supports the heater plate and is configured to receive a removable chamber configured to hold a liquid. One or more springs apply an upward force to the heater plate and urge the heater plate into contact with the removable chamber. The one or more springs are preloaded so that, when the chamber is inserted into the base, the heater plate is required to travel less than 3 mm without diminishing the upward force exerted by the springs on the heater plate.

In some configurations, the upward force is 30-40 Newtons (N).

In some configurations, the upward force is 36-40 Newtons (N).

In some configurations, the upward force is about 35 Newtons (N).

In some configurations, the system further comprises a spring assembly.

In some configurations, the spring assembly comprises a first spring assembly platform supporting a base of the spring; and a screw secured to and extending downward from the bottom of the heater plate. A body of the screw passes through an opening of the first spring assembly platform and a head of the screw is below the first spring assembly platform, wherein the opening of the first spring assembly platform is large enough to allow the screw body to pass through the opening without resistance but not large enough to allow the screw head to pass through the opening.

In some configurations, the spring assembly comprises a spring preloading assembly.

In some configurations, the spring preloading assembly comprises a second spring assembly platform located below the first spring assembly platform. The second spring assembly platform includes an opening is large enough to allow the screw body to pass through the opening without resistance but not large enough to allow the screw head to pass through the opening.

In some configurations, the one or more springs are preloaded so that when the chamber is inserted into the base, the heater plate is required to travel less than 2 mm without diminishing the upward force exerted by the springs on the heater plate.

In some configurations, the one or more springs are preloaded so that when the chamber is inserted into the base, the heater plate is required to travel less than 1 mm without diminishing the upward force exerted by the springs on the heater plate.

In some configurations, the one or more springs are preloaded so that, when the chamber is inserted into the base, the heater plate is required to travel less than 1 mm without diminishing the upward force exerted by the springs on the heater plate.

Another aspect of the present disclosure involves a heater base for supplying humidified gases to a patient. The heater base comprises a heater plate. A spring assembly supports the heater plate. A chamber receiving assembly is configured to receive a removable chamber configured to hold liquid. A base assembly supports the spring assembly and the chamber receiving assembly with the base assembly including at least one egress hole.

In some configurations, the at least one egress hole is configured to allow liquid which falls from the chamber receiving assembly or removable chamber to drain from the base assembly when the base assembly is placed at a tile angle of between 0 and 20 degrees.

In some configurations, the at least one egress hole is at least partially semicircular.

In some configurations, the at least one egress hole located under an edge of the heater plate.

In some configurations, the heater base comprises a second egress hole.

In some configurations, the heater base comprises a third egress hole.

In some configurations, the first, second and third egress holes are placed around a circumference under the heater plate assembly to allow liquid to drain from any tilt direction.

A further aspect of the present disclosure involves a heating assembly in a humidification system. The heating assembly comprises a heating plate. An at least partially flat filament is configured to heat the heating plate.

In some configurations, the at least partially flat filament is configured to be wound around a non-conductive core.

In some configurations, the non-conductive core is flat so that when the at least partially flat filament is would around the non-conductive core the combination of the filament and core forms a flat heating element.

In some configurations, the at least partially flat filament provides higher heating power at lower temperatures than an equivalent round filament.

In some configurations, the heating assembly is configured to heat 80 liters of liquid per minute (Lpm) at 37 degrees Celsius.

In some configurations, the heating assembly is configured to heat 120 liters of liquid per minute (Lpm) at 31 degrees Celsius.

In some configurations, the heating assembly further comprises at least one insulation layer between the at least partially flat filament and the heating plate.

In some configurations, the heating assembly further comprises at least two insulation layers between the at least partially flat filament and the heating plate.

Another aspect of the present disclosure involves a method of controlling a respiratory humidification system. The method comprises monitoring temperature at an outlet port of a chamber; determining whether the outlet port temperature has increased by more than a predetermined amount within a predetermined period of time; and beginning a second procedure if the outlet port temperature has increased by more than the predetermined amount within the predetermined period of time.

In some configurations, the predetermined amount is at least 2° C. and the predetermined period of time is at least 30 seconds.

In some configurations, the method further comprises determining whether a temperature at an inlet port of the chamber is higher than the temperature at the outlet port of the chamber by more than a predetermined amount.

In some configurations, the method further comprises determining whether a temperature at a patient-end of a conduit is lower than the temperature at the outlet port of the chamber by more than a predetermined amount.

In some configurations, the method further comprises monitoring a flow rate of gases and determining whether a decrease in flow rate greater than a predetermined amount has occurred over a predetermined period of time.

In some configurations, the flow rate is monitored by taking instantaneous measurements of flow rate.

In some configurations, time-averaged measurements are used to monitor the flow rate.

In some configurations, the method further comprises testing whether the flow rate has dropped from a flow rate exceeding a first flow rate value to a flow rate below a second flow rate value if it has been determined that the decrease in flow rate has been greater than the predetermined amount over the predetermined period of time.

In some configurations, the method further comprises monitoring a temperature at a patient end of an inspiratory conduit and determining if the temperature decreases by more than a predetermined temperature over a predetermined period of time and, if the temperature decreases by more than the predetermined temperature over a predetermined period of time, beginning a second procedure.

In some configurations, the second procedure is a cool down mode.

Another aspect of the present disclosure involves a method of controlling a respiratory humidification system to deliver a flow of gases to a patient. The method comprises setting a target dew point for the flow of gases within an inspiratory conduit; setting a target temperature for the flow of gases at a patient-end of the inspiratory conduit; during a first phase, energizing a heater plate to achieve the target dew point at a first time after start of the first phase; and, during a second phase after the first phase, energizing the heater plate to achieve the targeted temperature at a second time after start of the second phase.

In some configurations, the first time is at least 5 minutes and less than or equal to 40 minutes.

In some configurations, the second time is less than or equal to 1.5 hours after the start of the first phase.

In some configurations, the method further comprises monitoring a gas temperature at a chamber outlet of the respiratory humidification system.

In some configurations, the method further comprises estimating a dew point of the flow of gases based at least in part on the gas temperature at the chamber outlet.

In some configurations, the target temperature changes as a function of time, having a first target temperature at the first time and a second target temperature at the second time.

In some configurations, the target temperature increases from the first target temperature to the second target temperature during the second phase.

In some configurations, the method further comprises setting a targeted chamber outlet set point that changes over time during the first phase to achieve a targeted humidity.

In some configurations, the targeted humidity is at least about 0.5 mg/L.

In some configurations, the targeted chamber outlet set point is at least 24° C. and less than or equal to 35° C.

Another aspect of the present disclosure involves a respiratory humidification system configured to deliver a flow of gases to a patient. The humidification system comprises a chamber. A heater plate is configured to provide heat to the chamber. The chamber includes a chamber outlet and an inspiratory conduit is configured to couple to the chamber outlet to deliver humidified gas from the chamber to the patient. A controller is configured to control power delivered to the heater plate. The controller is configured to set a target dew point for the flow of gases within the inspiratory conduit; set a target temperature for the flow of gases at a patient-end of the inspiratory conduit; during a first phase, energize the heater plate to achieve the target dew point at a first time after start of the first phase; and during a second phase after the first phase, energize the heater plate to achieve the targeted temperature at a second time after start of the second phase.

In some configurations, the first time is at least 5 minutes and less than or equal to 40 minutes.

In some configurations, the second time is less than or equal to 1.5 hours after the start of the first phase.

In some configurations, the system further comprises a gas temperature probe positioned at the chamber outlet with the gas temperature probe configured to provide an indication of a gas temperature of the flow of gases to the controller.

In some configurations, the controller is further configured to estimate a dew point of the flow of gases based at least in part on the indication of the gas temperature at the chamber outlet.

In some configurations, the target temperature changes as a function of time, having a first target temperature at the first time and a second target temperature at the second time.

In some configurations, the target temperature increases from the first target temperature to the second target temperature during the second phase.

In some configurations, the controller is further configured to set a targeted chamber outlet set point that changes over time during the first phase to achieve a targeted humidity.

In some configurations, the targeted humidity is at least about 0.5 mg/L.

In some configurations, the targeted chamber outlet set point is at least 24° C. and less than or equal to 35° C.

Another aspect of the present disclosure involves a respiratory humidification system configured to deliver a flow of gases to a patient. The humidification system comprises a humidification body comprising a display with a user interface and a chamber. A heater plate is configured to provide heat to the chamber. A chamber outlet is provided and an inspiratory conduit is configured to couple to the chamber outlet to deliver humidified gas from the chamber to the patient, the inspiratory conduit comprising an identification component. A controller is configured to control power delivered to the heater plate based at least in part on a control algorithm. When coupled to the chamber, the controller receives a signal associated with the identification component, and based at least in part on the signal associated with the identification component, selects a suitable control algorithm.

In some configurations, the controller selects a suitable user interface based at least in part on the signal associated with the identification component.

In some configurations, the identification component comprises an ID resistor.

In some configurations, the controller is configured to limit operational capabilities if the signal associated with the identification component indicates that the inspiratory conduit is for use in an infant mode.

In some configurations, the system further comprises a cartridge associated with the inspiratory conduit, with the identification component positioned within the cartridge.

In some configurations, the inspiratory conduit comprises a segmented inspiratory conduit with a plurality of heaters associated with each segment of the inspiratory conduit.

In some configurations, the controller is further configured to control power to the plurality of heaters.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects and advantages of the present disclosure will be described with reference to the following drawings, which are illustrative but should not be limiting of the present disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein should not be limited by any particular embodiments described below.

Various features as described herein can help control the system and increase the likelihood of the patient receiving gases having desired conditions. The features described herein can be used individually or in various combinations and subcombinations in existing humidification systems and/or in improved systems for respiratory humidification, laparoscopy, and other purposes.

Humidification System

Figure 1:
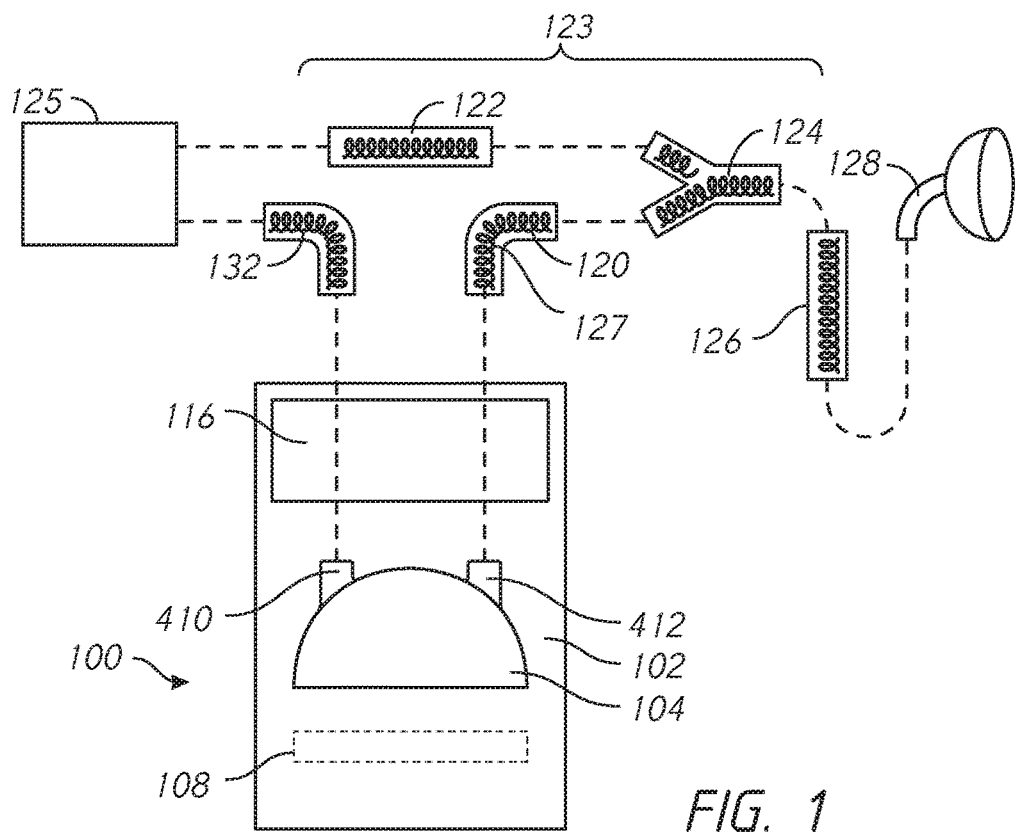
FIG. 1 schematically illustrates an example embodiment of a humidification system.

FIG. 1 schematically illustrates an example embodiment of a humidification system 100 that, in some applications, can be used with breathing treatments, positive pressure apparatus, noninvasive ventilation, and surgical procedures, including but not limited to laparoscopy. Desirably, the humidification system 100 can be adapted to supply humidity or vapor to a supply of gases.

An example embodiment of the humidification system 100 can include a heater base 102 and a humidification chamber 104. The heater base 102 can comprise a heater plate 108. The humidification chamber 104 can be configured to hold a volume of a liquid, such as water. The heater plate 108 can be configured to heat the volume of liquid held within the humidification chamber 104.

The humidification system 100 also can include a gases supply 125. In some configurations, the gases supply 125 can comprise a ventilator or any other suitable source of pressurized gases suitable for breathing or for use in medical procedures. The gases supply 125 can be separate from or combined with the heater base 102.

In some configurations, the humidification system 100 also can include a breathing circuit or breathing circuit assembly 123. One or more of the components of the breathing circuit assembly 123 can be separable from, permanently coupled to or user-fitted to the chamber 104. The breathing circuit assembly 123 can include an inspiratory conduit 120. A chamber end of the inspiratory conduit 120 can be configured to connect to an outlet port 412 of the chamber 104. A patient end of the inspiratory conduit 120 can be configured to connect to the patient, for example, via an interface 128 (for example, nasal cannula, nasal pillows, full face mask, oral-nasal mask, etc.). In some configurations, the inspiratory conduit 120 can be coupled directly to the interface 128.

In some configurations, for example, in configurations in which the gases supply 125 is separate from the heater base 102, the breathing circuit assembly 123 can include a supply conduit 132. A gases supply end of the supply conduit 132 can be configured to connect to an output of the gases supply 125. A chamber end of the supply conduit 132 can be configured to connect to an inlet port 410 of the chamber 104.

In some configurations, such as those used with a ventilator as the gases supply 125, the breathing circuit assembly 123 also can include an expiratory conduit 122. A patient end of the expiratory conduit 122 can be configured to connect to the interface 128. A gases supply end of the expiratory conduit 122 can be configured to connect to a return of the gases supply 125.

In some embodiments, for example as shown in FIG. 1, the patient ends of the inspiratory conduit 120 and the expiratory conduit 122 can be connected to each other via a Y-piece 124. The Y-piece 124 can be connected to a patient interface conduit 126. In some configurations, the patient interface conduit 126 can include a catheter mount, for example but without limitation. The patient interface conduit 126 can be connected to the interface 128. In some embodiments, the Y-piece 124 couples to the interface 128 without an intervening patient interface conduit.

In some configurations, the Y-piece 124 can incorporate structures, coatings or the like to manage condensate. In some configurations, the structures can include microstructures. Interaction between liquids and surfaces including purpose-built microstructures can result in spreading of the liquid onto the surface and inside or on the microstructures. This interaction was further discovered to increase the liquid-vapor interface area and reduce the thickness of the liquid layer on top of the surface. The combination of increased surface area and reduced thickness improve liquid evaporation, compared to liquid of the same volume on a flat surface. As discussed below, the combination of increased surface area, reduced thickness, and heating further improves liquid evaporation.

Figures 28A, 28B:
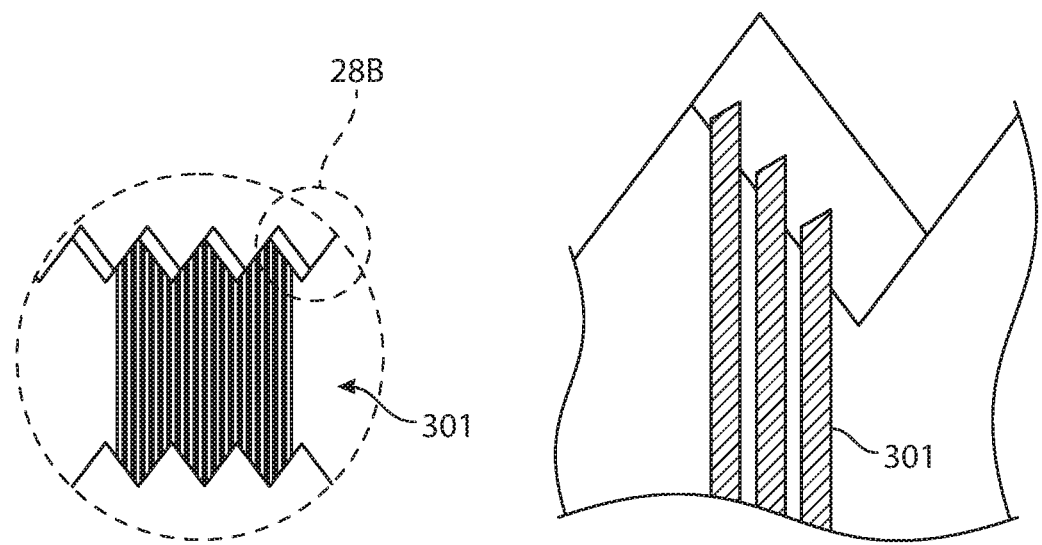
FIGS. 28A and 28B illustrate a tube comprising microstructures.

Accordingly, in various embodiments, at least a portion of the inner walls of the Y-piece 124 can comprise microstructures 301, as shown in FIG. 28A (not to scale). A first magnified view of a portion of the microstructures 301 is shown in FIG. 28B. FIG. 28B shows the microstructures 301 at a greater magnification than FIG. 28A. In FIGS. 28A and 28B, the microstructures 301 can be axially disposed along the Y-piece 124 (that is, the microstructures 301 can extend in a direction perpendicular to longitudinal length of the Y-piece 124). The microstructures 301 can also be used on portions of a tube, overmolded sensors, grommets, other formed components of the humidification system 100, and the like.

Polymers generally have a low surface energy, resulting in poor wettability. In order to improve the liquid spreading capabilities of the microstructures 301 on the Y-piece 124 or other components of the humidification system 100, it can be advantageous to treat the one or more polymers with a material or materials for increasing the surface energy. Surfactants, such as cationic surfactants, can be particularly desirable additive materials. Suitable surface modifying agents include glycerol monostearate (GMS), ethoxylated amine, alkanesulphonate sodium salt, lauric diethanolamide, and additives comprising these substances. MLDNA-418 supplied by Clariant (New Zealand) Ltd. and under the product name "418 LD Masterbatch Antistatic" is a surface modification agent master batch with 5(±0.25)% glycerol monostearate (CAS No. 123-94-4) as an active ingredient. In extruded components, the surface modifying agent can comprise at least about 0.05 (or about 0.05), 0.1 (or about 0.1), 0.15 (or about 0.15), 0.2 (or about 0.2), 0.25 (or about 0.25), 0.3 (or about 0.3), 0.35 (or about 0.35), 0.4 (or about 0.4), 0.45 (or about 0.45), 0.5 (or about 0.5), 1.1 (or about 1.1), 1.2 (or about 1.2), 1.3 (or about 1.3), 1.4 (or about 1.4), or 1.5 (or about 1.5) wt. % of the total extrudate. For example, in at least one embodiment, a tube extrudate comprises 0.25 wt. % (or about 0.25 wt. %) of surface modifying agent. As another example, in at least one embodiment, the tube extrudate comprises 0.5 wt. % (or about 0.5 wt. %) of surface modifying agent.

Other methods can also be used to increase surface energy. Suitable methods include physical, chemical, and radiation methods. Physical methods include, for example, physical adsorption and Langmuir-Blodgett films. Chemical methods include oxidation by strong acids, ozone treatment, chemisorption, and flame treatment. Radiation methods include plasma (glow discharge), corona discharge, photoactivation (UV), laser, ion beam, electron beam, and gamma irradiation.

By selecting a suitable surface modification method or agent, it is possible to provide a tube wall or other formed component having surface property contact angles of less than 50 (or about 50), 45 (or about 45), 40 (or about 40), 35 (or about 35), 30 (or about 30), 25 (or about 25), 20 (or about 20) degrees)(°, as measurable by an angle measurement device such as a goniometer. For instance, tube walls having surface property contact angles of less than 35° (or about 35°) provide useful results. Desirably, the contact angle is less than $\pi/2$ (or about $\pi/2$). More desirably, the contact angle is 0° or about 0°.

TABLE 1 below shows contact angle measurements for various LLDPE samples, including a sample treated with a surface-modifying agent and a sample treated with radiation. The contact angle measurements were based on static drop shape testing methods conducted in accordance with ASTM Standard D7334, 2008, "Standard Practice for Surface Wettability of Coatings, Substrates and Pigments by Advancing Contact Angle Measurement."

TABLE 1

| Description of Surface | Liquid | Average Contact Angle (degrees) |
|---|---|---|
| Linear Low-density Polyethylene (LLDPE), as manufactured | Water | 97.39 |
| Linear Low-density Polyethylene (LLDPE), fluorinated, washed | Water | 67.56 |
| Linear Low-density Polyethylene (LLDPE), plasma-treated, 10% $O_2$, 300 Watts, 30 seconds | Water | 44.98 |
| Linear Low-density Polyethylene (LLDPE), with 5% MLDNA-418 as surface modification agent additive | Water | 33.09 |

The sample with 5% MLDNA-418 surface modifying agent produced the lowest measured contact angle compared to other surface modification methods tested.

As discussed above, in certain embodiments, the additive material is added to the bulk polymer extrudate. It can be desirable to add the material in the polymer matrix so that the additive material replenishes the surface for the useful life of the tube or other component. In certain configurations, the material can be added as a surface treatment on the polymer, for example, by coating a surface of the polymer with the material. For example, a microstructured surface can be brushed, sprayed, or otherwise coated with additive material such as HYDRON anti-fog coating (MXL Industries, Lancaster, Pa.), EXXENE anti-form coatings such as HCAF-100 (Exxene Corporation, Corpus Christi, Tex.), and MAKROLON anti-fog (Bayer Corporation) to produce a thin (for example, 1 µm or thereabout) coating of additive material. A surface coating can be desirable because of low costs and ease of manufacture.

In certain configurations, a thin film of hydrophilic material such as breathable polyurethanes, for example, ESTANE 58245 (Lubrizol Corporation, Wickliffe, Ohio), breathable polyesters, for example, ARNITEL VT3108 (DSM Engineering Plastics, Sittard, Netherlands), or breathable polyamides, for example PEBAX (Arkema, Colombes, France) can be cast as a surface modifying agent. These hydrophilic materials can absorb moisture and become very wettable. An example method of implementing the hydrophilic thin film includes dissolving the breathable polymer in a solvent, casting the mixture, and allowing the solvent to evaporate, thus leaving a thin film of the breathable material on the microstructures. For instance, ESTANE 58245 pellets can be dissolved in a tetrahydrofuran (THF) of dimethylformamide (DMF) solvent and cast onto microstructures machined from brass or aluminum using a micromilling process. Typical dimensions for the thin film are in the range of 1 to 10 µm (or about 1 to 10 µm). Preferably, the solvent, breathable material, and microstructure material combination is selected such that the microstructure shape and quality is not substantially influenced, for example, by dissolving the microstructures with the solvent.

Preferably the surface modification agent comprises at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate. More preferably the surface modification agent comprises about 0.25 wt. % of the total extrudate. Alternatively preferably the surface modification agent comprises about 0.5 wt. % of the total extrudate.

The contact angle is the angle formed by the solid surface of the component or tube wall and the tangent line to the upper surface at the end point of a liquid droplet. Contact angle measurement is a non-destructive method of determining the wetting behavior of liquids on a solid surface. It enables the calculation of surface and interfacial tension along with spreading coefficients. The surface tension calculated from the contact angle data are a characteristic measurement for the respective surface and fluid system.

The contact angle between a liquid and a surface can be measured using a goniometer (angle measurement device). A precise volume of the liquid is dispensed on the cleaned and dried flat test surface using a precision syringe. The droplet is allowed to stabilize for a few seconds and a high magnification camera is used to capture the image of the droplet. The image is digitised and the angle between the test surface and the tangent line along the droplet surface is measured.

Reducing contact angle increases contact area between the droplet and solid surface, and also reduces droplet thickness, enhancing heat conduction through the droplet. Both effects increase droplet evaporation rate.

Increasing the energy of a surface reduces the contact angle of a droplet placed on the surface. In this manner, a droplet of liquid on the surface of a higher energy surface can preferentially have a greater surface area in contact with the surface, than a surface of relatively lower energy.

Advantageously, the droplet may be spread across a larger surface area of the surface and, therefore, be more likely to re-evaporate into the gas stream flowing through the component or tube. For example, the droplet or bead may spread across the internal surface of the Y-piece 124, allowing greater surface area for re-evaporation into the passing gas stream.

In respect of surface modification, it should be appreciated that in various aspects of the disclosed systems, a component and its tubular body can be formed from a single extrudate where the component and/or body has a modified surface. Modified surfaces may preferably facilitate the advantages of re-evaporation rates or droplet migration as described above.

In use, the humidification chamber 104 can be installed on the heater plate 108. The heater plate 108 heats liquid in the chamber 104 to produce vapor. In some configurations, gases flow from the gases supply 125, through the supply conduit 132, and into the humidification chamber 104 through the inlet port 410. The gases pass over the liquid in the humidification chamber 104 and mix with the vapor. Humidified gases exit the humidification chamber 104 through the outlet port 412 and flow through the inspiratory conduit 120 to the patient. The patient inhales the humidified gases supplied through the inspiratory conduit 120. In some embodiments, gases exhaled by the patient are returned to the gases supply 125 through the expiratory conduit 122. Any or all of the components of the breathing circuit assembly 123 can include a heating element, for example, a heating wire 127, to help maintain the gases at a desired temperature and to reduce the likelihood of significant condensation formation in the conduits.

Heater Base

The heater base 102 illustrated in FIGS. 2-7 is arranged and configured in accordance with certain features, aspects and advantages of the present disclosure. FIGS. 2-7 illustrate the heater base 102 in proportional and to scale.

In the illustrated embodiment, the heater base 102 includes a base portion 202. The base portion 202 is the lower portion in the illustrated embodiment. In some configurations, the base portion 202 supports the balance of the heater base 102. The base portion 202 can include the heater plate 108. In the illustrated configuration, the base portion 202 comprises one or more side surfaces 140 that wrap upward to a top surface 142. The top surface 142 generally encircles, or surrounds at least a portion of, the heater plate 108. In the illustrated configuration, the one or more side surfaces 140 join to a front surface 141.

The heater base 102 also can include a spine portion 210. The spine portion 210 can extend generally upwardly from a rear of the base portion 202. In some configurations, the spine portion 210 is monolithic and integrally formed with the base portion 202. The spine portion 210 can include one or more side surfaces 144. The one or more side surfaces 144 can wrap generally forwardly to a front surface 146. In some configurations, the one or more side surfaces 144 can extend upwardly to an upper surface 148. In the illustrated configuration, the one or more side surfaces 144 extend rearwardly to a rear surface 149 of the spine portion 210.

Figure 4:
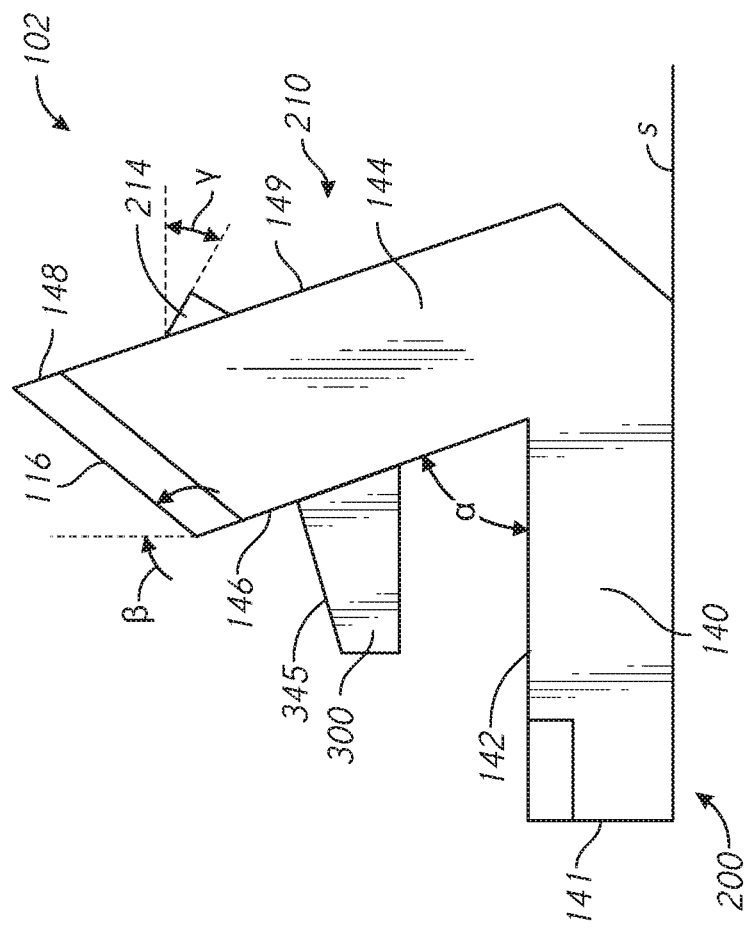

With reference to FIG. 4, in some embodiments, the front surface 146 of the spine portion 210 extends from the top surface 142 of the base portion 202 at an angle α less than 90°. In some configurations, the spine portion 210 is inclined forward at about 22°. The spine portion 210 can slope forward relative to perpendicular to a surface S upon which the base portion 202 will rest. As such, the spine portion 210 can lean toward the location that supports the chamber 104 (see FIG. 8A). In some configurations, as shown in FIG. 4, both the front surface 146 and the rear surface 149 of the spine portion 210 incline forwardly toward the chamber 104.

With reference again to FIG. 2, a heater base display 116 can be located on an upper portion of the spine portion 210. The display 116 can provide information to and/or receive input from an operator. In some configurations, the heater base display 116 can be just below the upper surface 148 of the spine portion 210, as shown. In some configurations, the heater base display 116 is positioned vertically higher than the chamber 104 when the chamber 104 is installed on the heater base 102. By positioning the heater base display 116 above the chamber 104, the chamber 104 is less likely to obstruct the view of, or access to, the heater base display 116.

In the illustrated configuration, the heater base display 116 angles between the upper surface 148 of the spine portion 210 and a portion of the front surface 146. Moreover, the heater base display 116 inclines rearwardly relative to vertical, as shown in FIG. 4. In the illustrated embodiment, the display 116 reclines rearwardly from vertical at an angle β. In some configurations, the display 116 reclines rearwardly by an angle of about 22° from vertical. Other angles also are possible. In the illustrated configuration, the spine portion 210 inclines forwardly toward the chamber 104 while the display 116 reclines rearwardly away from vertical. The angled orientation of the spine portion 210 and/or the display 116 provides a better view of, and access to, the display 116. For example, if the heater base 102 is positioned below the operator's horizontal line of sight, the reclining display 116 facilitates viewing by the operator.

Figure 8A:
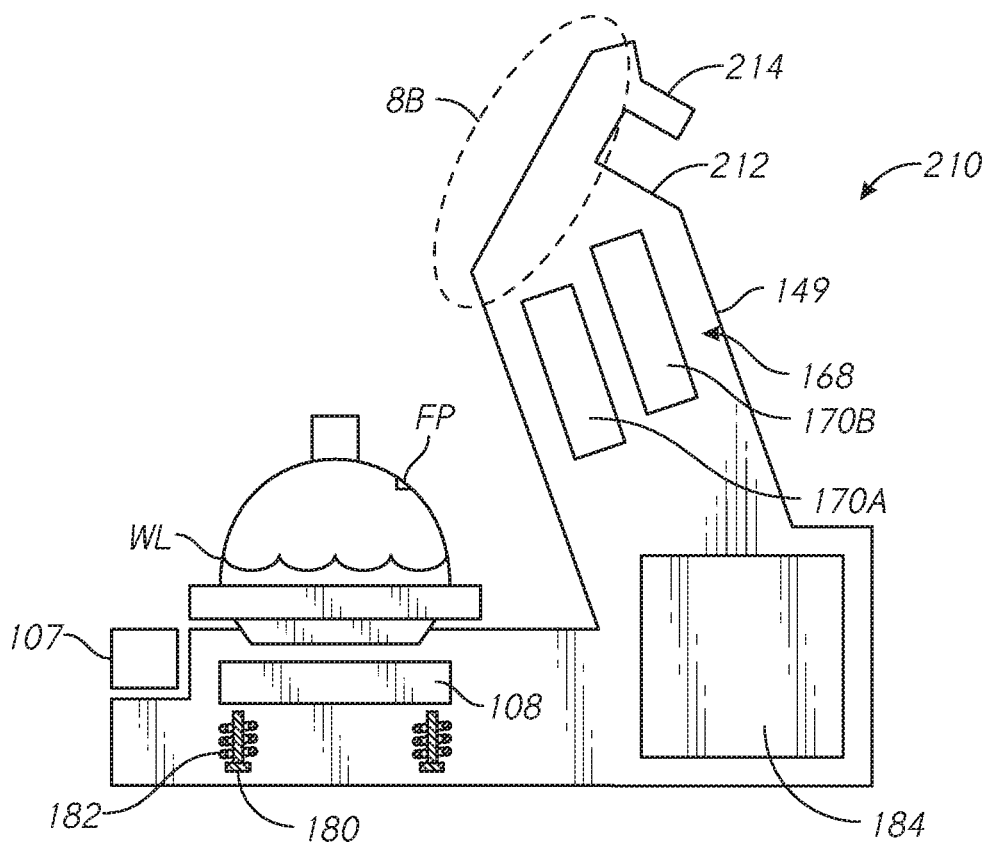
FIG. 8A is a schematic side view of the heater base of FIGS. 2-7 with certain internal components illustrated, a chamber installed on the heater base and the cartridge not shown for clarity.
Figure 8B:
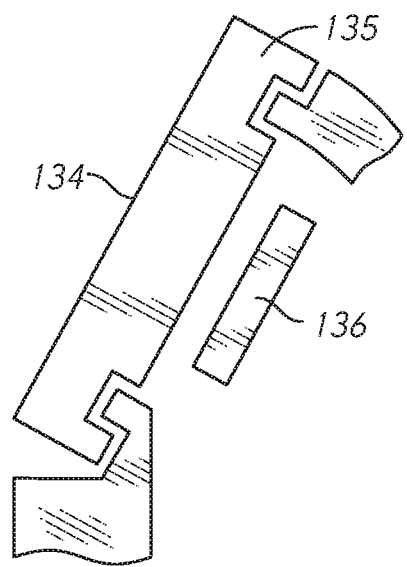
FIG. 8B is an enlarged view of a display module of the heater base of FIG. 8A.

With reference again to FIG. 2 and additional reference to FIGS. 8A and 8B, the display 116 can form a portion of a display module 134. The display module 134 can be configured for simplified replacement. For example, the display module 134 can be quickly and easily removed from the heater base 102 to allow for servicing and/or replacement if needed. The illustrated display module 134 can include a carrier 135 that generally surrounds the screen of the display 116. The carrier 135 supports the screen (for example, the glass and the LCD assembly), as well as a user interface board 136, a power button 137 (see FIG. 2), a gasket and a speaker (not shown). The carrier 135 can secured in position using any suitable technique. In some configurations, the carrier 135 is secured to a portion of the heater base 102 using threaded fasteners such that replacement of the screen, the board 136, the power button 137 and the speaker, among other components, can be quickly and easily accomplished.

With reference to FIG. 8A, the spine portion 210 comprises a cavity 168. The cavity 168 is generally defined by the one or more side surfaces 144, the front surface 146, the upper surface 148 and the rear surface 149 of the spine portion 210. The heater base 102 can include one or more boards 170a, 170b, that are mounted within the cavity 168. The boards 170a, 170b can include a control board, a power board, and one or more extension or mezzanine boards. The boards can include processors and one or more memories or other suitable electronic or electrical components. The heater plate 108 can be controlled through the one or more processors of the heater base 102 such that the heat transferred into the liquid, and therefore the amount of humidity produced, can be varied.

In some embodiments, the boards 170a, 170b contain many or most of the electrical components of the heater base 102. As described herein and shown in FIGS. 12-14, in some configurations, the humidification chamber 104 includes a plastic formed body 103 and a heat conductive base 105 sealed to the body 103. If the base 105 is not fully sealed to the body 103 or the seal is compromised, liquid may leak from the chamber 104 between the body 103 and the base 105. Therefore, in some embodiments, the boards 170a, 170b are located such that the boards 170a, 170b and the related electrical components are vertically higher than a seam between the body 103 and the base 105 of the chamber 104 when the chamber 104 is installed on the heater base 102. As shown in FIG. 8A, the boards 170a, 170b are located such that the components are vertically higher than a normal liquid level WL that is expected to be present within the chamber 104 when the chamber 104 is installed on the heater base 102. As also shown in FIG. 8A, the boards 170a, 170b are located such that the components are generally vertically higher than a fill port level FP of the chamber 104 when the chamber 104 is installed on the heater base 102. In the illustrated configuration, a majority of one or more of the boards 170a, 170b is located vertically higher than a top surface of the chamber 104 that defines the liquid-containing cavity of the chamber 104 when the chamber 104 is installed on the heater base 102. Such arrangements can advantageously help protect the electrical components from liquid that might drip, splash, or otherwise be transferred from the chamber 104 onto the heater base 102.

Figure 5A:
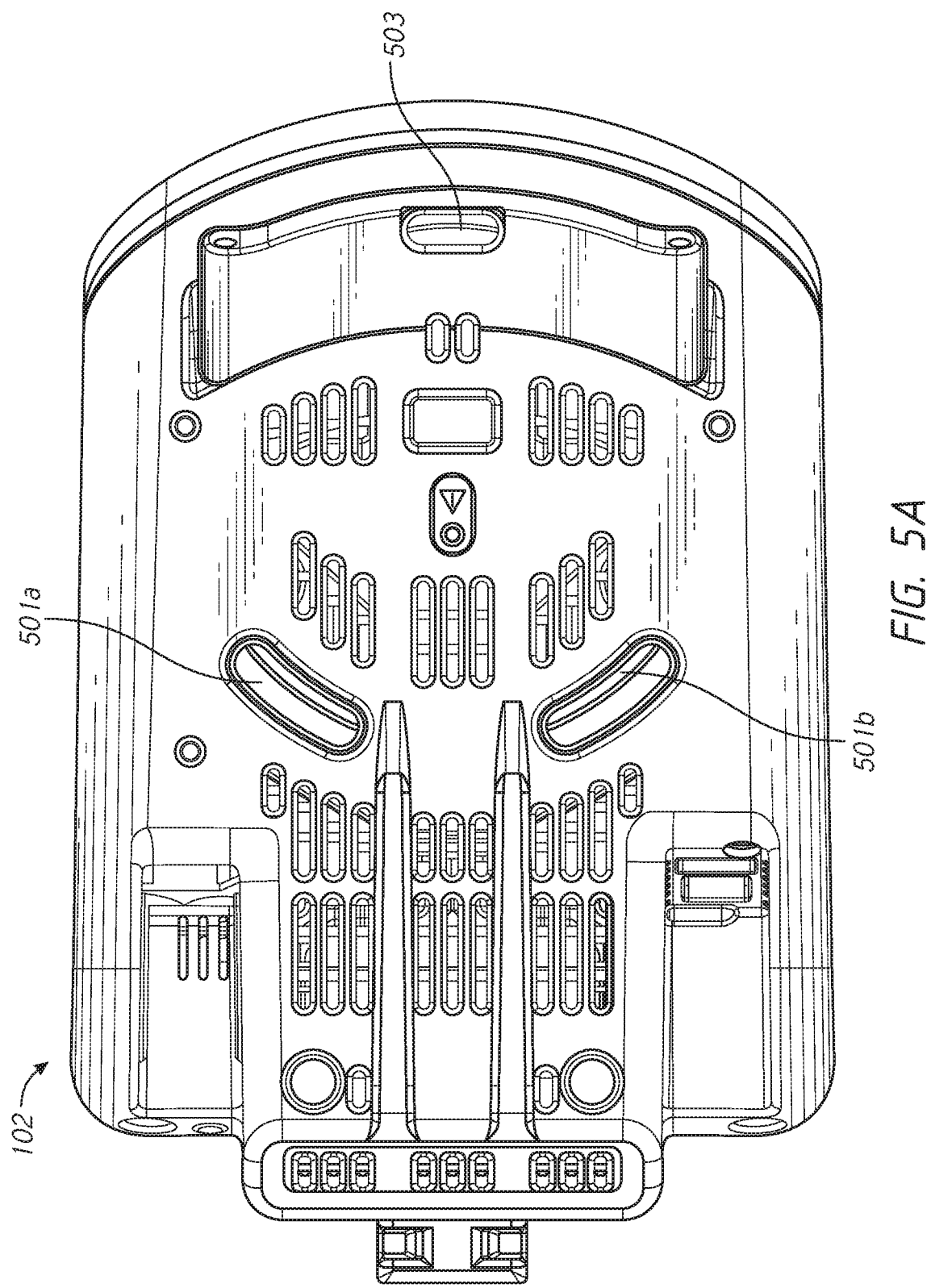

FIG. 5A illustrates an embodiment of liquid egress holes on the bottom of the heater base 102, including holes 501a, 501b, 503. These holes provide drainage from the heater base 102 for up to at least a 20 degree tilt of the heater base 102 without compromising structural strength. Drainage is important so that liquid collecting on the bottom of the heater base 102 does not pool sufficiently to immerse electrical components, such as a heater plate assembly, which could cause electrical shorts or increase the chance of electric shock to a user touching the heater base 102.

Figure 6:
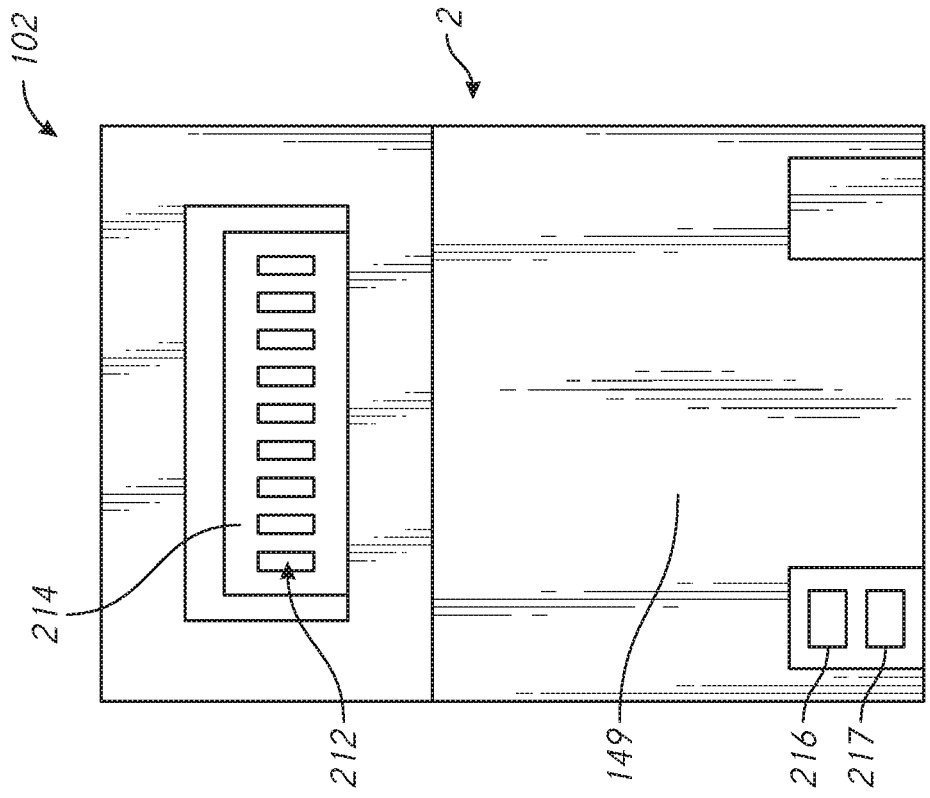

As illustrated in FIG. 6, the rear surface 149 of the spine portion 210 of the heater base 102 can include air vents 212. The air vents 212 advantageously allow for cooling of the electrical components within the heater base 102, including but not limited to the components on the boards 170a, 170b as well as a power transformer 184, for example.

In some configurations, the rear surface 149 of the spine portion 210 of the heater base 102 further includes a vent cover 214. The vent cover 214 extends outwardly from the rear surface 149 of the spine portion 210 of the heater base 102 to at least partially or completely cover the air vents 212. As shown in FIG. 4, the vent cover 214 extends at an angle γ below or negative from horizontal. By extending downwardly and outwardly, the vent cover 214 helps inhibit liquid, dust, and/or other materials from entering the heater base 102 through the air vents 212 and potentially harming the electrical components inside. In some embodiments, the vent cover 214 can also act as a handle or grip to allow a user to more easily carry and move the heater base 102.

The heater base 102 can also include one or more data transfer ports 216, 217 as shown in FIG. 6. The ports 216, 217 can receive memory sticks. Memory sticks can be used to transfer data to or from the heater base 102 and/or to update the software installed on the heater base 102. The ports 216, 217 can also allow the heater base 102 to be connected to a computer and/or a module that allows for connection to other devices.

Figure 9:
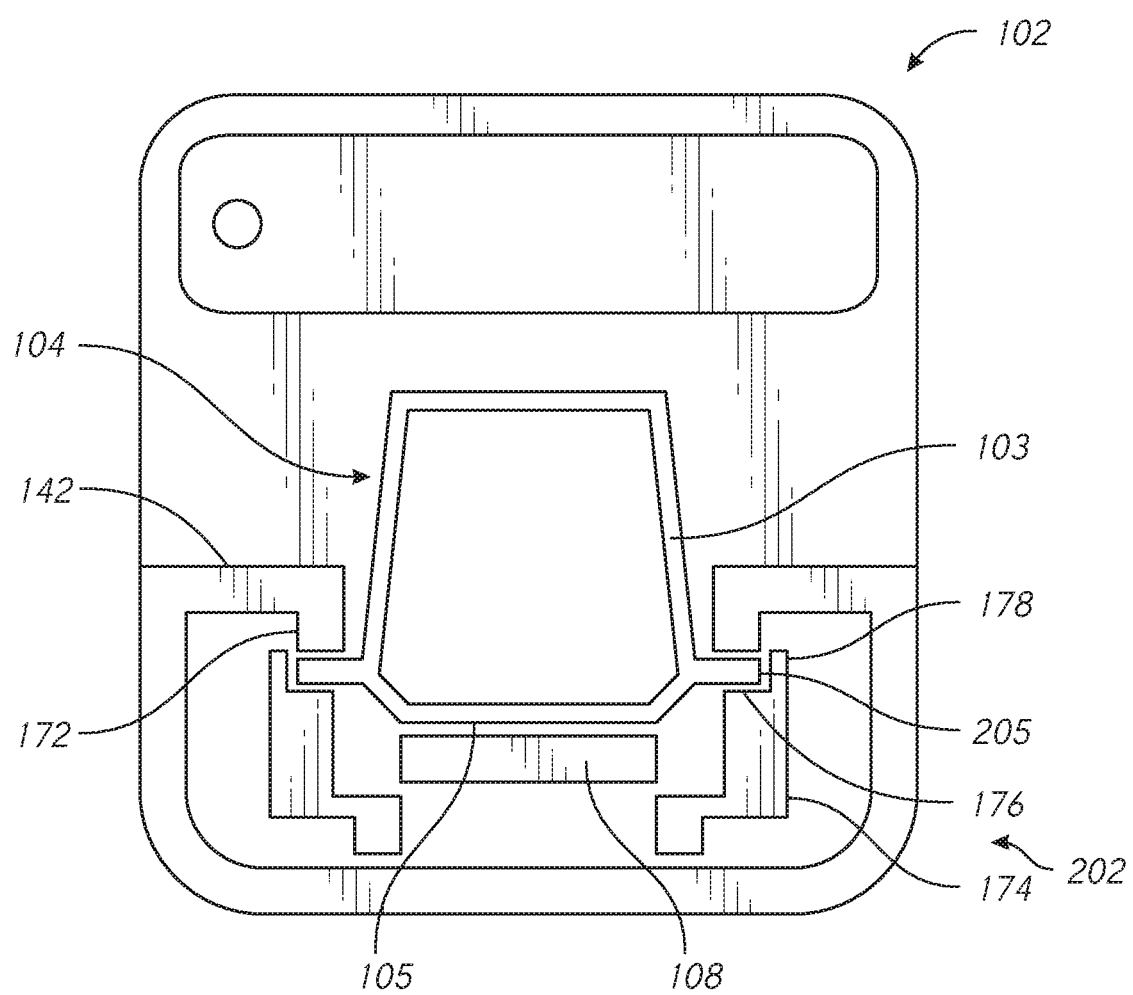
FIG. 9 is a partial front section view of the chamber installed on the heater base.

With reference again to FIG. 2 and additional reference to FIG. 9, the top surface 142 of the base portion 202 of the heater base 102 defines at least a portion of an opening 143. The opening 143 is located vertically higher than the heater plate 108 when the chamber 104 is positioned on the heater plate 108. The opening 143 receives the chamber 104 and enables the chamber 104 to be positioned atop the heater plate 108. Notably, while the illustrated embodiment does not show the heater plate 108 in contact with the chamber 104, the heater plate 108, as will be discussed, preferably is biased upward into engagement with the chamber 104 such that the top surface of the heater plate 108 will be in contact with the base 105 of the chamber 104.

Figure 10:
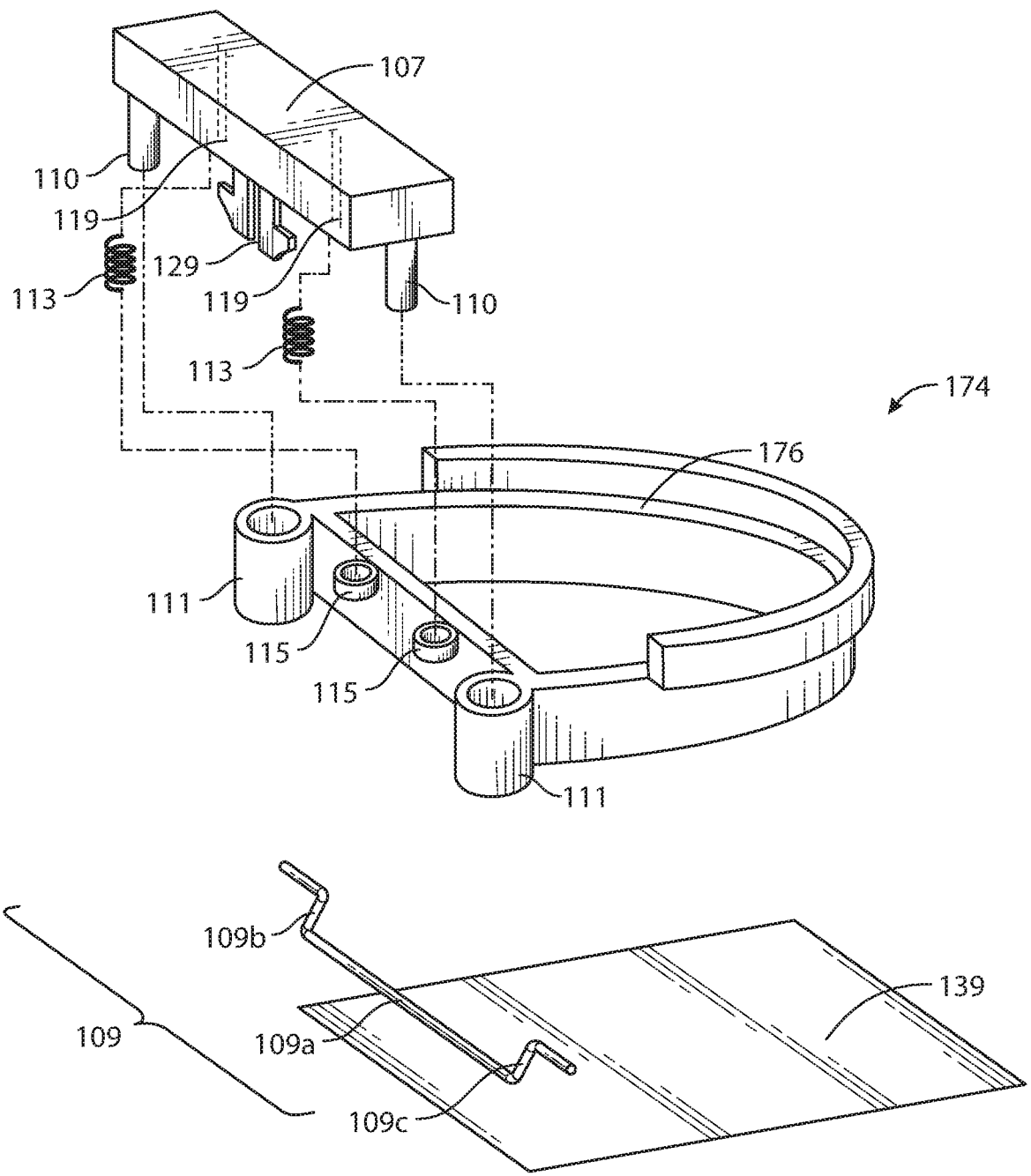
FIG. 10 is an exploded view of a portion of the components of the heater base of FIGS. 2-7.

With reference to FIG. 9, the top surface 142 also includes a rim edge 172. The rim edge 172 can extend along at least a portion of a perimeter of the opening 143. As shown in FIG. 10, the heater base 102 includes an inner chassis 174. The inner chassis 174 generally encircles the heater plate 108. The inner chassis 174 also includes a rim edge 176. The rim edge 176 of the inner chassis 174 is positioned generally vertically below the rim edge 172 of the top surface 142. Accordingly, because the rim edges 172, 176 are vertically spaced apart, a groove 178 is formed between the rim edge 172 of the top surface 142 and the rim edge 176 of the inner chassis 174. The groove 178 can have a thickness of, for example, about 4 mm. In some embodiments, the base 105 of the humidification chamber 104 includes a lip 205 that protrudes beyond a perimeter of the body 103.

For use, an operator installs the humidification chamber 104 on the heater base 102 by sliding the chamber 104 onto the heater plate 108. The lip 205 of the chamber 104 rests or is trapped in the groove 178. In some embodiments, the inner chassis 174 does not include a rim edge 176, and thus the groove 178 is not formed. As discussed above, the heater plate 108 can be spring loaded in some configurations. For example, as shown in FIG. 8A, the heater plate 108 can be mounted on springs 182. In some configurations, the springs 182 can be mounted around support screws 180. The spring loading allows the heater plate 108 to be depressed during installation of the chamber 104. When the chamber 104 is installed, the spring-loaded heater plate 108 presses upward on the chamber 104 while the rim edge 172 resists upward movement of the lip 205 of the chamber 104. The rim edge 172 helps hold the chamber 104 in place and promote contact between the base 105 and the heater plate 108.

In some embodiments, the rim edge 176 of the inner chassis 174 helps inhibit excessive downward movement of the chamber 104. Accordingly, the rim edge 176 helps reduce the likelihood of damage to certain components of the system, such as, for example but without limitation, sensors that may be mounted on the heater base 102. Without the rim edge 176, the spring-loaded heater plate 108 may depress, for example, if downward pressure is applied to the chamber 104 when connecting the supply conduit 132 and/or the inspiratory conduit 120. Without the lower rim edge 176, the chamber 104 may have a vertical range of motion of about 2 mm to about 5 mm. The lower rim edge 176 can reduce the range of motion to about 0.5 mm.

The upward force exerted by the springs 182 against the heater plate 108 forces the heater plate 108 up against the bottom surface of the chamber 104. The greater the force exerted by the springs 182, the better the heat conduction between the heater plate 108 and the chamber 104. This is because the greater the upward force, the more heater plate 108 surface area will be in direct contact with the chamber 104 bottom surface, thus increasing conduction. However, the greater the force exerted by the springs 182, the more difficult it is to insert and remove the chamber 104 from the base portion 202. It has been discovered that upward force of 30-40 Newtons (N) is optimal. In an embodiment, the force is in the range of 36-40 N. In an embodiment, the force is in the range of 35+/−5 N.

In order to achieve this type of force while easing a user's ability to insert and remove the chamber 104, the springs 182 can be preloaded. Preloading can be achieved, for example, by dropping the initial height of the heater plate 108 so that the springs 182 have less travel, while providing the optimal amount of force. This allows the user to insert the chamber 104 into the heater base 102 without having to force the heater plate 108 down a greater distance than is necessary to achieve the desired upward force on the heater plate 108.

For example, in an embodiment, the heater plate 108 is configured to travel less than one millimeter to a few millimeters. This can be done, for example, by limiting the range of the support screws 180 (as shown in FIG. 8A). In an embodiment, the support screws 180 can include a washer or other platform to limit the range of motion of the springs 182 and/or the heater plate 108 in order to achieve the desired pre-loading.

Figure 29A:
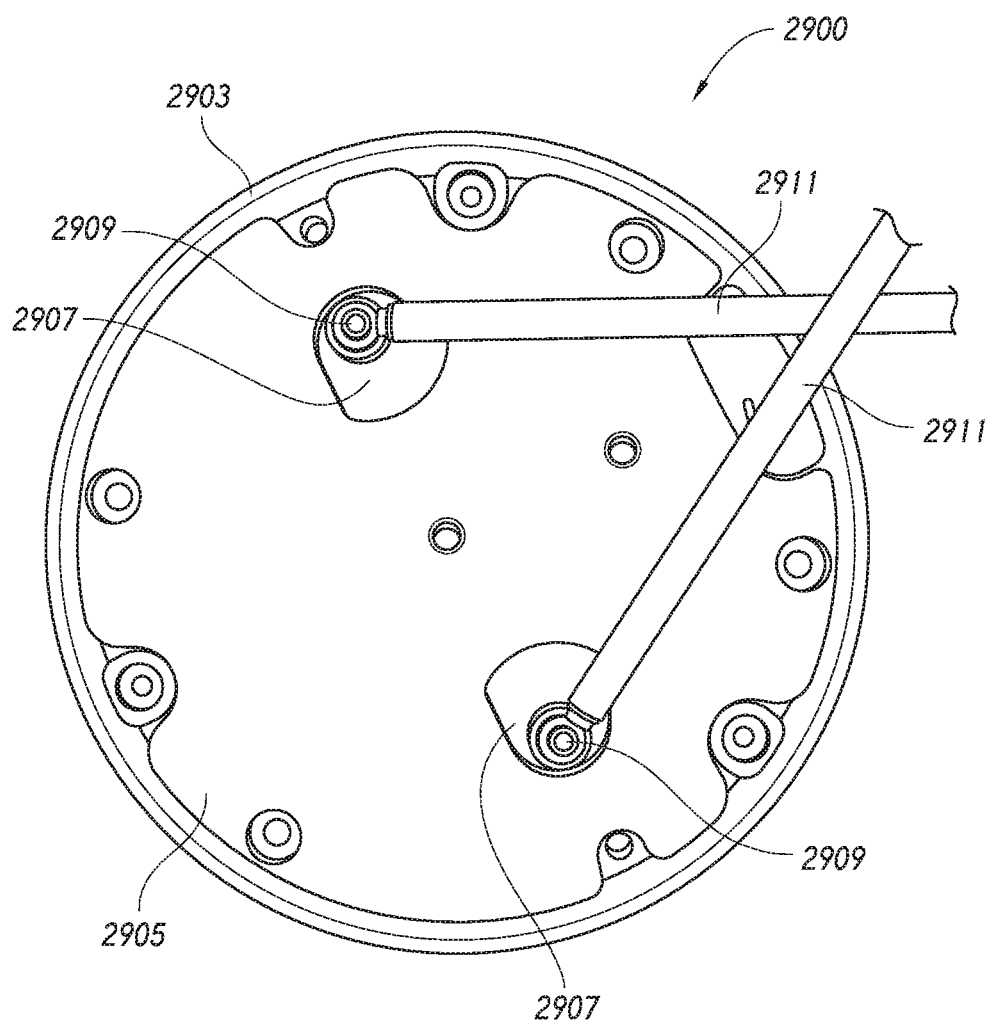
FIGS. 29A-29M illustrate a heater plate system having increased power due at least in part to an increase in a filament area and/or the use of a flat filament.
Figure 29B:
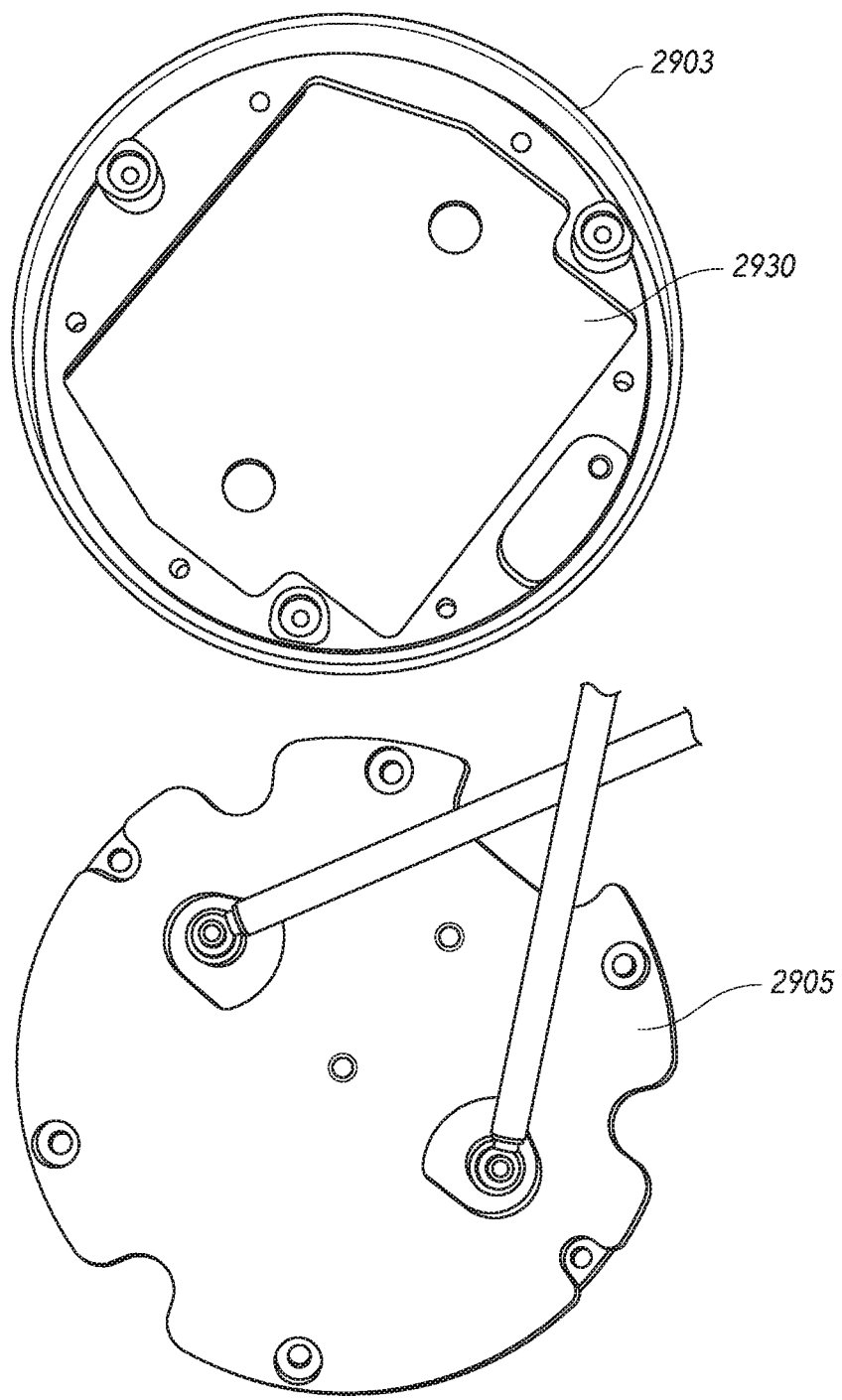
Figure 29C:
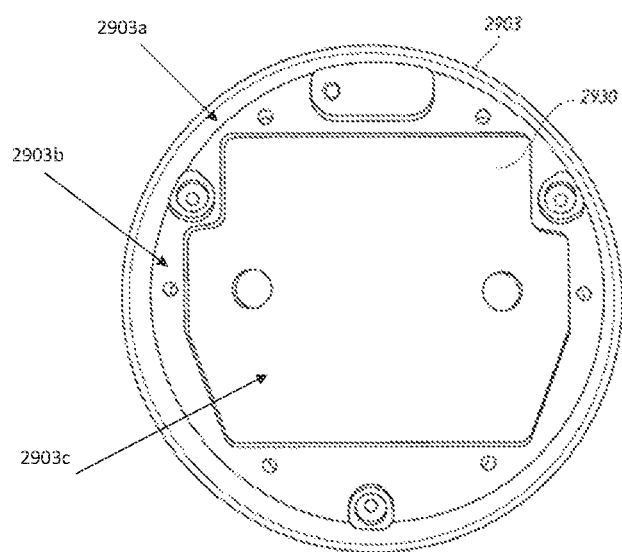
Figure 29D:
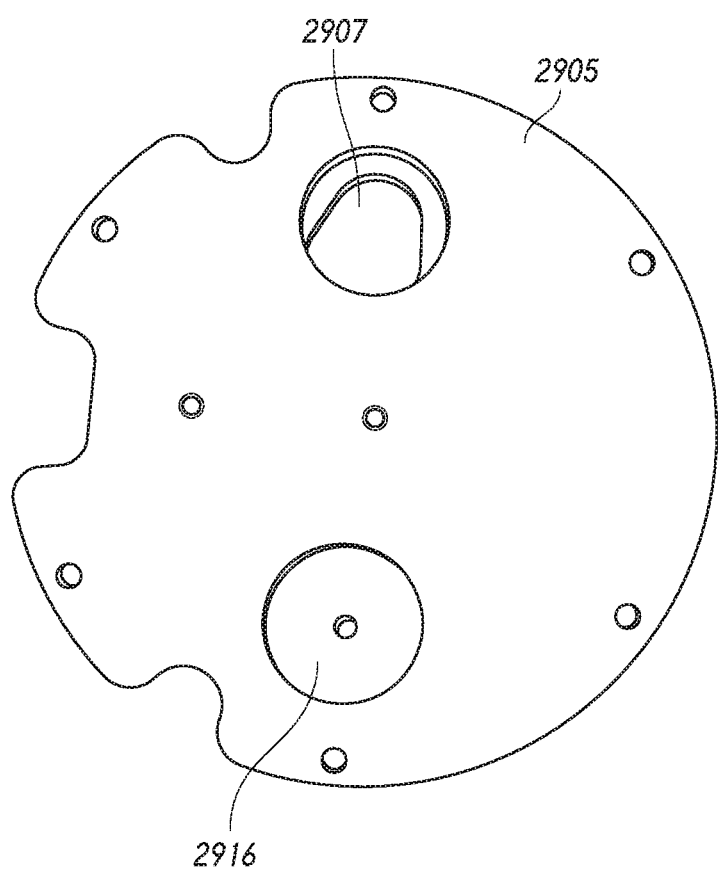
Figure 29E:
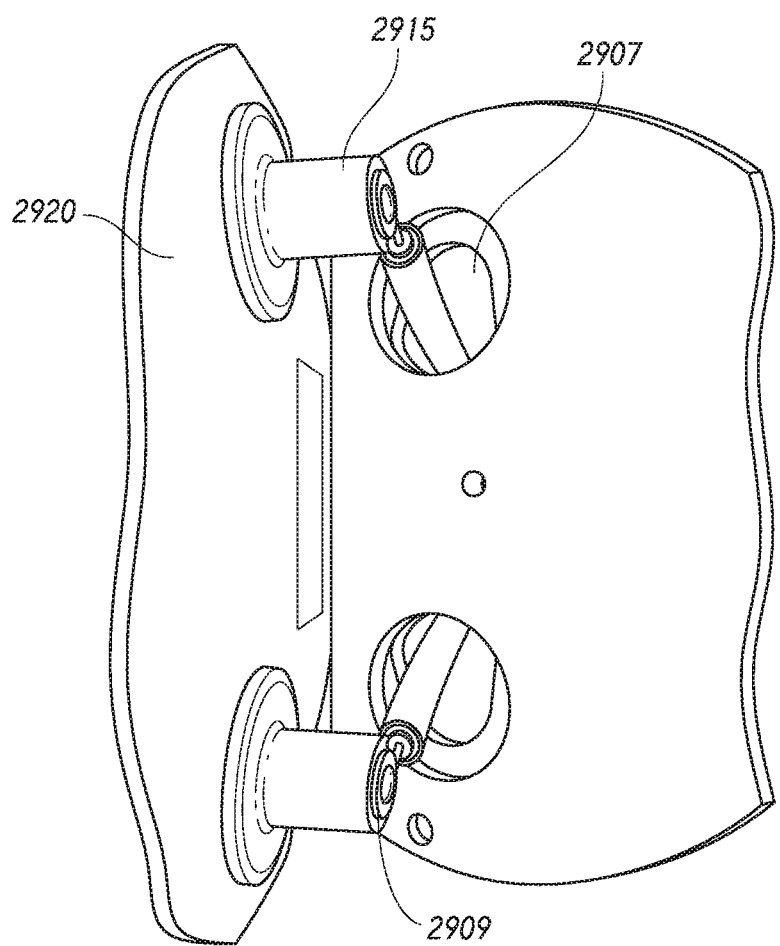
Figure 29F:
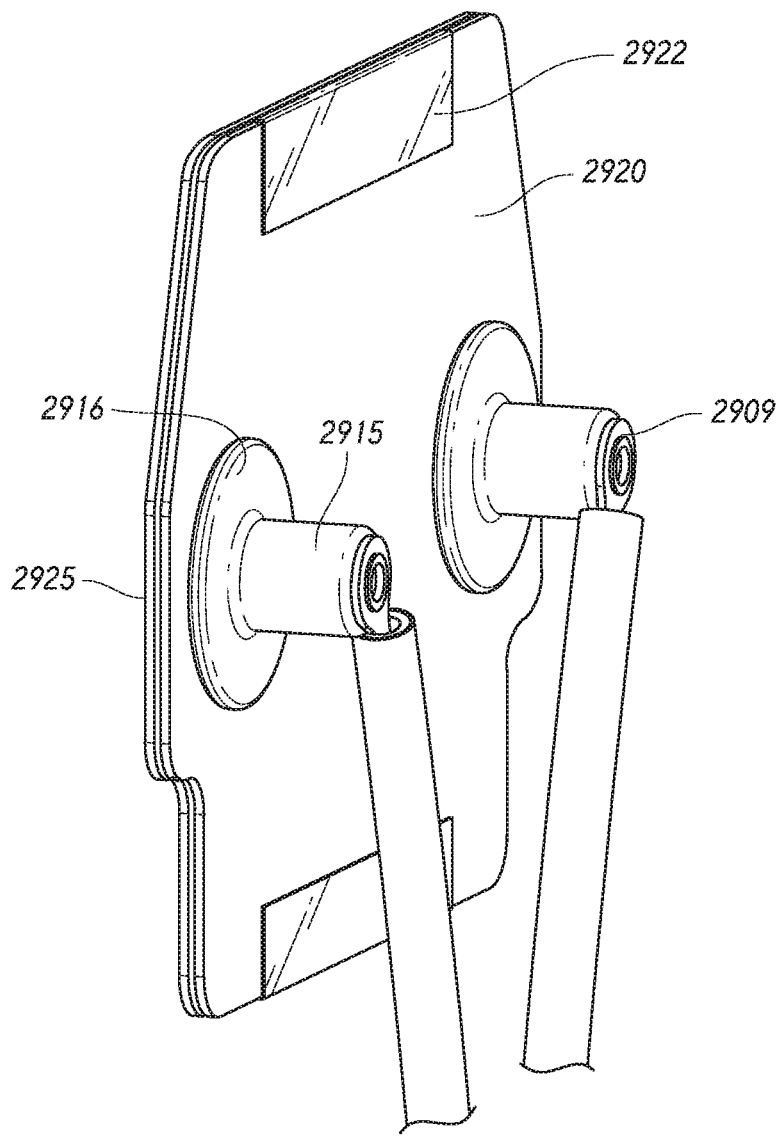
Figure 29G:
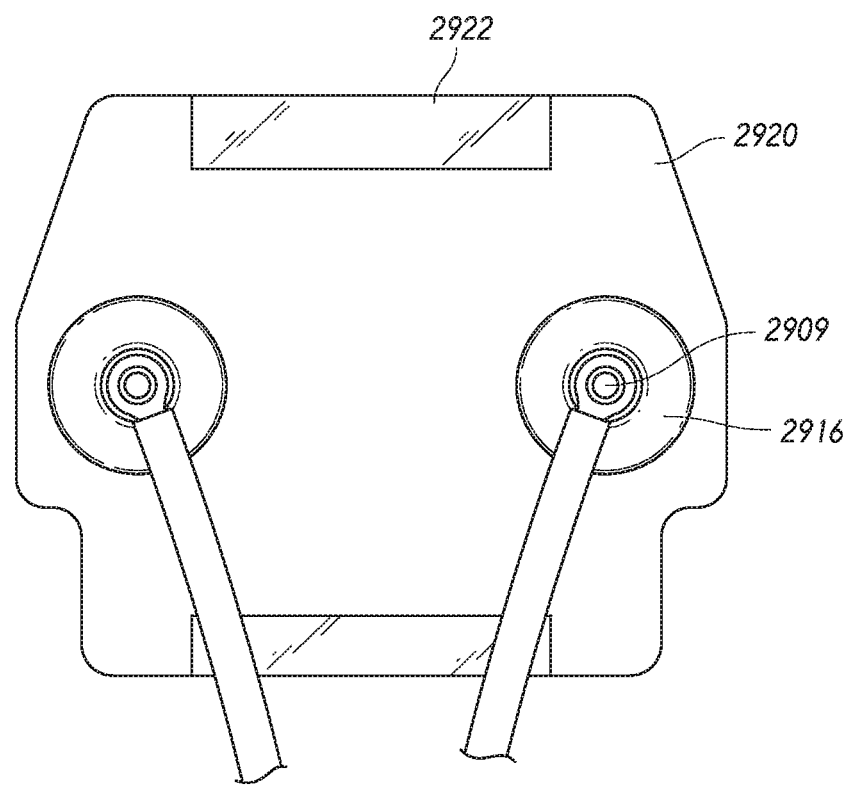
Figure 29H:
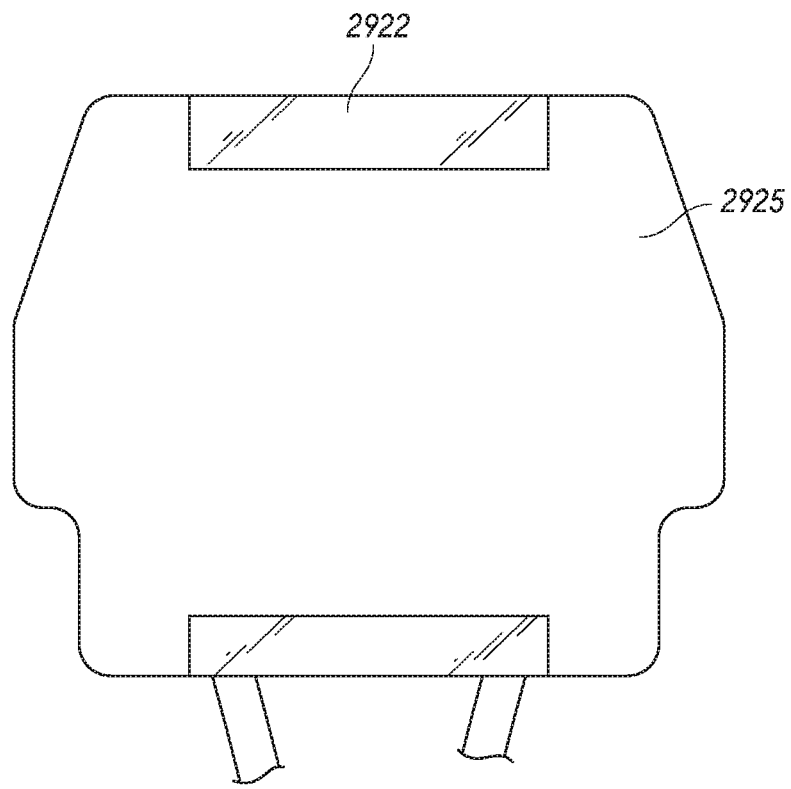
Figure 29I:
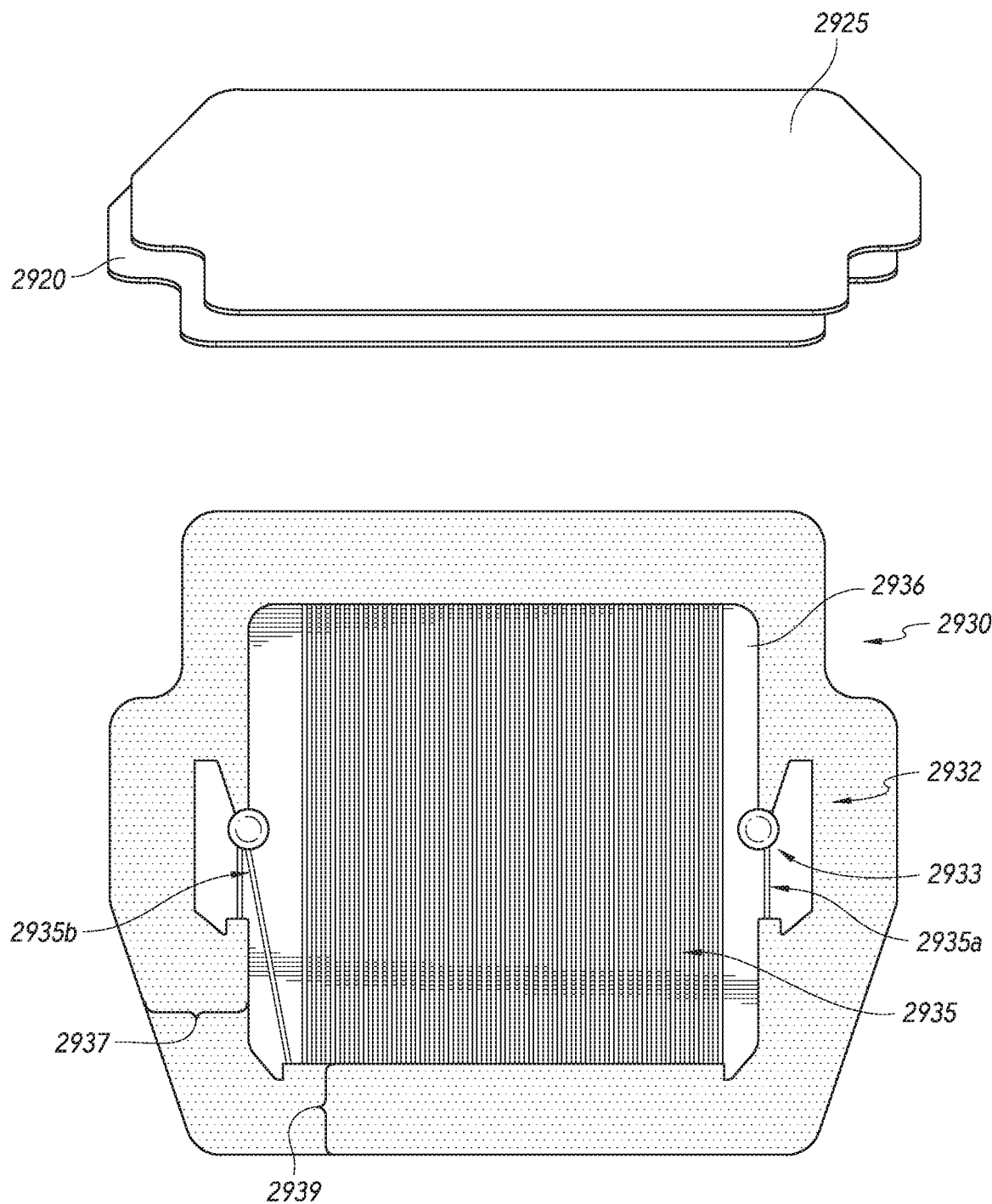
Figure 29J:
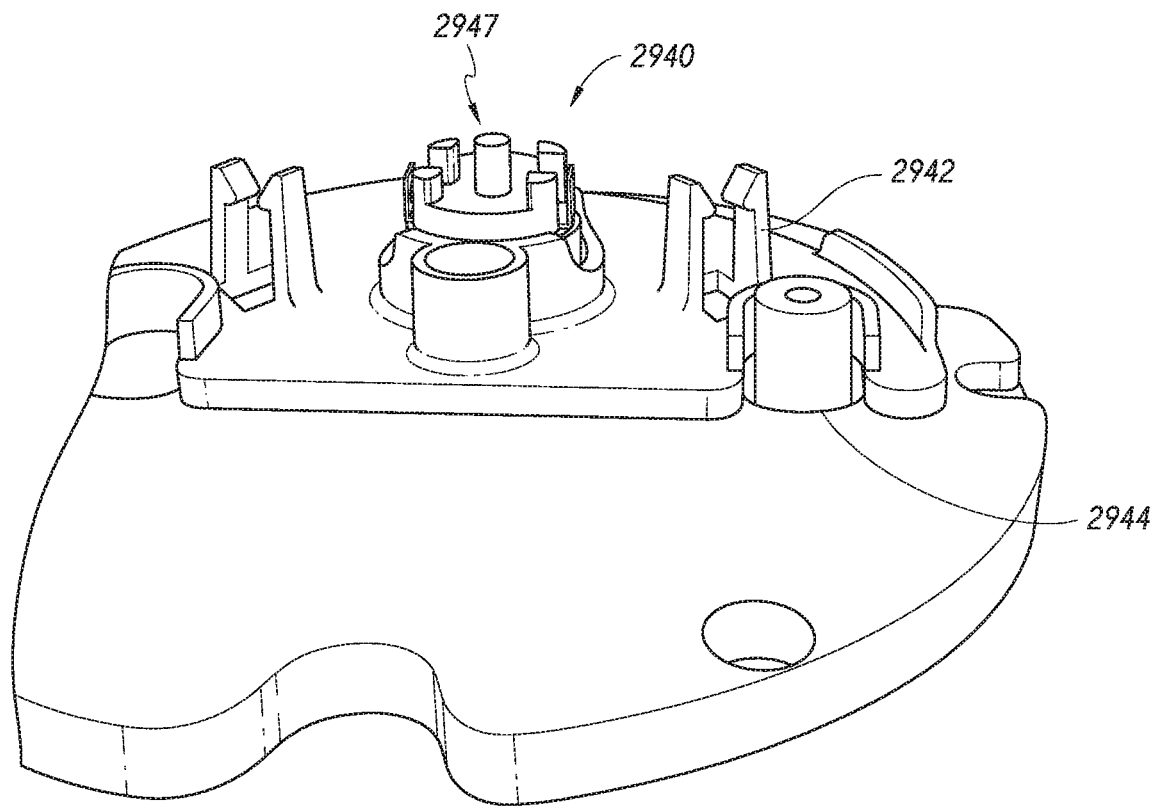
Figure 29K:
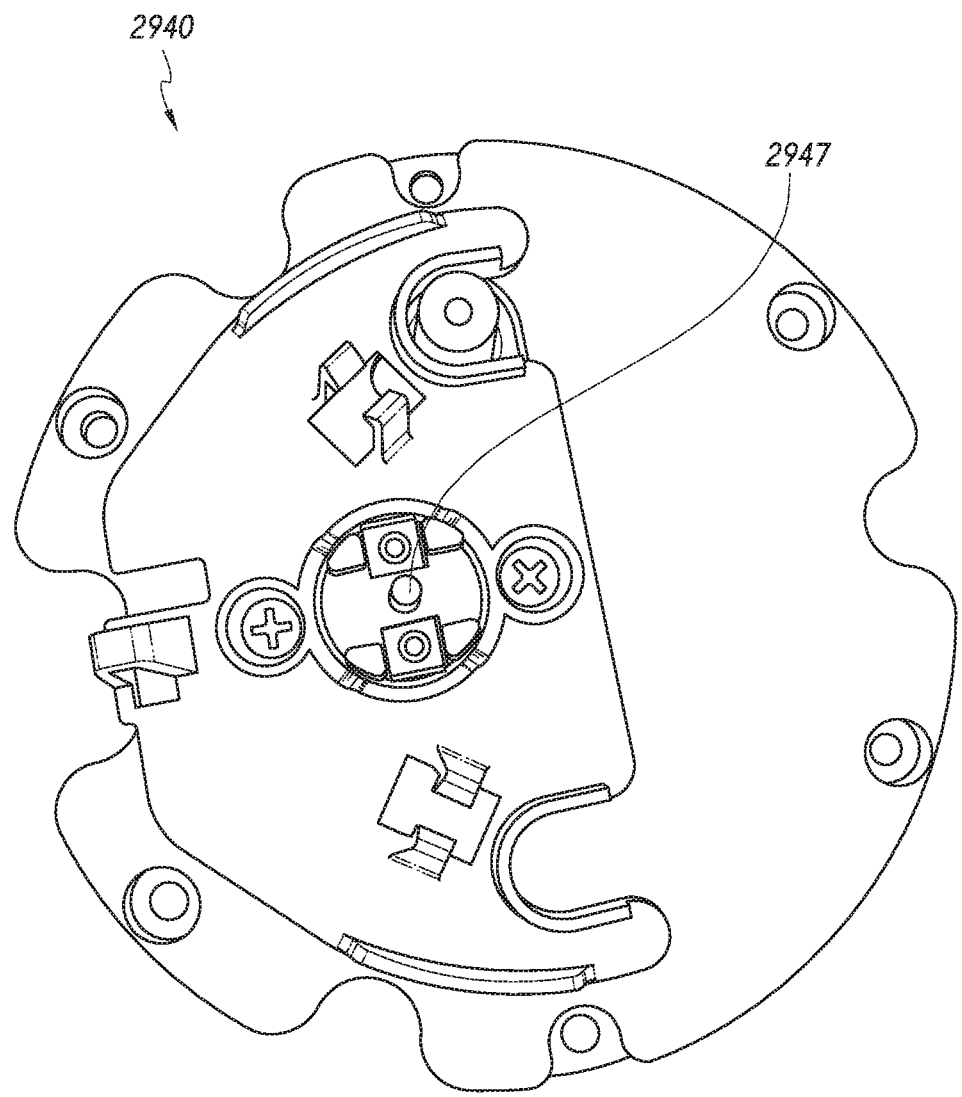
Figure 29L:
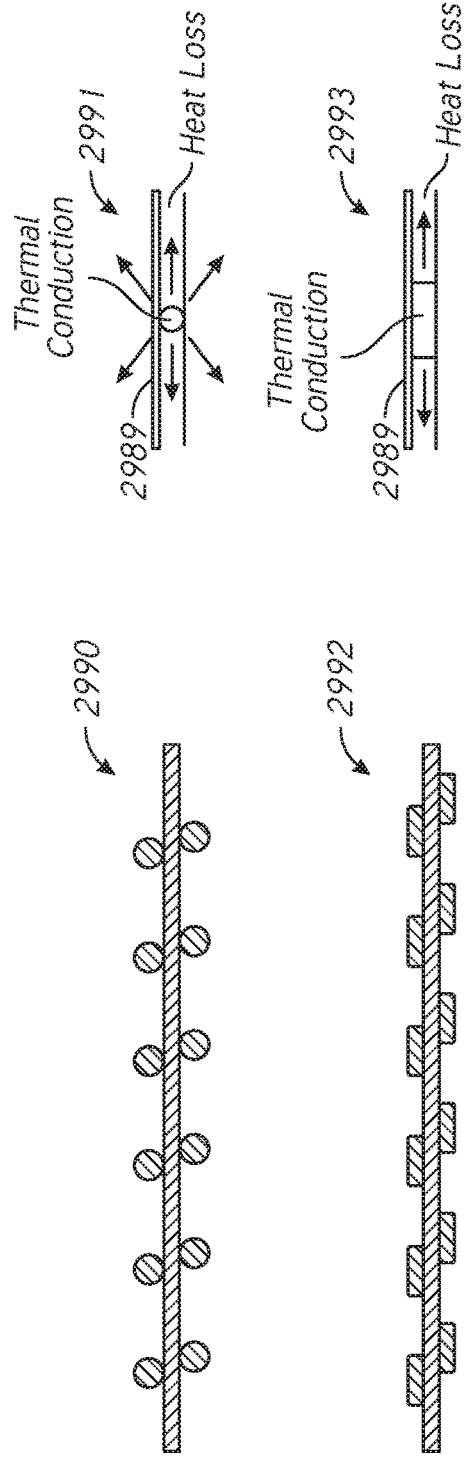
Figure 29M:
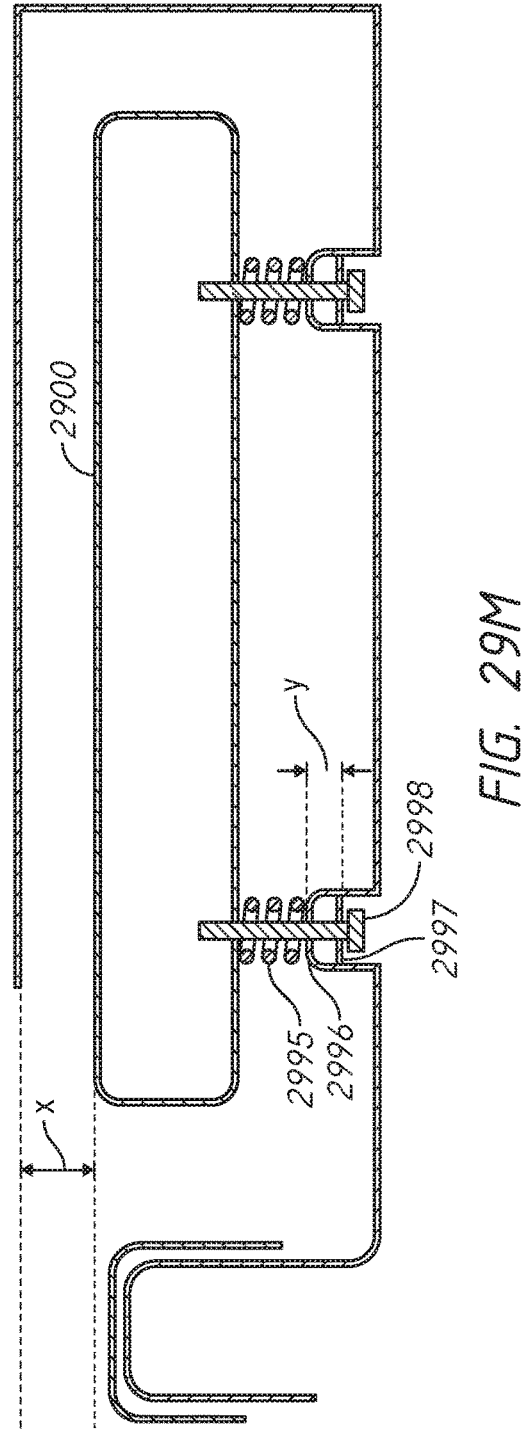

An example of a preloaded spring is shown in FIG. 29M. A spring 2995 is placed between a heater plate assembly 2900 and a spring assembly platform 2996. The spring assembly platform 2996 can be an integral member of the heater base 102 chassis or can be separate platform. A screw 2998 is inserted through the spring assembly platform 2996 and attached to the bottom of the heater plate assembly 2900. The screw 2998 is allowed to float with respect to the spring assembly platform 2996 so that it rises and falls with the heater plate assembly 2900 when the heater plate assembly 2900 is pushed down and released. In a preloaded spring system, additional material or a second platform 2997 can be added to lower the head of the screw 2998 a distance "y" and prevent the head of the screw 2998 from rising up to the spring platform 2996. Thus, the spring 2995 is held in a preloaded condition. This results in the heater plate assembly 2990 being lowered a distance "x" from its otherwise highest potential state if the spring 2995 was not preloaded.

Heater Plate Assembly

An embodiment of the heater plate assembly 2900 is shown in FIGS. 29A-K. The heater plate assembly 2900 can comprise a heater plate 2903. The heater plate 2903 may be at least partially exposed to ambient when not in use. For example, the heater plate 2903 may be at least partially exposed to ambient when a humidification chamber is not inserted into the gases humidification system, or the heater plate 2903 may be at least partially exposed to a user when a humidification chamber is not inserted into the gases humidification system. The heater plate 2903 may be made from a thermally conductive material. In some embodiments the thermally conductive material may be a metallic material.

The heater plate assembly 2900 can comprise the heater plate 2903, a heating element 2930, one or more layers of insulation comprising, for example, a back plate set 2920 and a heater plate set 2925, a back plate 2905, and at least two wires 2911. The heater plate comprises a first surface 2903a at a periphery of the heater plate, a second surface 2903b at least partially surrounded by the first surface, and a recess 2903c defined within the second surface that is recessed relative to the first surface and the second surface, the recess configured to receive the heating element therein. A back plate set 2920 as herein described refers to at least one or more layers of insulation located between the back plate 2905 and the heating element 2930. The heater plate set 2925 as herein described refers to at least one or more layers of insulation located between the heating element 2930 and the heater plate 2903. In some embodiments the heater plate assembly 2900 can include at least one insulatory piece 2915. In some embodiments the at least one insulatory piece 2915 can include two, or more than two, insulatory pieces. Each of the at least one insulatory piece 2915 may be defined as a component that provides electrical insulation and may be located around the connection between one of the at least two wires 2911 and the heating element 2930. The heater plate assembly 2900 is clamped to prevent unwanted liquid entry into the heater plate assembly 2900 which could cause a short. In an embodiment, the heater plate assembly 2900 is clamped to prevent liquid entry to the International Protection Marking IP Code IPX2 standard.

The at least two wires 2911 connect a power source to the heating element 2930. The heating element 2930 may be an element that provides a required electrical resistance, such as a metallic element or carbon element. In some cases the heating element 2930 may be a nichrome heating element as shown in FIG. 29I.

The heating element 2930 comprises a flat filament 2935 wound around a non-conductive core 2936, such as mica, ceramic, or other heat tolerant non-conductive material. The flat filament 2935 can be made from nickel chromium alloy or other material with similar electrical and mechanical properties. The flat filament 2935 provides greater surface area, which allows for better heat transfer and better reduction in hot spots, than a round shaped filament. This is shown, for example, in FIG. 29L. A cross section of a round filament 2990 is illustrated. As shown in the illustration 2991, the round filament 2990 provides little conductive contact with a heater plate 2989 and thus loses substantial heat through radiative heat loss. A cross section of a flat filament 2992 is also illustrated. The illustration 2993 illustrates how the flat filament 2992 is in greater conductive contact with the heater plate 2989 than the round filament 2990 and thus has lower radiative heat loss. As a result, a flat filament can operate at a lower temperature, but provide similar heating capabilities as a round filament running at a higher temperature. Thus, a flat filament runs cooler than a similar performing round shaped filament. In a 200W embodiment, a flat filament can run at a temperature that is about 125 degrees Celsius lower than a similarly performing round filament. This will help prolong the life of the heating element 2930. Similarly, because there is significantly less radiative heat loss, the back plate 2905 is kept at a cooler temperature. In some embodiments, the back plate 2905 can be 20-30 degrees Celsius lower using a flat filament than using a round filament. The lower temperature of the back plate 2905 provides an overall cooler operating and more efficient performing device.

The flat filament 2935 is configured such that a small gap separates each winding of the flat filament 2935 in order to avoid shorting the flat filament 2935. In an embodiment, the gap is about 0.3 mm. This gap is smaller than the comparable gap used for a similar performing round shaped filament, because windings of a flat filament are less likely to move closer together. The smaller gap permits a higher density of windings, which allows the heating element 2930 to have an increased thermal efficiency compared to heating elements using similar performing round shaped filament. This allows the heater plate assembly 2900 to supply sufficient energy to significantly increase humidity levels at higher air flow rates. For example, in an embodiment, the power increase is sufficient to supply sufficient energy to heat about 80 liters per minute (Lpm) at 37 degrees Celsius and about 120 Lpm at 31 degrees Celsius.

The flat filament ends 2935a, 2935b are electrically connected to electrical connectors 2933. The electrical connectors 2933 are in electrical communication with the at least two wires 2911 to power the flat filament 2935.

The heating element 2930 also comprises an insulation layer 2932 surrounding the conductive parts of the heating element 2930. The insulation layer 2932 forms part of at least a 0.4 mm layer of insulation. In an embodiment, two layers of 0.2 mm insulation are provided. In an embodiment, 0.8 mm of insulation is provided, comprising one or more layers. Redundant insulation layers provide a fallback in case one layer of insulation fails. The insulation layer 2932 forms a perimeter 2937, 2939 surrounding the heating element 2930. In some embodiments the perimeter 2937, 2939 may be approximately 0.8 mm to approximately 0.9 mm. The perimeter 2937, 2939 may contribute to providing a double insulated system.

The at least one insulatory piece 2915 may insulate the at least two wires 2911 from the back plate 2905. Thus, the at least one insulatory piece 2915 may be located at the connection of the at least two wires 2911 to the heating element 2930. In some embodiments the at least one insulatory piece 2915 may be located such that it surrounds the connection of the at least two wires 2911 to the heating element 2930. The at least two wires 2911 may extend from the centre of the at least one insulatory piece 2915. The at least two wires 2911 may be restrained by a restraining member 2940 as in FIGS. 29J and 29K. The restraining member 2940 is described in more detail below. The at least two wires 2911 may be within at least one electrically insulating sleeve. In some embodiments the at least two wires 2911 may each be contained in a separate electrically insulating sleeve.

The at least one insulatory piece 2915 may be made from a ceramic material. In some embodiments other materials may be used for the at least one insulatory piece 2915. The at least one insulatory piece 2915 may be clamped to one or more of the layers of insulation within the back plate set 2920. The back plate 2905 may be applied onto the back plate set 2925. The back plate 2905 may provide pressure to the at least one insulatory piece 2915. Thus, the at least one insulatory piece 2915 may provide pressure to the back plate set 2920. The pressure applied to the back plate set 2920 holds the heating element 2930 nearer to the heater plate 2903. The increased clamping allowed by the present design allows the heater plate assembly 2900 to run cooler overall and reduces hot spots.

The at least one insulatory piece 2915 may include a flange 2916. The flange 2916 fills at least one opening 2907 on the back plate 2905 as shown in FIG. 29D. FIG. 29E shows an embodiment where the at least one insulatory piece 2915 may have a T-shape when viewed from the side, top, or bottom. In some embodiments the at least one insulatory piece 2915 may have a triangular shape, a cone shape, or another shape which incorporates a flange or taper. The at least one opening 2907 on the back plate 2905 may be shaped in different ways. For example, the at least one opening 2907 can incorporate a tear-drop shape as shown in FIG. 29D. This allows the at least one insulatory piece 2915 to fit through the at least one opening 2907 during manufacture or during maintenance, yet still maximize the clamp bush. The at least one insulatory piece 2915 is securely held in place by the flange 2916. The tear-drop shape of the at least one opening 2907 allows the at least one insulatory piece 2915 to fit through the at least one opening 2907 even while connected to the at least two wires 2911. The at least one opening 2907 can also be triangular, rectangular, circular or square or any other shape that will allow the at least one insulatory piece 2915 to fit through the at least one opening 2907 while still connected to the at least two wires 2911. The at least one opening 2907 may be used to maintain a minimum clearance distance between the at least two wires 2911, rivets 2909, and the back plate 2905. In some embodiments a minimum clearance distance between the at least two wires 2911, the rivets 2909, and the back plate 2905 may be approximately 8 mm along a surface and/or 5 mm through air. This may provide two different forms of safety.

In an embodiment where the at least one insulatory piece 2915 comprises the flange 2916, the at least one insulatory piece 2915 may maintain a minimum clearance between the at least two wires 2911 and the back plate 2905. The shape of the at least one insulatory piece 2915 may provide a minimum clearance distance between the at least two wires 2911 and the back plate 2905. The flange 2916 may be clamped to the back plate set 2920 which may push the heating element 2930 nearer to the heater plate 2903. This may provide improved contact between the heating element 2930 and the heater plate 2903. Good contact between the heating element 2930 and the heater plate 2903 may provide more even and reliable heating. Good contact between the heating element 2930 and the heater plate 2903 may reduce the formation of hot spots, which may prolong the life of the heating element 2930.

The multiple layers of insulation 2920, 2925 may be located near the heating element 2930. Each of the multiple layers of insulation 2920, 2925 may provide electrical insulation and thermal conduction. The multiple layers of insulation 2920, 2925 may improve the safety of the electrical system. In some embodiments the multiple layers of insulation 2920, 2925 may be made from mica sheets. In other embodiments the multiple layers of insulation 2920, 2925 may be made from other sheet electrical insulators such as silicon, polyether ether ketone (PEEK) or polyimide (for example, Kapton, a registered trademark of E. I. du Pont de Nemours and Co.). If one or more of the multiple layers of insulation 2920, 2925 is too thick, it may compromise heat transfer; if one or more of the multiple layers of insulation 2920, 2925 is too thin, it may become fragile during manufacture. A thick layer of the multiple layers of insulation 2920, 2925 may provide a useful surface for clamping the at least one insulatory piece 2915, but a thin layer may provide better heat transfer.

The multiple layers of insulation 2920, 2925 may comprise one or more layers of insulation of the same thickness, or alternatively of different thicknesses, wherein some of the one or more layers of insulation may be thicker than others. For example, one or more of the layers of insulation may be greater than approximately 0.4 mm thick and others may be less than approximately 0.4 mm thick.

In some embodiments the thickness of the back plate set 2920, as an aggregate, may vary from the thickness of the heater plate set 2925, as an aggregate. In some embodiments the back plate set 2920 may have a greater aggregate thickness than the heater plate set 2925, which may encourage greater thermal conduction of the generated heat to the heater plate 2903. For example, the back plate set 2920 may have a thickness of approximately 0.8 mm and the heater plate set 2925 may have a thickness of approximately 0.4 mm. There may be a range of different thicknesses that would provide good reliability and performance characteristics. In some embodiments the back plate set 2920 and the heater plate set 2925 can each include a plurality of the layers of insulation. In some embodiments the number of the layers of insulation may differ between the back plate set 2920 and the heater plate set 2925. For example, the heater plate set 2925 can include one layer of insulation, and the back plate set 2920 can include two layers of insulation.

In some embodiments, the back plate set 2920 and the heater plate set 2925 can include a single layer of insulation; this single layer may provide a reliable product at lower voltages. In some embodiments the back plate set 2920 and the heater plate set 2925 can each include multiple layers of insulation. In one example, the back plate set can include two layers of insulation, each approximately 0.4 mm thick, and the heater plate set 2925 can include two layers of insulation, each approximately 0.2 mm thick. Any combination of numbers of layers of insulation either side of the heating element 2930 also fall within the scope of the disclosure. The insulation sets 2920 and 2925 can be held together using, for example, thermally resistive tape 2922 placed on two opposites sides to create a clamping effect. These examples are meant to be illustrative only and are in no way limiting. It is to be understood that any combinations of the above embodiments may also fall within the scope of the disclosure.

An electrical component is described herein as having double insulation if it has two forms, layers, or components of insulation in any one plane. The heater plate assembly 2900 described in the present specification has features which may provide double insulation. These features may include the insulation layer 2932, the at least one insulatory piece 2915, the at least one opening 2907, and/or the insulation provided by the back plate set 2920 and the heater plate set 2925.

FIGS. 29J and 29K illustrate the restraining member 2940. In some embodiments, the restraining member 2940 is configured to restrain the at least two wires 2911. At least one restraining mechanism 2942 may be located on the restraining member 2940 to restrain the at least two wires 2911. The at least one restraining mechanism 2942 may be any mechanism arranged to hold or restrain a wire, such as a loop for a cable tie, a snap fit mechanism, a hinge mechanism, or the like. The restraining member 2940 may prevent the at least two wires 2911 from touching the back plate 2905. The restraining member 2940 may be located on the back plate 2905 and may have at least one recess 2944 to complement the at least one insulatory piece 2915.

A thermal cut out reset switch 2947 protrudes from the restraining member 2940. When the heater plate temperature goes over a set temperature, a button portion of the thermal cut out reset switch 2947 clicks out and power from the mains input (not shown) to the heater plate assembly 2900 is disconnected. The thermal cut out reset switch 2947 is located for easy access to allow a user to quickly reset the power connection to the heater plate assembly 2900.

The heater plate assembly 2900 as described throughout this specification should not be limited to a respiratory application but may be used in any application that requires a heating assembly.

Guard

In some embodiments, a guard 107 extends along a front portion of the base portion 202 of the heater base 102 and the rim edge 172. The guard 107 can be depressed to enable the base 105 and the lip 205 of the chamber 104 to access the heater plate 108 and the groove 178 (in embodiments that include the groove 178). The guard 107 can be allowed to revert to a non-depressed position once the chamber 104 has been installed. In the non-depressed position, the guard 107 retains the chamber 104 against inadvertent removal from or movement relative to the heater base 102.

In some such embodiments, the heater base 102 includes an anti-racking mechanism that cooperates with the guard 107. The anti-racking mechanism allows the guard 107 to translate generally vertically without significant movement of one end of the guard 107 relative to the other end of the guard 107 even when only one end of the guard 107 is depressed. In other words, the anti-racking mechanism cooperates with the guard 107 to cause vertical movement of the first end to translate into coordinated vertical movement of the second end.

With reference now to FIG. 10, in the illustrated configuration, a torsion bar 109 can be operatively coupled to the guard 107. The guard 107 can include two posts 110. The posts 110 can extend downward from the guard 107. In some configurations, the inner chassis 174 can include guides 111 that receive at least a portion of the posts 110. In the illustrated configuration, the guides 111 define passages that receive the posts 110. The guides 111 help reduce the ability of the posts 110 to tilt during axial translation relative to the guides 111.

Figure 11:
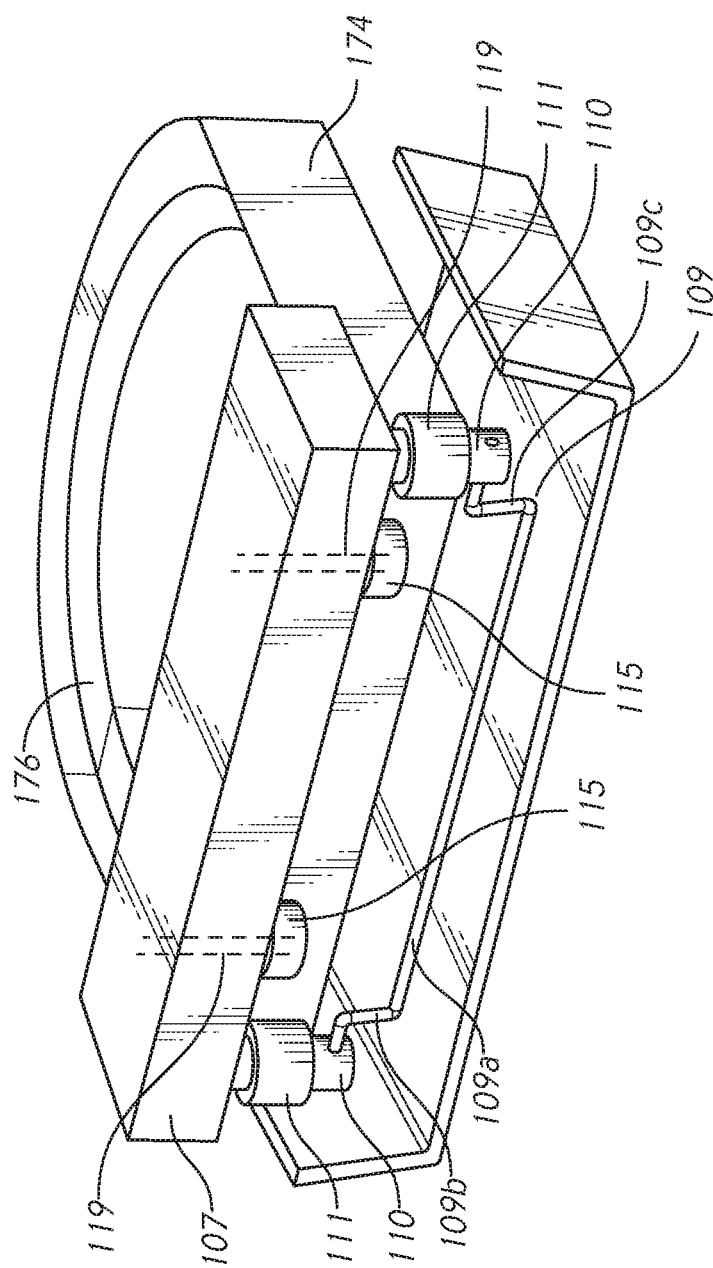
FIG. 11 is a partially deconstructed view of the heater base of FIGS. 2-8.

As shown in FIG. 10 and FIG. 11, the torsion bar 109 includes an elongated central portion 109a that extends between a pair of arms 109b, 109c. The elongated central portion 109a can be mounted for rotation relative to the inner chassis 174. In some configurations, the elongated central portion 109a can be captured between a portion of the inner chassis 174 and another inner surface 139 of the heater base 102. The elongated central portion 109a is capable of relatively free rotation relative to the inner chassis 174.

The arms 109b, 109c extend generally perpendicularly from ends of the bar 109a. One arm 109a is coupled to the guard 107 near a first end of the guard 107, and the other arm 109b is coupled to the guard 107 near the other end of the guard 107. In the illustrated configuration, the arms 109b, 109c are joined to the distal ends of the posts 110. As such, the arms 109b, 109c help to coordinate movement of the posts 110. Thus, the use of the torsion bar 109 connected to the guard 107 helps to reduce the ability of the guard 107 to twist about a generally horizontal axis "A" that extends through the guard 107 such that a generally vertical plane extending through the axis "A" substantially bisects the guard 107 into a first half and a second half.

The guard 107 translates axially relative to the inner chassis 174. To return the guard 107 to the non-depressed position, biasing members 113 can be positioned between at least a portion of the guard 107 and the inner chassis 174. In the illustrated configuration, the inner chassis 174 can include mounts 115 while the guard 107 includes supports 119. The biasing members 113 can be springs that are positioned between the mounts 115 and the supports 119. The biasing members 113 urge the guard 107 away from the inner chassis 174 or other relatively stationary portion of the heater base 102. In some configurations, the torsion bar 109 can be biased instead of, or in addition to, the guard being biased relative to the inner chassis 174.

The illustrated guard 107 also comprises a catch 129. The catch 129 is received within a portion of the heater base 102 and secures the guard 107 against removal from the heater base 102 unless removal is desired for servicing or repair, for example but without limitation. In the illustrated configuration, the catch 129 can comprise a forked component with outwardly extending tabs at the distal ends. Other configurations are possible keeping in mind the desire to allow relatively free movement within a range of motion and then restraint against further movement.

In use, if a user depresses the guard 107 near one end, the torsion bar 109 causes the other end of the guard 107 to depress as well. The torsion bar 109 causes the guard 107 to depress more evenly across its length. This advantageously allows the user to insert and remove the chamber 104 more easily. In addition, because a user can depress one side or the other of the guard 107 (as indicated by markings 106) yet cause the length of the guard 107 to translate downward, the anti-racking feature reduces the risk of catching a finger between the guard 107 and the base housing.

Cartridge

The heater base 102 can include a sensor cartridge 300 extending outward from the front surface 146 of the spine portion 210. In some embodiments, the sensor cartridge 300 is permanently coupled to or integrally formed with the spine portion 210. In some embodiments, as shown in FIG. 4, a top surface 345 of the sensor cartridge 300 slopes downward from the back to the front of the cartridge 300.

Figure 7:
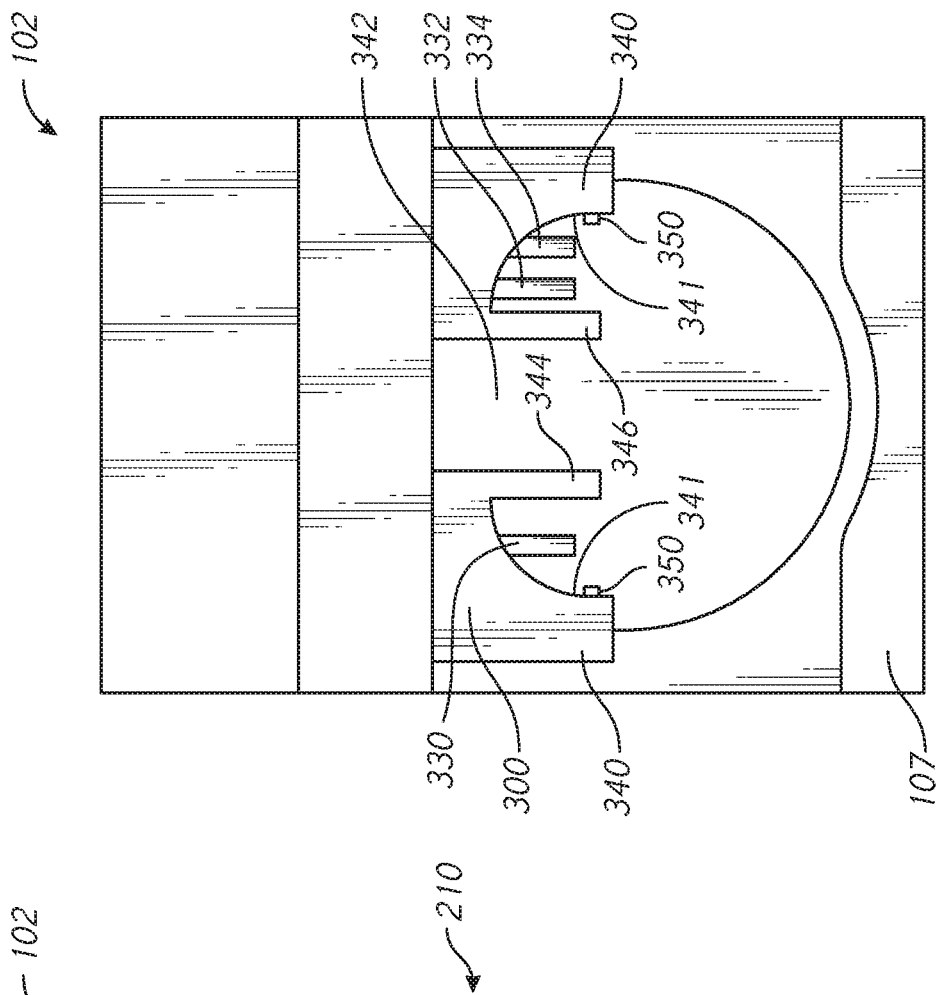

The cartridge 300 can include or support various sensor probes. Any suitable components can be used as the sensors. For example, thermocouples, resistance temperature detectors, fixed resistors and the like can be used as the sensors. In some embodiments, for example as shown in FIG. 7, the cartridge 300 includes probes 330, 332, 334 extending from the cartridge 300 and having thermistors at the tips. In some such embodiments, the probes can be overmolded with a thermally conductive polymer. For example, the probes can have a skin made of a high temperature polymer with a highly conductive polymer section at and near the thermistor tip. The skin can advantageously help increase the surface area of the sensing portion of the probes exposed to air flow and help provide additional protection to the sensors.

In the embodiment illustrated in FIG. 7, the cartridge 300 includes the first sensor probe 330 positioned on one side of the cartridge 300 and the second and third sensor probes 332, 334 positioned on the other side of the cartridge 300. The sensor probes can have a length sufficient to position the thermistors near the center of the gas flow path through the port.

In some configurations, the first sensor probe comprises a thermistor that can be configured to sense temperatures of gas flow. In some configurations, the second and third sensor probes comprise thermistors that can be configured to sense gases flow rate using a temperature-based flow measurement approach. Other configurations can have any combination of temperature and flow sensors located in various locations as would be understood by a person of skill in the art from the present disclosure. In this approach, one of the thermistors functions as a reference sensor that measures the flow temperature at the sensing location and the other thermistor, which can be a heated thermistor, is heated to a preset temperature differential above the flow temperature. In some embodiments, the heated thermistor is heated to a set temperature, such as, for example, 160 degrees Celsius. In some applications, a resistor can be used to heat the thermistor instead of using a heated thermistor. In some configurations, all of the thermistors can be both heated and non-heated thermistors. Flow velocity can be determined using the measured flow temperature, the known heat transfer characteristics of the heated thermistor and the power consumed to maintain the temperature difference between the second and third thermistors. Other techniques also can be used. For example but without limitation, constant power can be provided to the thermistors and the heat conducted into a nearby thermistor can be used to determine the rate of flow.

Figure 3:
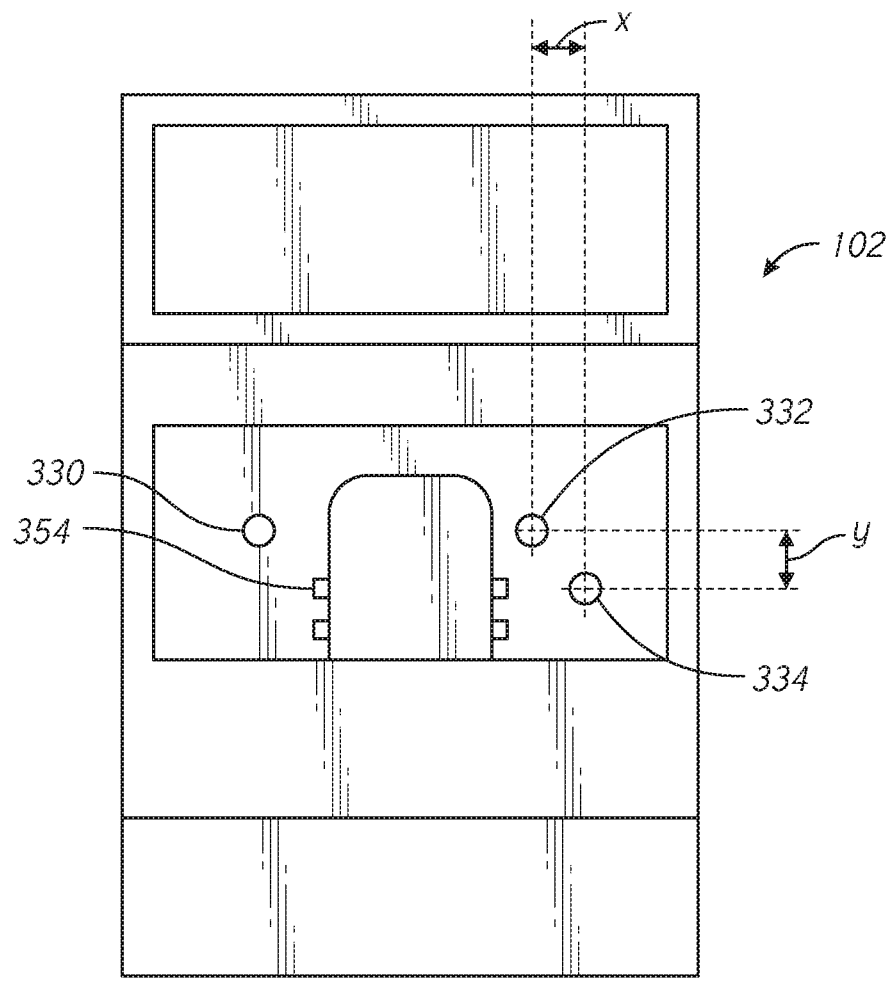
Figure 5:
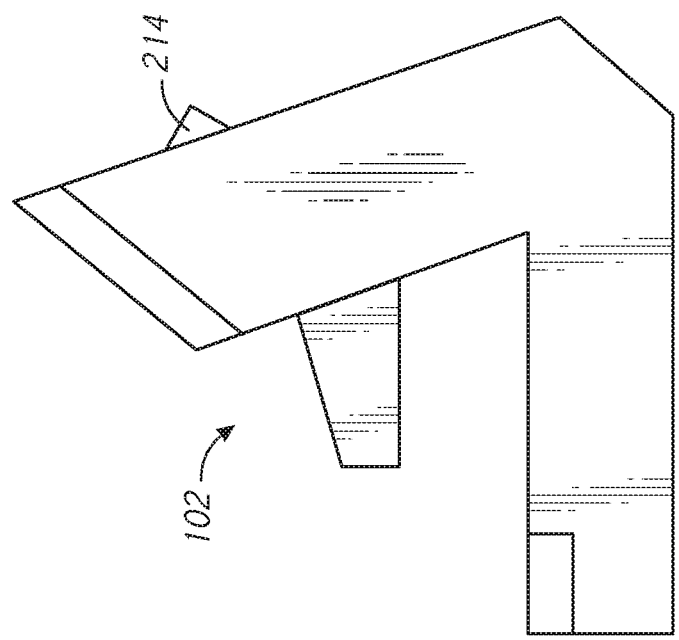

With reference to FIG. 3, the thermistors of the second and third sensor probes 332, 334 are spaced apart in both the X direction and the Y direction by about 7 mm. The thermistors of the second and third sensor probes 332, 334 can be spaced far enough apart to reduce or eliminate the likelihood of heat contamination between the two. At the same time, the thermistors of the second and third sensor probes 332, 334 can be placed close enough together to maintain proximity to the center of flow. If the thermistors of the sensor probes 332, 334 are placed too far away from the center of flow (for example, close to the port wall), the thermistors of the sensor probes 332, 334 can be affected by wall effects, boundary layer effects, and other factors that may reduce the accuracy of the thermistors.

In the illustrated embodiment, the first sensor probe 330 is positioned vertically higher than the second and third sensor probes 332, 334. The height of the sensor can advantageously allow for sensing the temperature of the gases closer to the beginning of the heated part of the inspiratory conduit 120. In some applications, this can allow for more accurate sensing of the temperature of gases flowing through the inspiratory conduit 120.

Cartridge and Chamber Coupling

The sensor cartridge 300 and a top of the humidification chamber 104 have a coupling configuration. The coupling configuration can promote correct and easy installation of the chamber 104.

As shown in FIG. 7, the cartridge 300 includes outer sidewalls 340 extending beyond the tips of the sensor probes 330, 332, 334. The cartridge 300 also includes a central channel 342. In the illustrated configuration, the central channel is defined by fins 344, 346 that extend forward from each side of the central channel 342 generally parallel to the sidewalls 340. A recessed portion is formed between each sidewall 340 and the neighboring fin 344, 346. The sensor probes 330, 332, 334 are positioned in these recessed portions.

In some embodiments, the cartridge 300 includes clips 350 configured to engage and secure the chamber 104. As shown in FIG. 7, the clips 350 can be located on inner surfaces 341 of the sidewalls 340. The body 103 of the chamber 104 includes corresponding recesses 450, shown in FIG. 13. The recesses 450 are configured to receive the clips 350 when the chamber 104 is installed on the heater base 102. The sidewalls 340 can allow for some degree of flexion. For example, the sidewalls 340 can flex outward as the chamber 104 is being inserted and the clips 350 slide along outer walls of the chamber 104. The sidewalls 340 then revert back to a relaxed state when the clips 350 are received in the recess 450. In some configurations, the clips 350 simply deflect relative to the sidewalls 340. In other words, the clips 350 can be configured on cantilevered members that deflect outward as the chamber 104 passes between the clips 350 until the clips 350 locate within the recesses 450 of the chamber 104.

In an embodiment, the rim edge 176 is removed in order accommodate a greater variety and shape of types of the chamber 104. In such embodiments, the sensor cartridge 300 can be used to hold the chamber 104 in place while the heater plate 108 applies upward force on the chamber 104.

Figure 2:
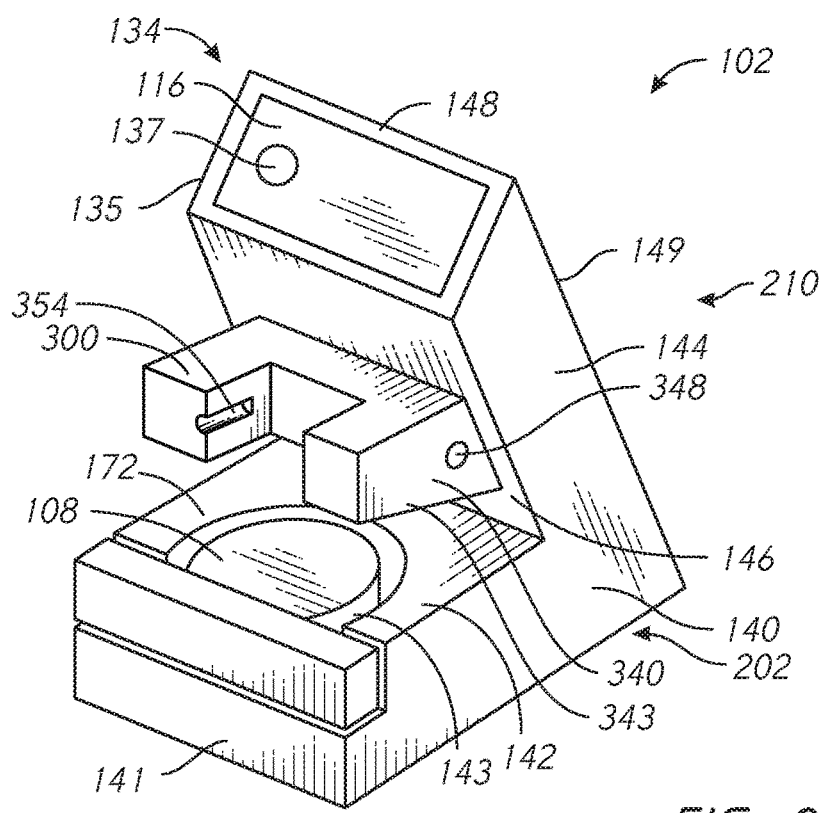
FIGS. 2-7 illustrate views of a heater base that is arranged and configured in accordance with certain features, aspects and advantages of the present disclosure.

In some embodiments, the cartridge 300 also includes a socket 348. In the embodiment of FIG. 2, the socket 348 is located on an outer surface 343 of one of the sidewalls 340. However, the socket 348 can be located elsewhere on the cartridge 300. The socket 348 can be configured to receive a plug or lead. For example, the socket 348 can receive a lead configured to be coupled to the inspiratory conduit 120 or an inspiratory conduit connector to provide power and/or an electrical connection to a heater wire in the inspiratory conduit 120. In some embodiments, a lead for the heater wire is permanently coupled to the socket 348. In some embodiments, the socket 348 or another socket in the cartridge 300 can provide a connection point for a heater wire in the expiratory conduit 122 and/or one or more sensors.

In some embodiments, the cartridge 300 includes a low power circuit suitable for operation of sensors electrically coupled to the low power circuit. The sensors can include temperature sensors, flow sensors, and/or other types of sensors adapted to measure gas properties. The low power circuit can be differentiated from a high power circuit that, in use, provides electrical power to one or more heaters (for example, heater wires) in the system. The sensors can be positioned at one or more locations in a breathing circuit such as, for example and without limitation, in an inspiratory conduit, an expiratory conduit, in a segmented inspiratory conduit at a connection location, at a patient end of an inspiratory conduit, at an outlet port of a chamber, at an inlet port of a chamber, or any combination of these. The low power circuit can include electrical components configured to provide electrical voltage and electrical current to one or more sensors, the sensors comprising thermistors, thermocouples, digital sensors, or any combination of these.

In some embodiments, the cartridge 300 is configured for use with a designated, defined, or particular set or type of sensors. For example, the cartridge 300 can include circuitry and electrical components configured to drive and read the sensors. In some implementations, the cartridge 300 can be configured to read a plurality of sensors by switching electrical voltage and/or current to one or more sensor circuits electrically coupled to and/or within the cartridge 300. By associating the cartridge 300 with the sensors, the system can be upgraded with relative ease by obtaining and/or incorporating new and/or upgraded sensors with corresponding low power circuitry and obtaining and/or utilizing a corresponding cartridge 300 configured for use with the upgraded sensors and corresponding low power circuit. In some implementations, the functionality of the system can be modified, updated, and/or upgraded by changing the cartridge 300 to accommodate modified, updated, and/or upgraded sensing circuitry.

In some embodiments, the system can be configured to detect when there is a likely short between the low power circuit and the high power circuit (for example, a short circuit between heater and sensor wires). In certain implementations, the high power circuit and the low power circuit receive electrical power from a common transformer, and additional circuitry rectifies and decreases (for example, using voltage regulators) the output electrical voltage of the transformer for the low power circuit. For example, the high power circuit can be configured to provide about 22 V and the low power circuit can be configured to provide about 3.3 V. Other voltages are also possible. For example, the high power circuit can provide a voltage of at least about 50 V, at least about 30 V and/or less than about 50 V, at least about 20 V and/or less than about 30 V, at least about 10 V and/or less than about 25 V. As another example, the low power circuit can provide a voltage of at least about 5 V, at least about 3 V and/or less than about 5 V, at least about 2 V and/or less than about 3.5 V, at least about 1.5 V and/or less than about 2 V. The actual voltage on the low power circuit can depend on the gas properties measured by the one or more sensors coupled to the low power circuit, for example the temperatures measured by the one or more temperature sensors coupled to the low power circuit. For example, in a low power circuit providing about 3.3 V, a thermistor measuring a temperature of about 50° C. can output a voltage of about 0 V and a thermistor measuring a temperature of about 20° C. can output a voltage of about 1.2 V.

Based at least in part on the expected range of voltages output by a sensor, the system can be configured to trigger a warning, alarm, notification, or signal (for example, for use in other parts of the system or electrical circuits) when the voltage on the low power circuit is outside of the expected range. The system can include a first comparator referenced to the output of a series of dividers electrically coupled to a transformer output configured to provide the voltage for the low power circuit. The first comparator can provide an out of range signal when the voltage exceeds the expected voltage (for example, the voltage that the comparator is configured to detect). For example, where the expected range is between 0 and 1.2 V or 1.5 V, the comparator can be configured to provide a signal indicating a possible short circuit when the voltage exceeds 1.2 V or 1.5 V. The system can include a second comparator referenced to ground and configured to provide a signal indicating a possible short circuit when the voltage is negative. The system can be configured to provide a signal indicating a potential short circuit immediately (for example, in real time or in near real time) upon detecting the voltage outside the expected range. In some implementations, the system can include logic configured to ignore the short circuit signal, to trigger a warning, and/or to turn off or decrease power to the high power circuit and/or the low power circuit.

The short circuit may occur where there is a leak of voltage from the high power circuit to the low power circuit which can increase the voltage on the low power circuit outside the expected range. Similarly, if a negatively-biased electrical voltage to be supplied to the high power circuit leaks to the low power circuit, the voltage on the low power circuit may become negative.

Chamber

Figure 12:
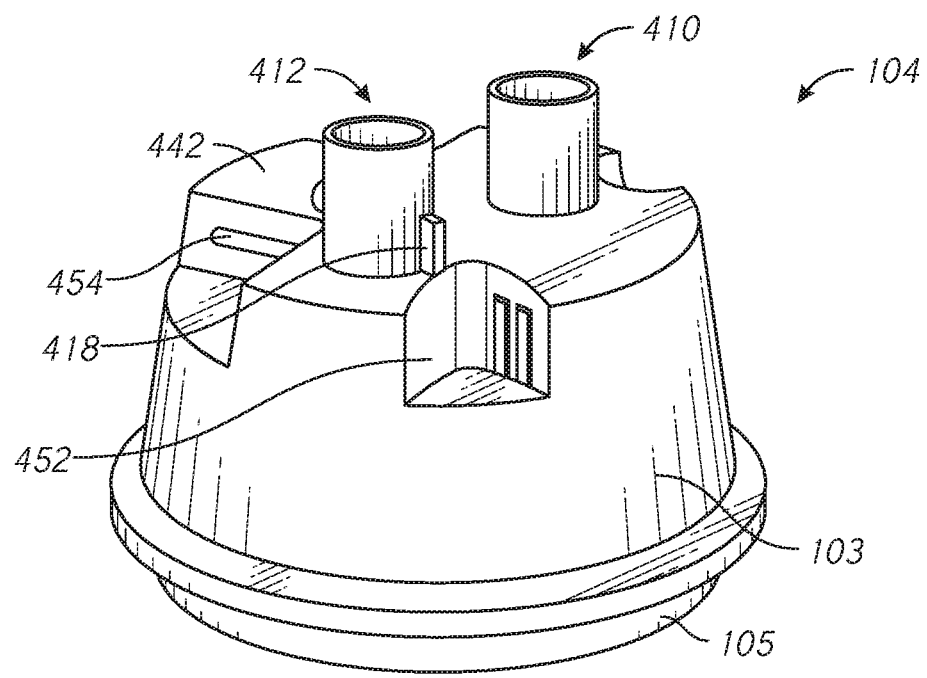
FIG. 12 is a side view of a chamber.
Figure 13:
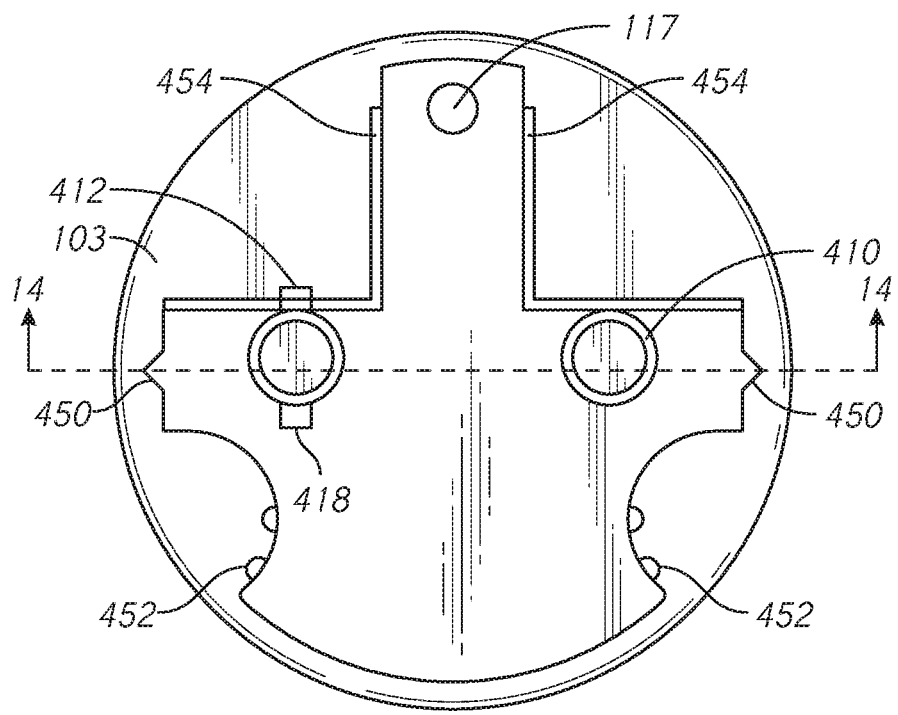
FIG. 13 is a top view of the chamber of FIG. 10.
Figure 14:
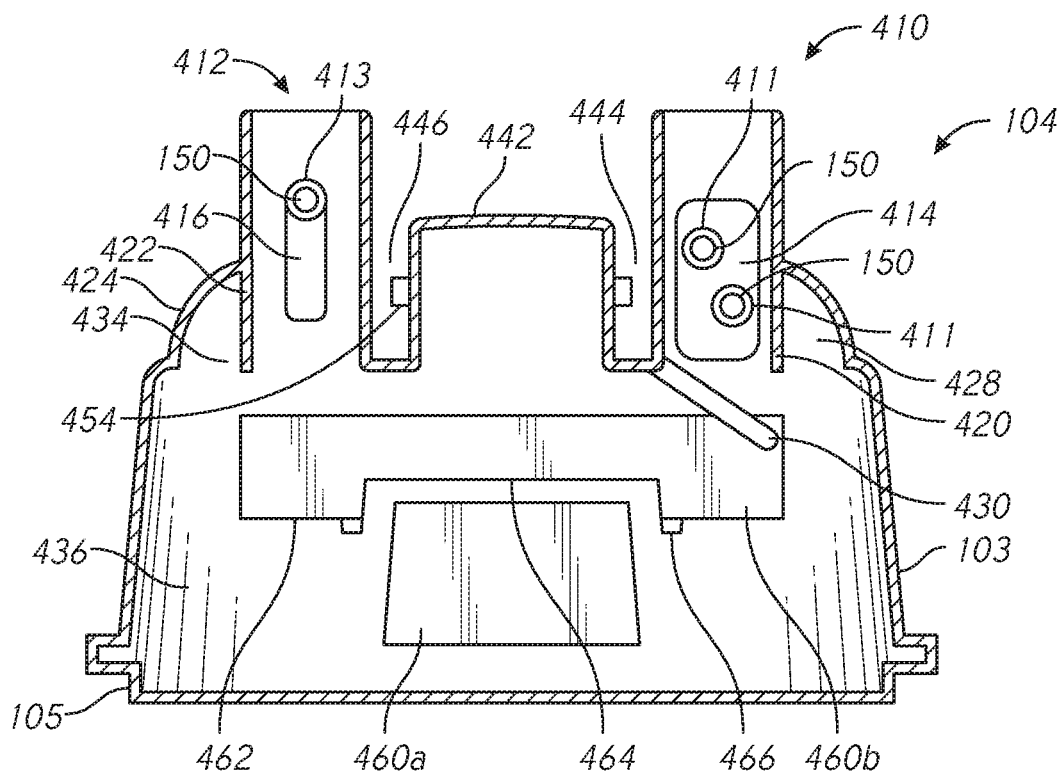
FIG. 14 is a section view taken along the line 14-14 in FIG. 13.

As described herein and shown in FIGS. 12-14, in some configurations, the humidification chamber 104 includes the plastic formed body 103 and the heat conductive base 105 sealed to the body 103. The humidification chamber 104 also includes the generally cylindrical inlet port 410 and the generally cylindrical outlet port 412 extending from a top of the chamber 104.

As shown, the humidification chamber 104 has a generally rounded shape with generally smooth sides, which can make it difficult for the operator to hold the chamber 104 during set-up and installation. Therefore, as shown in FIG. 13, the chamber 104 can include grips 452 to advantageously allow the operator to hold the chamber 104 more easily during installation and/or removal. In some embodiments, for example as illustrated in FIG. 9, the grips 452 are positioned at particular locations on the chamber 104 to help guide the operator to correctly orient the chamber 104 when sliding the chamber 104 onto the heater base 102. In some embodiments, the grips 452 extend partially or completely around the chamber 104. The grips 452 can include one or more of, for example, depressions or cavities on the chamber 104 surface, vertical fins, a textured surface, and/or a handle. In the illustrated configuration, a sidewall of the chamber 104 includes recesses that extend inwardly toward the chamber 104. The recesses can include ribs or the like to enhance the ability of a user to grip the chamber 104 by the recesses. The recesses can be positioned along a forward facing surface to help orient the chamber 104 for installation. In some configurations, the recesses extend only partially up the full height of the chamber 104. In some configurations, the recesses are opposed to each other such that a gripping force can be applied with fingers and thumb by the user.

Figure 16:
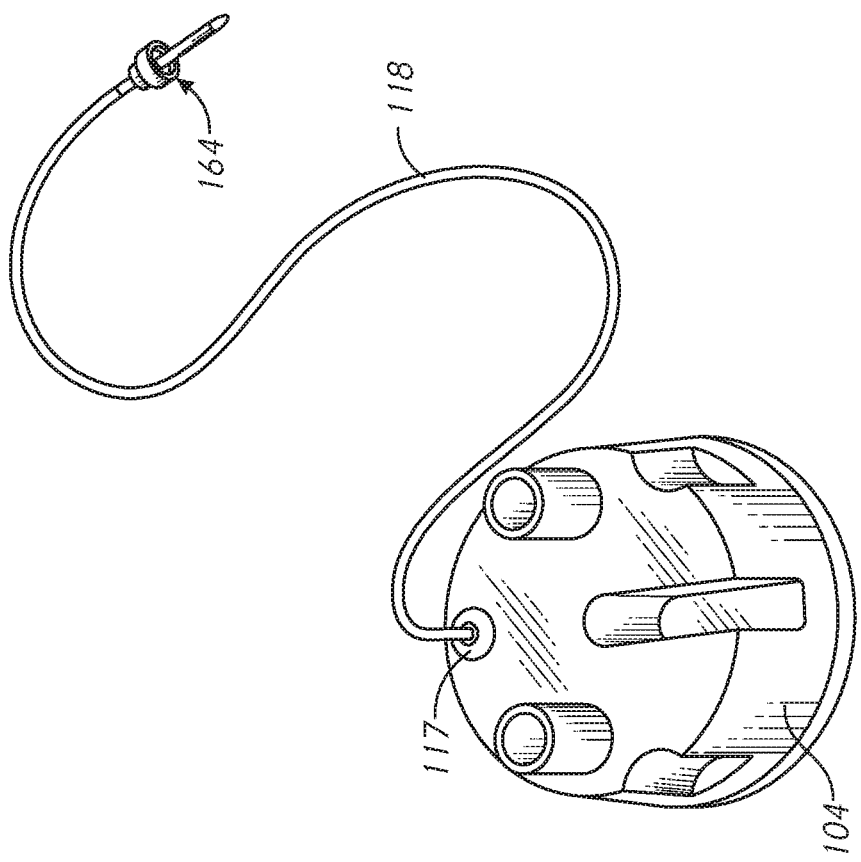
FIG. 16 is a depiction of a chamber with a feed set.

The chamber 104 can also include an opening or port 117 for the connection of a liquid conduit or feedset 118. The liquid conduit 118 can extend from the port 117, as shown in FIG. 16. In some configurations, the liquid conduit 118 can connect to a spike 164 for a water bag. In some configurations, the liquid conduit 118 can be integrally formed with or permanently coupled to the chamber 104. The liquid conduit 118 can be secured in the liquid inlet 117 with an adhesive such as glue or any other suitable technique. The spike can be coupled to the liquid conduit 118 via an adhesive, sonic welding, an interference fit, or any other suitable means. In some embodiments, the spike includes a vent. If the spike is inserted into, for example, a plastic, collapsible bag, the vent is plugged. However, if the spike is inserted into a rigid container, such as a glass bottle, the vent is open and allows air to enter the container to help reduce or prevent negative pressures in the container. The vent can include a filter that is permeable to gases but impermeable to liquids.

In some embodiments, the humidification chamber 104 can include features to help reduce the likelihood of the level of liquid in the chamber 104 from exceeding a particular level. For example, the chamber 104 can include one or more floats 460*a*, 460*b* as shown in FIG. 14. The floats rise and fall with the level of liquid in the chamber 104. When the liquid level reaches a certain level, the floats obstruct or block the liquid conduit 118 port to stop or slow further ingress of liquid into the chamber 104. Other similar features also can be used. In the illustrated embodiment, a plurality of floats 460*a*, 460*b* are used, each float adapted to stop the further ingress of liquid into the chamber 104. To this end, the second float 460*b* provides a backup or safety mechanism, thereby further reducing the likelihood of the chamber 104 overfilling.

In some embodiments, one or more of the floats 460*a*, 460*b* can include features to help direct air flow through the chamber 104 from the inlet port 410 to the outlet port 412. For example, as shown in FIG. 14, a lower surface 462 of the secondary float 460*b* can include a recessed region 464. The recessed region 464 results in a ridge 466 in the illustrated configuration. The ridge 466 and the recessed region 464 can help direct airflow within the chamber 104.

In some embodiments, the secondary float 460*b* is made of acrylonitrile butadiene styrene (ABS). This material can advantageously allow for an improved weld joint between two halves of the float 460*b* and improved thermal properties to inhibit deformation. For example, the secondary float 460*b* is configured to enclose a volume of air following formation. During transit at high altitudes, if the secondary float 460*b* is not formed of a sufficiently deformation-resistant materials, the secondary float 460*b* can be deformed in a manner that does not readily recover upon return to lower altitudes.

In some embodiments, the inlet port 410 and/or the outlet port 412 include one or more apertures extending through the wall of the respective port. For example, in the illustrated embodiment, the back of the inlet port 410 includes two apertures 411, and the back of the outlet port 412 includes one aperture 413. The apertures 411, 413 extend through walls of the inlet port 410 and the outlet port 412, respectively, and provide communication paths through the walls of the inlet port 410 and the outlet port 412. In the illustrated configuration, at least a portion of each of the inlet port 410 and the outlet port 412 can have a respective flattened region 414, 416. The apertures 411, 413 extend through the flattened regions 414, 416.

As shown in FIGS. 7 and 14, the sensor probes 332, 334, 330 are spaced and positioned to be received in the apertures 411, 413 of the inlet port 410 and the outlet port 412 when the chamber 104 is installed on the heater base 102. The sensor probes 332, 334, 330 can be configured to be received in apertures 411, 413 in the chamber 104, shown in FIG. 14 and discussed in greater detail herein. As shown in FIG. 14 and described herein, seals 150 can be inserted in the apertures 411, 413 to receive the sensor probes 332, 334, 330. Mounting the sensor probes 332, 334, 330 on the cartridge 300 can advantageously allow for repeatable depth insertion of the sensor probes 332, 334, 330 in the chamber 104 because the distance between the cartridge 300 and the chamber 104 after connection can be controlled.

Figure 15:
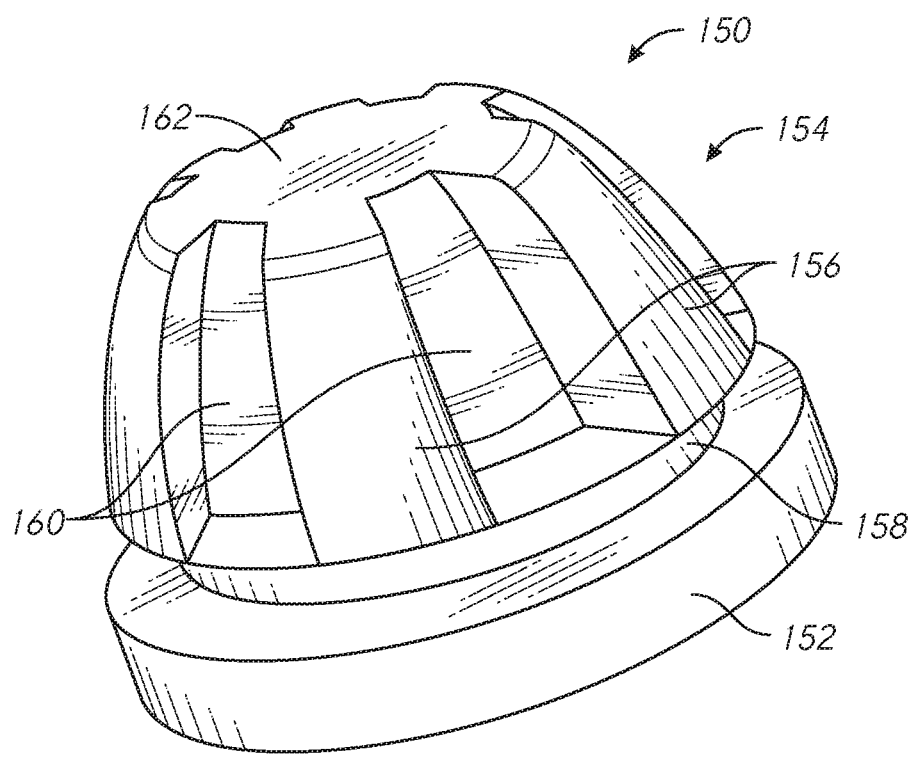
FIG. 15 is a side view of a grommet or seal used in the chamber of FIG. 10.

The apertures 411, 413 can be configured to receive sensors to measure various properties of gases entering and exiting the chamber 104. For example, in some embodiments, the apertures 411, 413 are configured to receive sensors mounted on a sensor cartridge 300 as shown in FIG. 7 and described herein. With reference to FIGS. 14 and 15, in some embodiments, seals or grommets 150 can be positioned in the apertures 411, 413. By positioning the apertures 411, 413 on the flattened regions 414, 416, the seals or grommets 150 are better able to seal the apertures 411, 413 due to a simplification of the geometry of the seals or grommets 150.

The seals or grommets 150 can at least substantially pneumatically seal the apertures 411, 413 so that the gas flow path through the chamber 104 is isolated from ambient. Accordingly, in the illustrated configuration, the seals 150 define a barrier that reduces the likelihood of fluid or gas passing through the apertures 411, 413. In some applications, at least one of the seals 150, and preferably all of the seals 150, also is resistant to the passage of vapor. The seals 150 can be configured to receive the sensors so that the sensors can detect properties of gases flowing through the humidification system while remaining pneumatically sealed from the flow path. The seals 150 advantageously allow the sensors to function without being in direct contact with gases in the flow path, so the sensors can be reused and do not require cleaning between uses.

The seals 150 can be formed from any suitable material. In some applications, the seals 150 are formed from a resilient or flexible material. In some applications, one or more of the seals 150 can be formed of a material with a Shore-A hardness of between about 20 and about 80, and more preferably between about 40 and about 60. In some applications, one or more of the seals 150 can be formed of Silicone, polyethylene, or thermoplastic polyurethane.

In some arrangements, the seals 150 can be formed directly into the inlet port 410 and the outlet port 412, for example, by overmoulding. In other arrangements, the inlet port 410 and the outlet port 412 and seals 150 can include features to help retain the seals 150 in position within the apertures 411, 413 and provide for easier manufacturing and assembly. For example, with reference to FIG. 15, the seal 150 includes a generally cylindrical base 152. The seal 150 also comprises a generally bell-shaped head 154. The illustrated bell-shaped head 154 comprises a plurality of triangular ribs 156 around its perimeter. In some embodiments, a channel 158 can be defined between the base 152 and the head 154. The channel 158 is sized to accommodate the flattened regions 414, 416 in the walls of the inlet port 410 and the outlet port 412. As introduced above, the flattened areas 414, 416 allow the cylindrical base 152 of the seal 150 to fit more flush against the inlet port 410 and the outlet port 412.

In some embodiments, the seals or grommets 150 can include the use of surface modifications and/or microstructures to improve wicking. As described herein, the use of surface modification agents and/or microstructures can result in spreading of liquid onto the surface and inside or on the microstructures. Accordingly, any of the configurations described above can be used in conjunction with the seals or grommets 150. The interaction can increase the liquid-vapor interface area and reduce the thickness of the liquid layer on top of the surface. The combination of increased surface area and reduced thickness improves liquid evaporation, compared to liquid of the same volume of liquid on a flat surface. Accordingly, it can be advantageous to treat the seals or grommets with a material or materials for increasing the surface energy. Surfactants, such as cationic surfactants, can be particularly desirable additive materials. Suitable surface modifying agents include glycerol monostearate (GMS), ethoxylated amine, alkanesulphonate sodium salt, and lauric diethanolamide and additives comprising these substances.

The ribs 156 can deflect to allow the seal 150 to be inserted into the apertures 411, 413. The ribs 156 can then return to an expanded state to help hold the seal 150 in place within the apertures 411, 413. As the ribs 156 depress, they spread into spaces 160 between the ribs 156. In some embodiments, a radio of a width of the rib 156 to a width of the space 160 between ribs 156 is about 1:1. In some embodiments, the ratio is about 3:7. A ratio that is too high (i.e., the space 160 between ribs 156 is small compared to the ribs 156) may not allow the ribs 156 to depress sufficiently, resulting in greater difficulty installing the seal 150 in the apertures 411, 413. A ratio that is too low (i.e., the space 160 is large compared to the ribs 156) may provide a reduced retention force so that the seal 150 is not held as securely in the apertures 411, 413. In the illustrated embodiment, the seal includes eight ribs 156, but more or fewer ribs 156 are also possible. However, if too many ribs 156 are included, the ribs 156 would be made thinner and might be weaker. Alternatively, including too few ribs 156 might require making the ribs 156 larger, leaving less space to spread.

In some embodiments, when a sensor is inserted into the seal 150, a tip 162 of the seal 150 can stretch to conform to the shape of the sensor. As the amount of stretch to accommodate the sensor increases, the seal material becomes thinner. This can advantageously improve the reactivity and accuracy of the sensor, increase the contact area between the sensor and seal as the seal stretches to match the shape of the sensor, and more securely hold the seal in the aperture. However, if the tip 162 of the seal is too flat and requires too great a degree of stretch to accommodate the sensor, it can be more difficult to insert the sensor in the seal and the seal material may degrade or break.

Additionally, the seal can be configured to receive a heated thermistor. At high temperatures, a seal made of, for example, silicone may begin to degrade or deform. Therefore, in some embodiments, the seal 150 can be designed to stretch more evenly along the length of the head 154 rather than the stretch being limited to primarily the tip 162. This can help distribute the forces and help reduce degradation and/or deformation of the seal. In the illustrated embodiment, the seal can have a length of about 5.6 mm or about 6 mm, a base 152 diameter of about 8 mm, a diameter measured at the widest portion of the ribs 156 of about 7.50 mm, and a tip thickness of about 0.20 mm. The ribs 156 can be sized so that the space 160 between ribs is about 1.4 mm.

In some arrangements, at least one of the seals 150 can be permanently or at least semi-permanently attached to the apertures 411, 413. In some arrangements, at least one of the seals 150 can be removable and replaceable. The seals 150 can be configured to have a useable life similar to that of one of the other components. For example, the seals 150 preferably comprise a useable life similar to the chamber 104 such that the chamber 104 and the seals 150 would be disposed of at the same time. In some configurations, especially where the seals 150 are permanently attached to the chamber 104, the seals 150 preferably have a longer life than the chamber 104 such that the seals 150 are not the limiting component on a life span of the chamber 104.

The seals 150 are configured to securely but removably receive sensors. In some embodiments, the sensors can function with higher accuracy if the depth of insertion into the seals 150 and flow path can be controlled and repeated. To help provide for controlled and repeatable insertion of the sensors, in some embodiments the sensors are mounted directly or indirectly on the heater base 102. For example, rather than being mounted directly on the heater base 102, the sensors can be mounted relative to a sensor cartridge 300 that is coupled to the heater base 102.

In some embodiments, one or both of the inlet port 410 and the outlet port 412 includes features to help a user distinguish the ports. One or both of the inlet port 410 and the outlet port 412 can include features to allow for connection of a connector coupled to the supply conduit 132 and/or the inspiratory conduit 120. For example, in the illustrated embodiment, the front of the outlet port 412 includes a rib 418. The rib 418 can be configured to be received by a corresponding recess on a chamber end connector coupled to the inspiratory conduit 120 as discussed in greater detail herein. In addition, in the illustrated embodiment, the aperture 413 can be surrounded by an embossment 440.

The central channel 342 is configured to receive a corresponding boss or raised portion 442 on the top of the chamber 104, shown in FIGS. 12-14. The fins 344, 346 of the cartridge 300 are configured to slip into grooves 444, 446 on the chamber 104 located between the raised portion 442 and the inlet port 410 and the outlet port 412.

The sidewalls 340 and fins 344, 346 act as lead-in features to help guide the user in correct installation of the chamber 104 on the heater base 102. The sidewalls 340 and fins 344, 346 also help protect the sensors from damage that could be caused by improper contact with the base. For example, if the user attempts to install the chamber 104 with the front or a side of the chamber 104 facing the cartridge 300 so that the apertures 411, 413 in the inlet port 410 and the outlet port 412 are not aligned with the sensor probes 332, 334, 330, the sidewalls 340 and fins 344, 346 will contact surfaces of the chamber 104 to help prevent or inhibit contact between the sensors and relatively hard surfaces of the chamber 104.

The fins 344, 346 can also include features to help stabilize the chamber 104 relative to the cartridge 300 and inhibit rotation, tilting, and/or yaw of the chamber 104. For example, as shown in FIGS. 2 and 3, inner surfaces of the fins 344, 346 can include generally horizontal grooves 354 extending from front edges of the fins 344, 346 toward the back of the cartridge 300. The grooves 354 are configured to receive corresponding rails 454 extending along the sides of the raised portion 442 of the chamber 104 as shown in FIGS. 12-14. When the chamber 104 is installed on the heater base 102 and coupled to the cartridge 300, the rails 454 sit in the grooves 354. The coupling configuration of the rails 454 in the grooves 354 can help inhibit the chamber 104 from excessive tilting.

Chamber Baffles

In some applications, the humidification system 100 can be used for delivery of gases at relatively high flow rates, for example, up to or greater than about 100 L/min. In some cases, certain features designed to improve humidity delivery at higher flow rates can cause liquid from within the chamber 104 to splash out through the outlet port 412. This is not desirable.

With reference to FIG. 12, the humidification chamber 104 can include the plastic formed body 103 with the heat conductive base 105 sealed thereto. In some applications, such as that shown in FIG. 9, the humidification chamber 104 is configured to be installed on the heater base 102 so that the heat conductive base 105 of the humidification chamber 104 contacts the heater plate 108 of the heater base 102. The humidification chamber 104 is adapted to hold a volume of liquid, such as water, that can be heated by heat conducted through the heat conductive base 105 from the heater plate 108.

In some embodiments, at least one of the inlet port 410 and the outlet port 412 can include one or more features to help inhibit liquid from leaving the chamber 104 other than in a vapor form. For example, one or more of the inlet port 410 and the outlet port 412 can include inner wall extensions 420, 422, respectively, that extend into the chamber 104 from the point at which the ports enter the chamber 104, as shown in FIG. 14. In other words, the top of the chamber 104 includes a dome 424 through which the inlet port 410 and the outlet port 412 enter into a cavity 426 defined within the chamber 104. The extensions 420, 422 extend further inward into the cavity 426 relative to the dome 424. In the illustrated embodiment, the inlet port inner wall extension 420 and the outlet port inner wall extension 422 extend downward substantially equally into the cavity 426 of the chamber 104. As shown, the dome 424 and the extensions 420, 422 can define pockets 428, 434 between a sidewall 436 of the chamber 104 and the end of the respective extensions 420, 422.

The chamber 104 can also include one or more baffles at or near the end of at least one of the inlet port extension 420 and the outlet port extensions 422. For example, an inlet port baffle 430 extends at an angle downwardly and toward the sidewall 436 of the chamber 104 from the inlet port extension 420. The baffle 430 extends downwardly below the lowermost portion of the extension 422 of the outlet port 412. The baffle 430 can advantageously help direct air flow in the chamber 104. For example, the baffle 430 can help direct air entering the chamber 104 from the inlet port 410 down to the liquid surface. This can help promote mixing of vapor with the gases to increase humidity delivery. The sideways orientation of the inlet port baffle 430 can also help direct incoming gases toward the sidewall 436 of the chamber 104 so that the gases will travel down the side wall and across the liquid surface instead of flowing directly to the outlet port 412.

Figure 32:
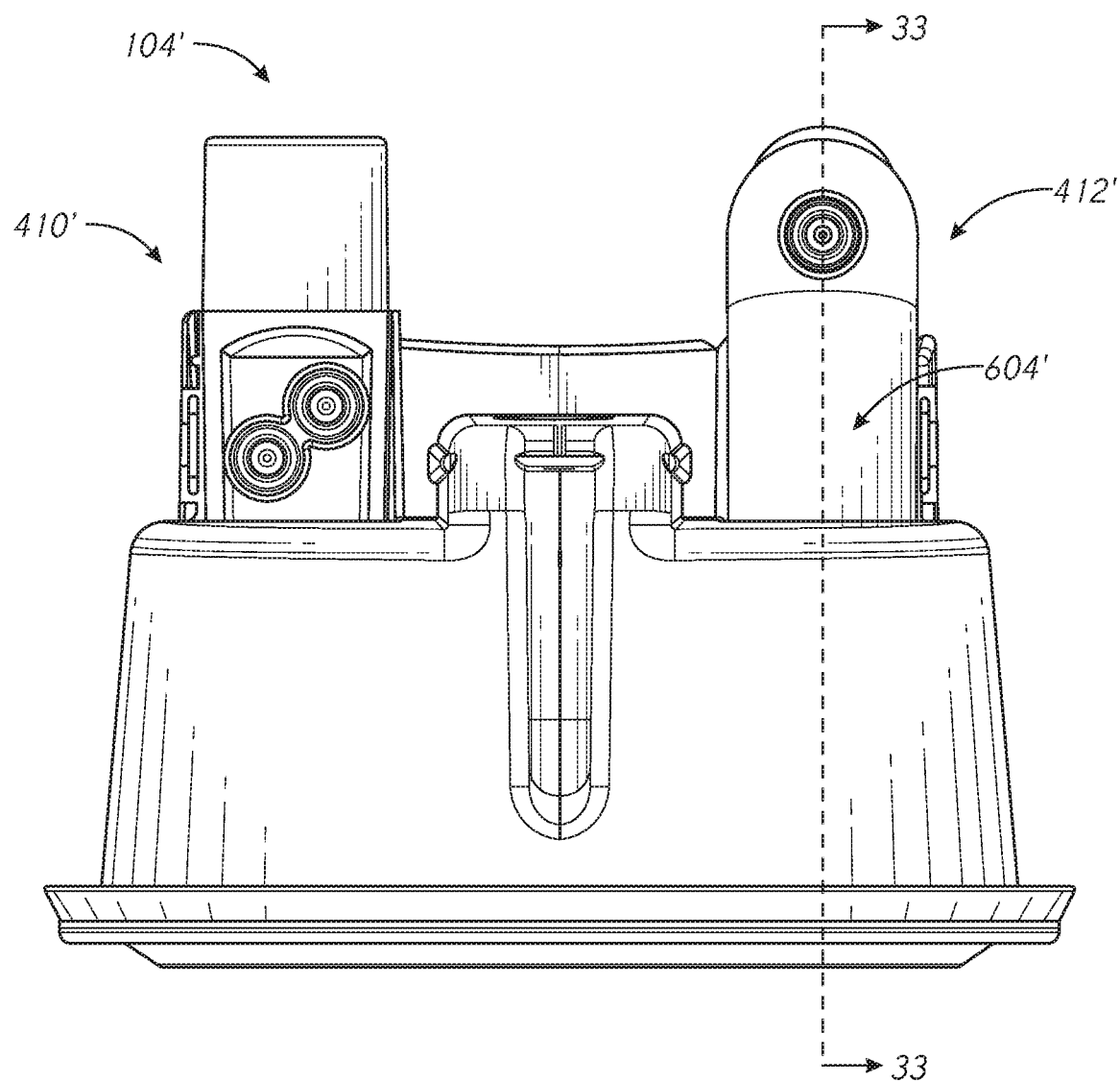
FIG. 32 illustrates another chamber.
Figure 33:
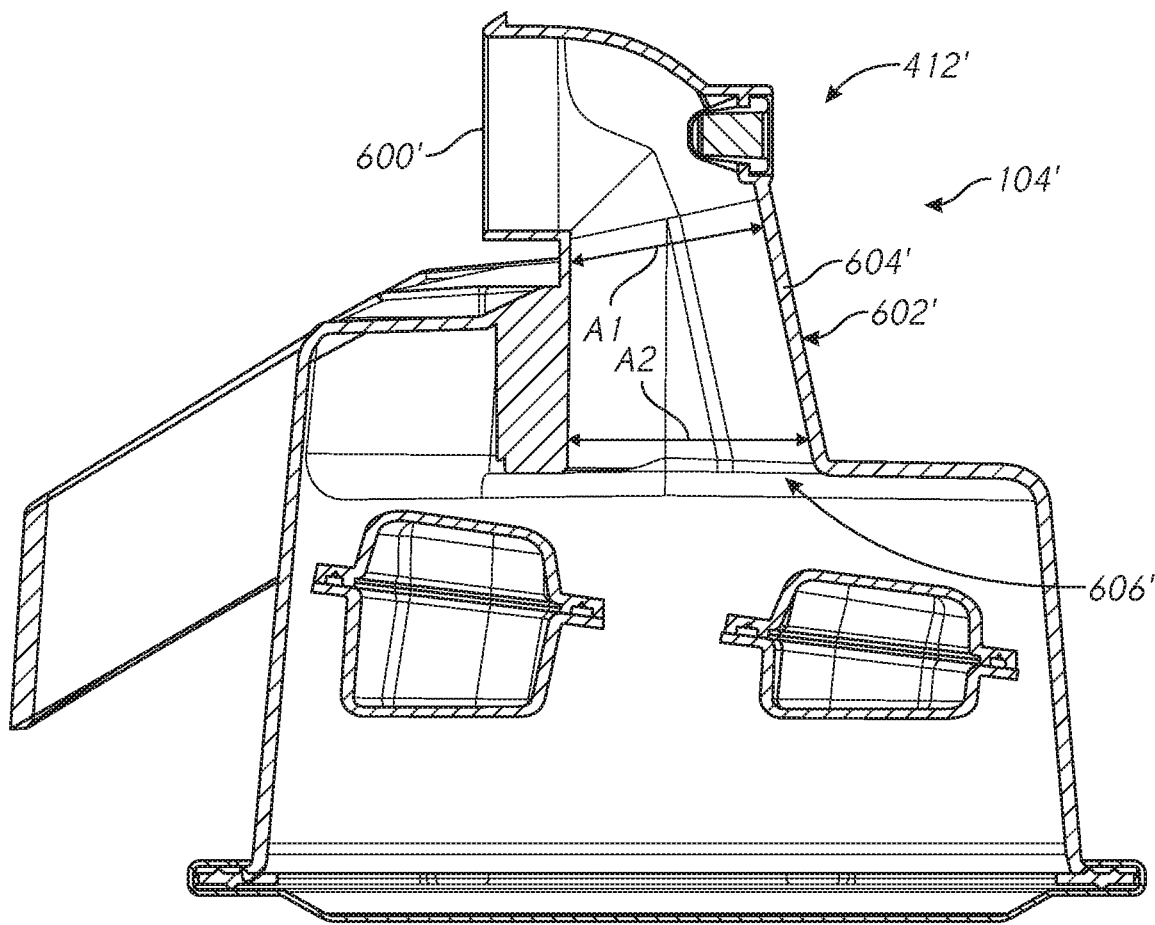
FIG. 33 is a sectioned view through a portion of the chamber of FIG. 32.

In the configuration of FIGS. 32-33, a chamber 104' is illustrated. The chamber 104' can include an inlet 410' and an outlet 412'. The outlet 412', as described elsewhere herein, includes an opening 600' that directs flow in a generally horizontal direction. The outlet 412'. The opening 600' defines a mouth that is positioned generally atop a substantially vertical throat 602'. The throat 602', rather than being cylindrical, includes a tapering shape. For example, the area A1 is smaller than the area A2, as shown in FIG. 33. In some configurations, a portion of the wall or walls defining the throat 602' is inclined, as also shown in FIG. 33. The portion 604' of the wall furthest from the mouth or opening 600' can slope gently. By providing the portion 604' that is not vertical, the cross sectional area is greater at an entrance 606' into the throat 602' than at the mouth 600' or at a region between the entrance 606' and the mouth 600'. The opening of the cross sectional area allows the bulk mass flow to be on a slight angle (i.e., the flow does not have to be redirected a full 90 degrees), which reduces flow separation. In addition, the flow rate closest to the entrance 606' is less than that at the mouth 600'. Thus, the illustrated configuration can reduce the ability of the flow to carry water in droplet form and can resist carrying water splashes from within the chamber into the conduit.

Chamber Port Cap

Figure 17:
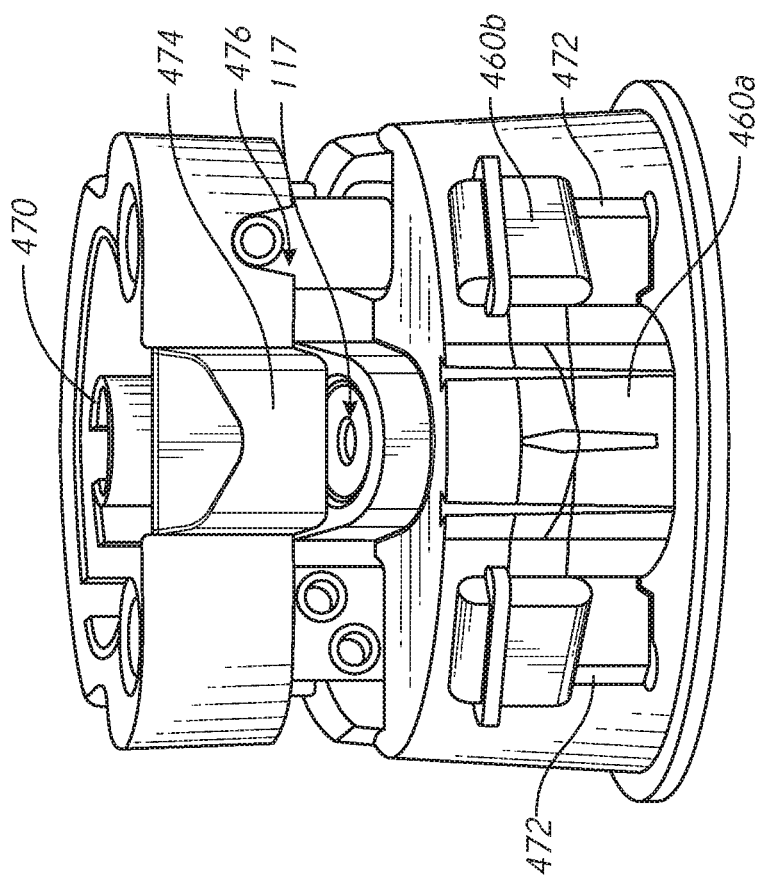
FIGS. 17 and 18 are illustrations of the humidification chamber with a port cap assembly.

With reference to FIG. 17, the humidification chamber 104 can be packaged with a port cap 470 covering the inlet port 410 and the outlet port 412. The port cap can seal or generally enclose the top of the chamber 104 during shipping and storage. As shown, the port cap 470 includes a recess 476 to accommodate the outlet port 412 aperture 413 and sensor 330 extending into the aperture 413. The port cap 470 can include legs 472 that extend into the inlet port 410 and the outlet port 412. The legs 472 help restrain the floats 460 in position for shipping. The legs 472 can be generally half-moon shaped to allow the legs 472 to fit around the baffles 430, 432. If the liquid conduit 118 is connected to the liquid source before the port cap 470 is removed, there is a risk of the chamber 104 overfilling because the floats 460 are still restrained and cannot function to slow or stop the flow of liquid into the chamber 104. To reduce the likelihood over overfilling, the chamber 104 is packaged with the liquid conduit 118 also covered by the port cap 470. As shown, the port cap 470 includes a rear projection 474 configured to cover the liquid inlet 117 and liquid conduit 118 extending from the inlet 117. The rear projection 474 is configured to slide into the central channel 342 of the sensor cartridge 300 when the humidification chamber 104 is installed on the heater base 102, so the shape of the port cap 470 can also help the user properly orient the chamber 104 for installation on the heater base 102.

Figure 18:
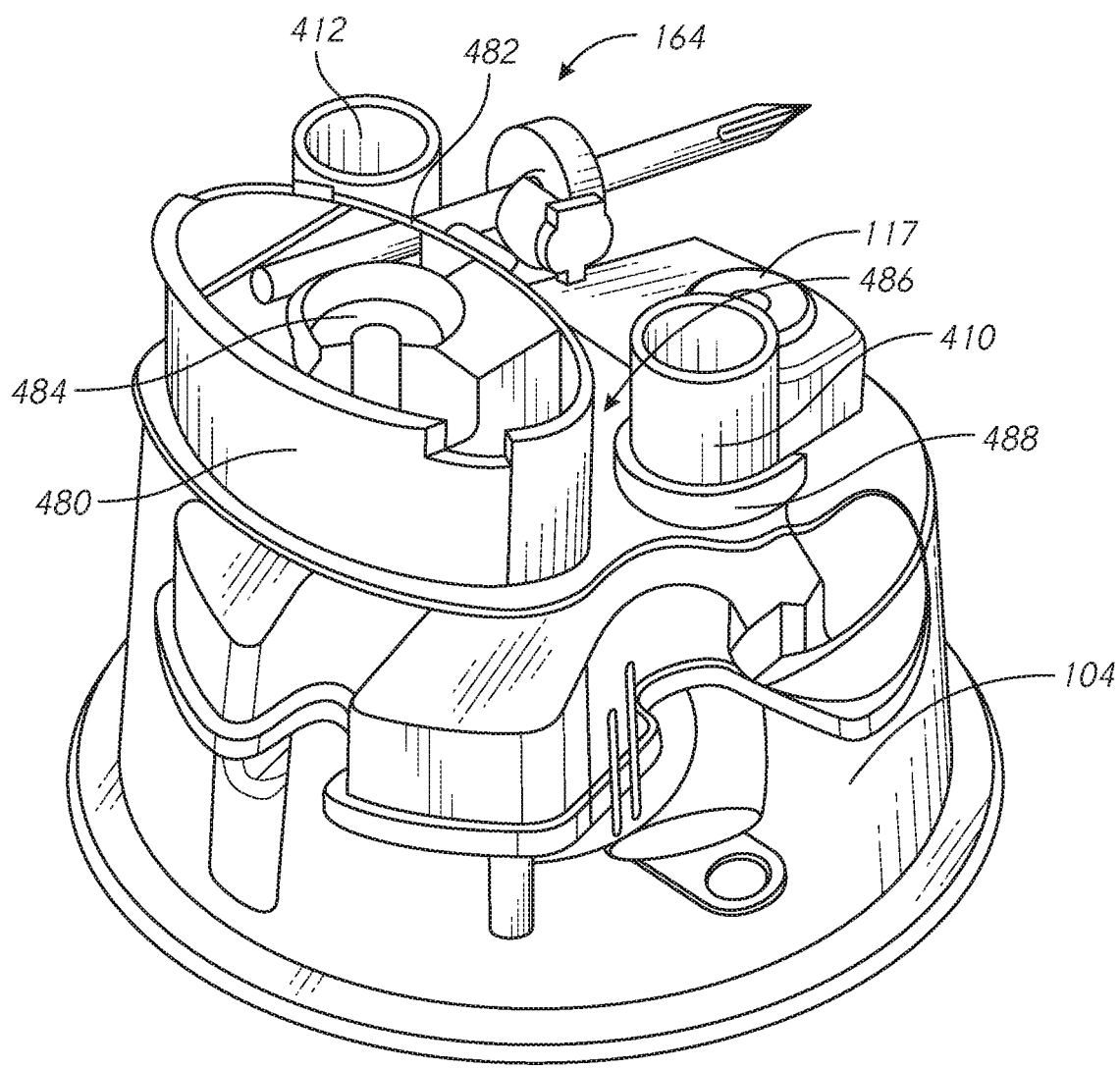

In some configurations, the liquid conduit 118 can be wound around, and can be contained by, a winder 480 provided on the chamber 104, as shown in FIG. 18. In some embodiments, the winder 480 is coupled to the chamber 104 with clips 488 or other features that connect to, clip to, or otherwise engage the inlet port 410 and the outlet port 412. The liquid conduit 118 extends from the liquid inlet 117 in the chamber 104 and through a vent 486 in the front of the winder 480 to wind around the winder 480 and couple to the spike 164. The spike 164 can rest horizontally in a slot 482 in the winder 480 for shipping and storage. In some configurations, the winder 480 includes features to secure the spike in a horizontal position (for example, a shipping position) and in a non-horizontal or vertical position (for example, a testing position). For example, the winder 480 can include a partially circular receptacle 484 within the winder 480 configured to receive the spike 164 in a generally vertical position for testing. After testing, the spike 164 can be placed in the slot 482 for shipping and storage. During set-up, after the humidification chamber 104 is installed on the heater base 102, the port cap 470 is removed, the spike is removed from the slot 482, and the liquid conduit 118 is unwound from the winder 480 and connected to the liquid source via a spike 164. In some embodiments, the user can remove the winder 480 from the chamber 104 and discard the winder 480 after unwinding the liquid conduit 118. Once the spike 164 connects to the liquid source, liquid will begin filling the chamber 104.

End Cap

Figure 20:
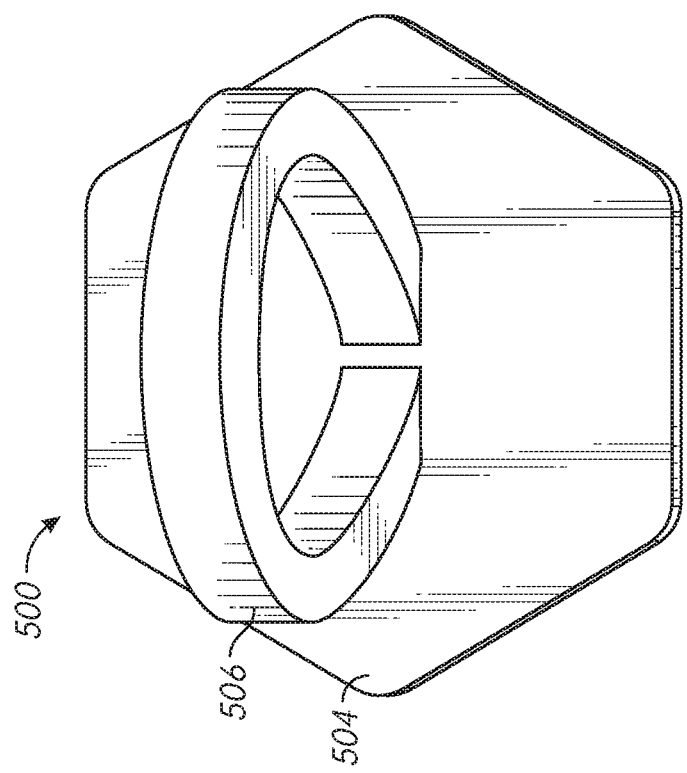
FIG. 20 illustrates a top perspective view of the end cap of FIG. 19.
Figure 19:
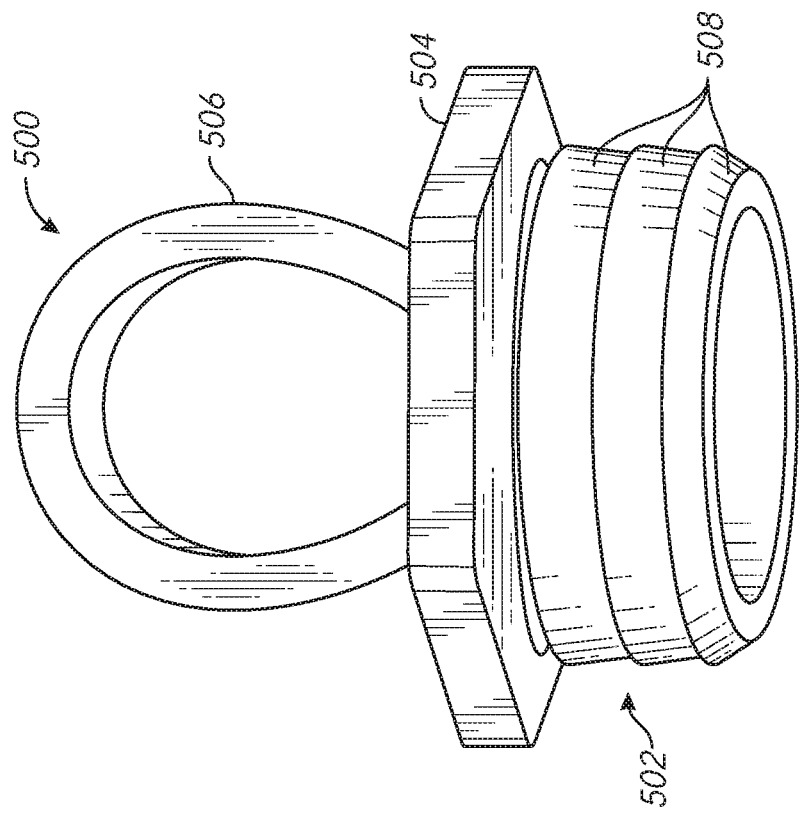
FIG. 19 illustrates a side view of an end cap for a Y-piece or conduit.

One or more of the components of the breathing circuit assembly 123 can be packaged for shipping and/or storage with an end cap 500 coupled to one or both ends of the conduit. For example, the end cap 500 can be included on the end of the Y-piece 124 configured to couple to the patient interface conduit 126 or the interface 128 as shown in FIGS. 19 and 20. The end cap 500 includes a body 502 configured to be inserted into a Y-piece, a flange 504, and a hook or pull ring 506.

The body 502 includes frustoconical tapers 508. The tapers 508 promote a friction fit between the end cap 500 and a Y-piece. The tapers 508 also create a seal with the Y-piece. The tapers 508 point toward the leading end of the end cap 500 inserted into the Y-piece. The illustrated embodiment includes three tapers 508, although more or fewer are also possible. Including multiple tapers 508 provides redundancy to help ensure a sufficient seal and friction fit. However, including too many tapers 508 can create too great of a contact area. This can make the end cap 500 difficult to remove. In some embodiments, the body 502 can be sized to fit different sized Y-pieces, for example, both adult and infant Y-pieces.

The flange 504 is located on the end of the end cap 500 facing the bases or widest parts of the tapers 508. As shown, the flange 504 has a hexagonal shape. The hexagonal shape helps seal the end of the Y-piece and aids end cap 500 removal. A width or diameter of the flange 504 is greater than an outer diameter of the Y-piece to create an overhang. For example, for a 22 mm diameter Y-piece, the flange 504 can have a width of about 24 mm. The hexagonal shape can also provide a visual indicator that the Y-piece connector is blocked and further inhibits the user from attempting to attach other components while the end cap 500 is in place, which may be more likely if the flange 504 was round. Other non-circular shapes also can be used.

Figure 21:
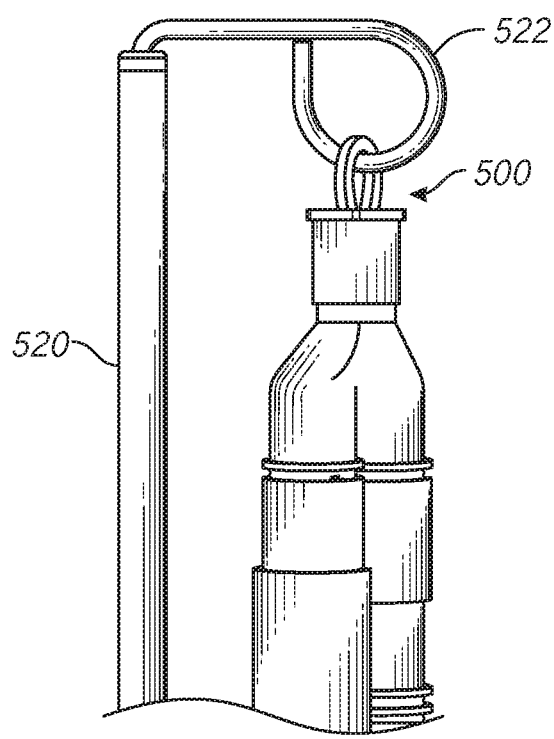
FIGS. 21 and 22 illustrate the end cap of FIGS. 19 and 20 coupled to a circuit component and hanging from a medical stand.
Figure 22:
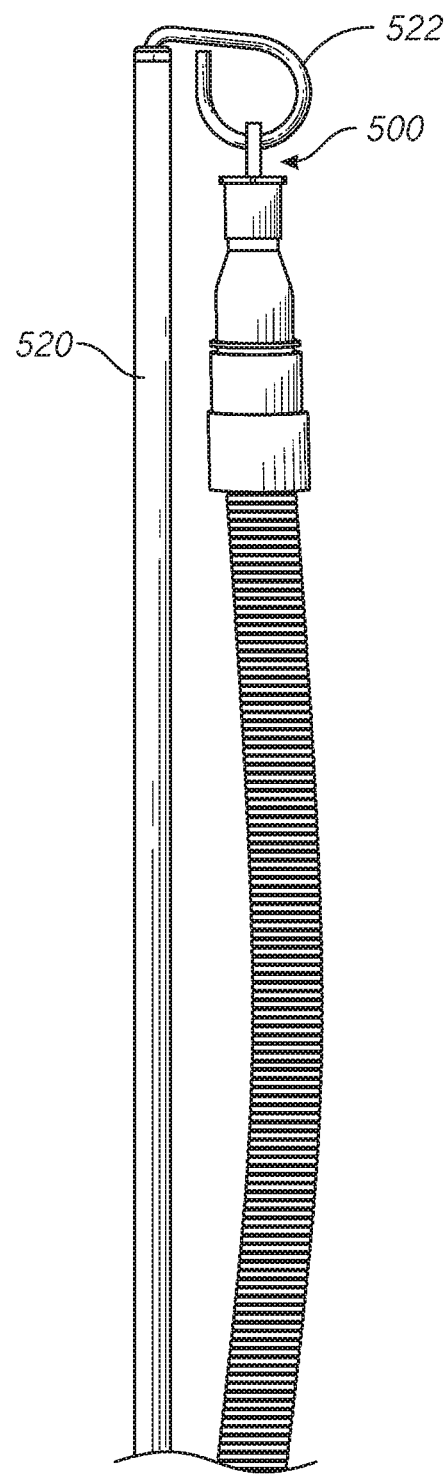

The hook 506 extends from the flange 504. The hook 506 advantageously allows the user to more easily grasp and remove the end cap 500 when needed. The hook 506 also allows the circuit to hang on a medical stand 520 when not in use and/or during system set up, as shown in FIGS. 21 and 22. The hook 506 can have a diameter of at least 8 mm to allow the hook 506 to accommodate medical stand hooks 522.

The body 502, flange 504, and hook 506 can be integrally formed or molded to create a single-piece end cap 500. The end cap 500 should be made of a material that is sufficiently strong while remaining soft or pliant enough to inhibit damage to a Y-piece. In some embodiments, the end cap 500 can be made of Thermolast K. In other embodiments, the end cap 500 can be made of Santoprene having a Shore A hardness of between about 20 and 80, for example, about 55. Santoprene has a higher friction coefficient than some alternative materials, which can help improve end cap 500 retention in a Y-piece.

Alternative embodiments of end caps 500 are illustrated in FIGS. 23A-27E. In these embodiments, the flange 504 is circular rather than hexagonal. Additionally, as shown, the hook or pull ring 506 extends from a side of the flange 504 rather than a top of the flange 504. In some configurations, the hook can be a tab with an aperture defined through the tab. In any event, in the illustrated configurations, the aperture or hook can be positioned off to one lateral side of an axis extending through the body that engages with the component to which the cap is mounted. In other words, the aperture or hook is positioned off to one side of the body and/or flange. Locating the hook 506 to the side of the flange 504 can cause the force used to remove the end cap 500 to be applied in a rotational direction rather than a linear direction. This arrangement can advantageously allow the end cap 500 to be removed with less force.

Figure 23A:
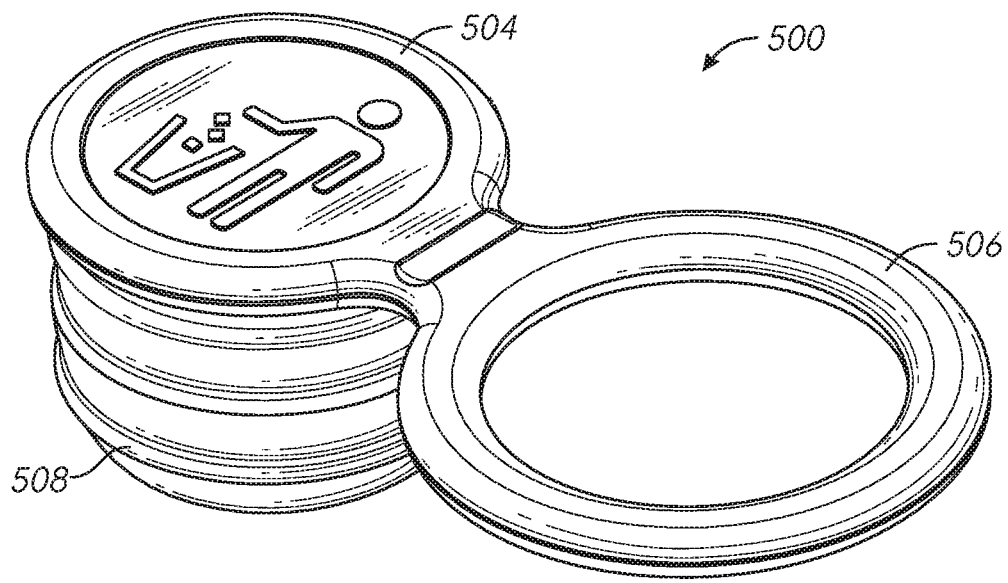
FIG. 23A illustrates a perspective view of an alternative end cap.
Figure 23B:
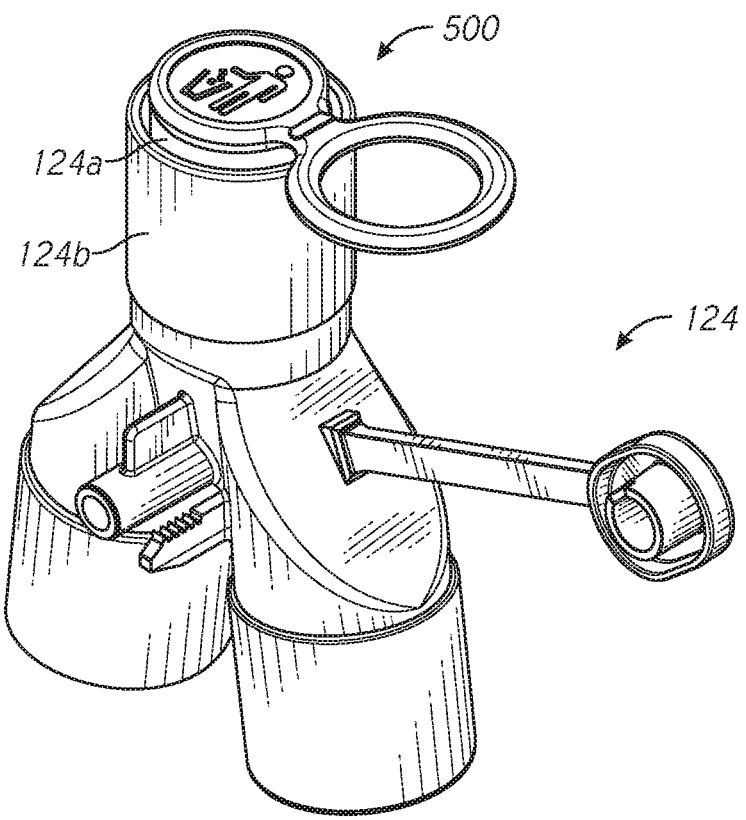
FIG. 23B illustrates the end cap of FIG. 23A coupled to a Y-piece.
Figure 24A:
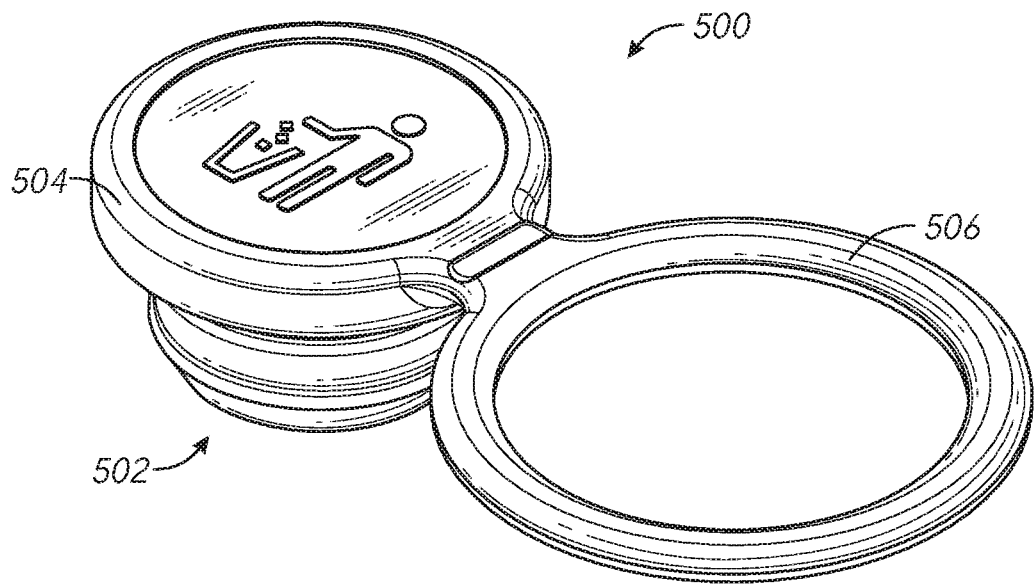
FIG. 24A illustrates a perspective view of another alternative end cap.
Figure 24B:
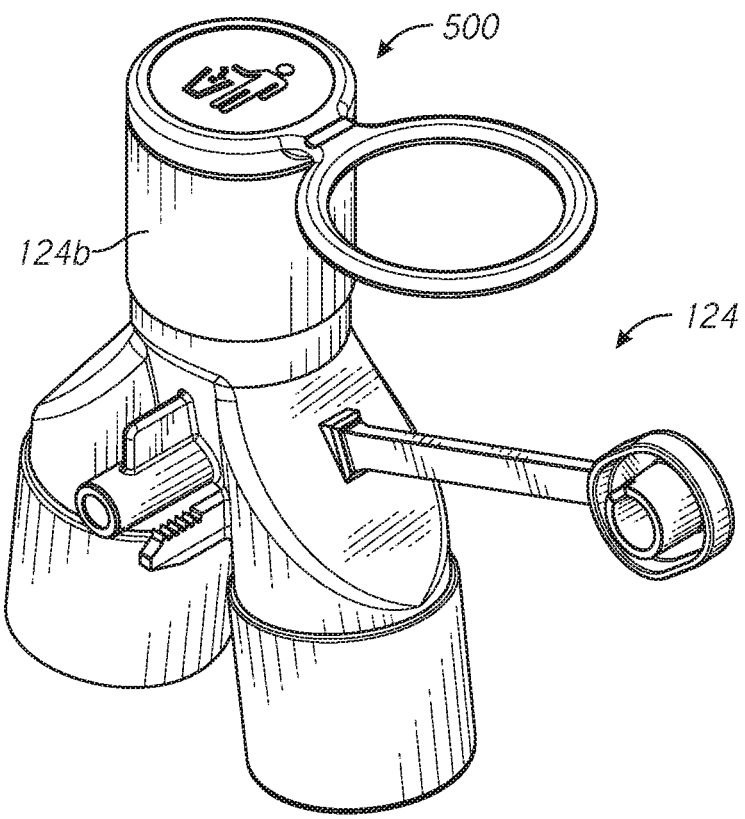
FIG. 24B illustrates the end cap of FIG. 24A coupled to the Y-piece.
Figure 25A:
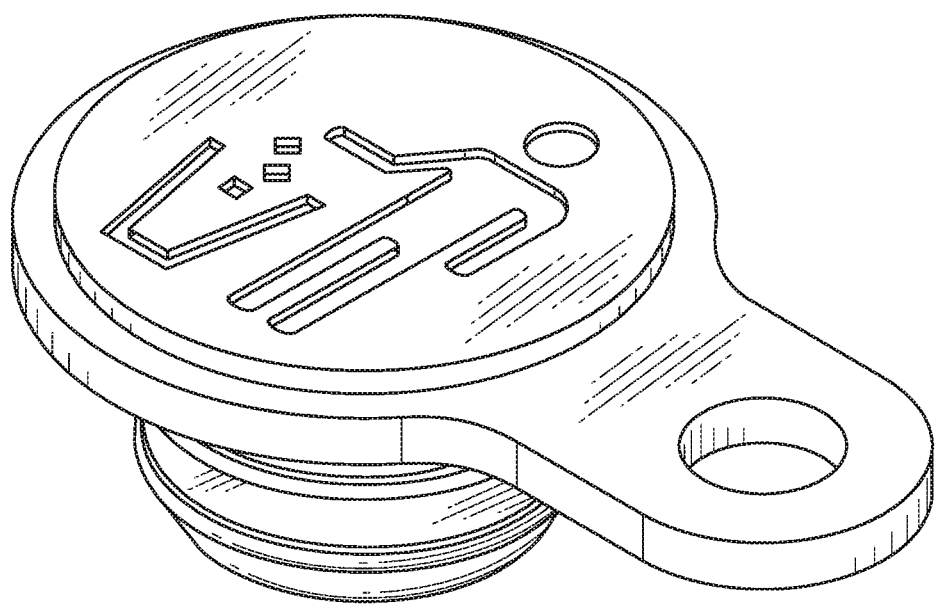
FIG. 25A illustrates a perspective view of another alternative end cap.
Figure 25B:
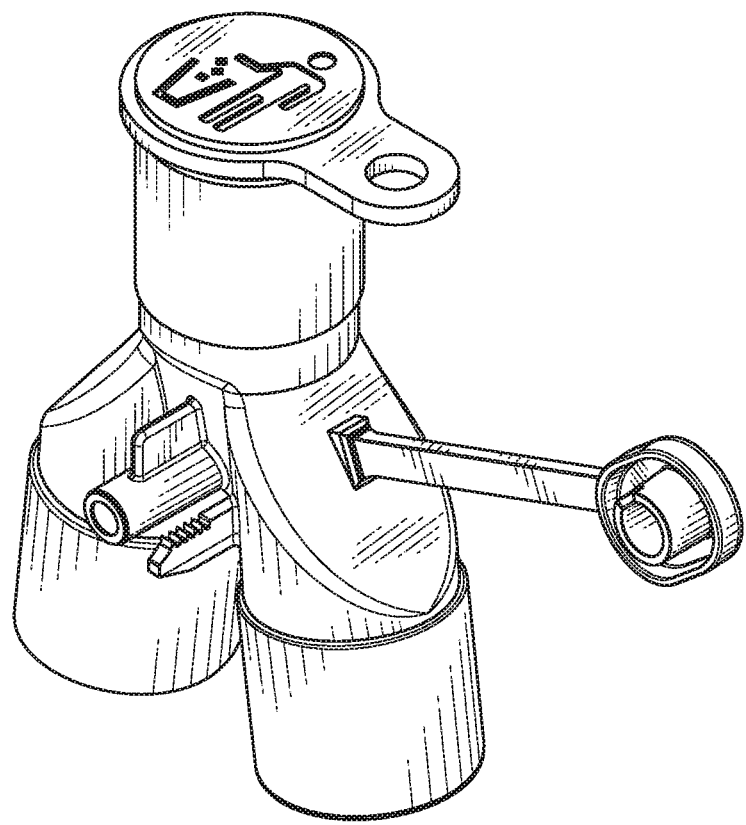
FIG. 25B illustrates the end cap of FIG. 25A coupled to the Y-piece.
Figure 26A:
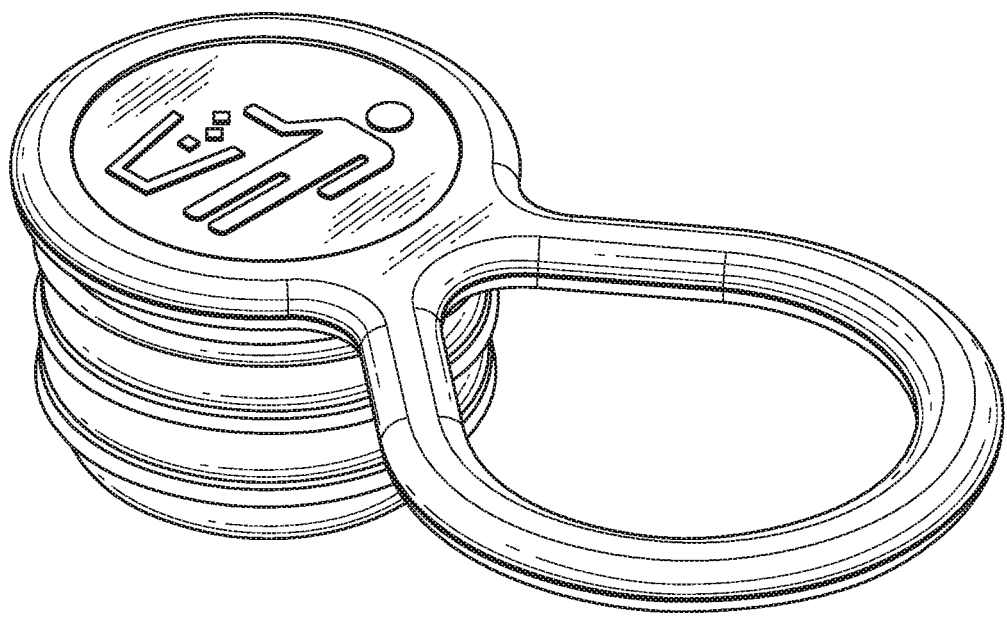
FIG. 26A illustrates a perspective view of another alternative end cap.
Figure 26B:
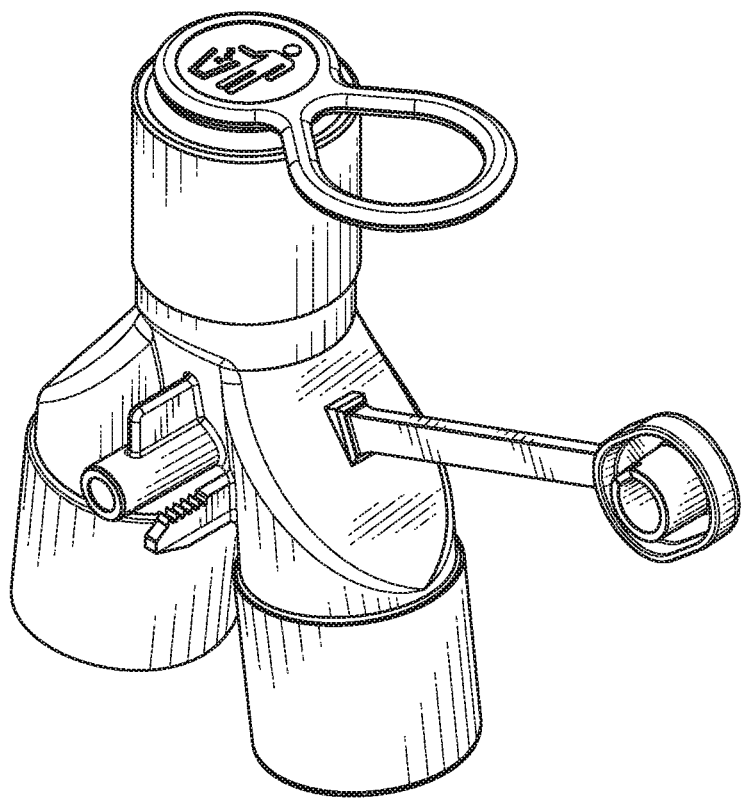
FIG. 26B illustrates the end cap of FIG. 26A coupled to the Y-piece.
Figure 27A:
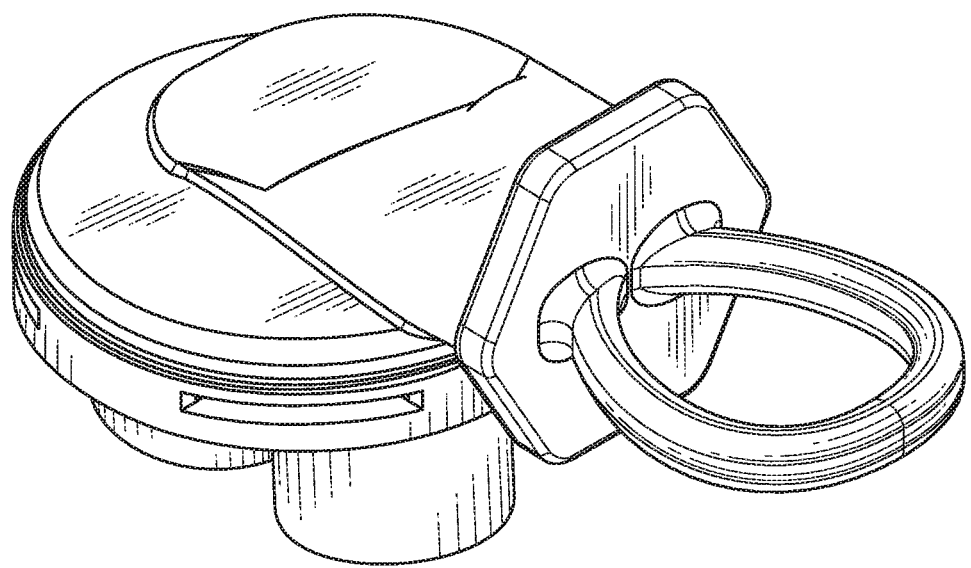
FIGS. 27A-27E illustrate the end caps of FIGS. 19, 23A, 24A, 25A, and 26A, respectively, coupled to an alternative Y-piece.
Figure 27B:
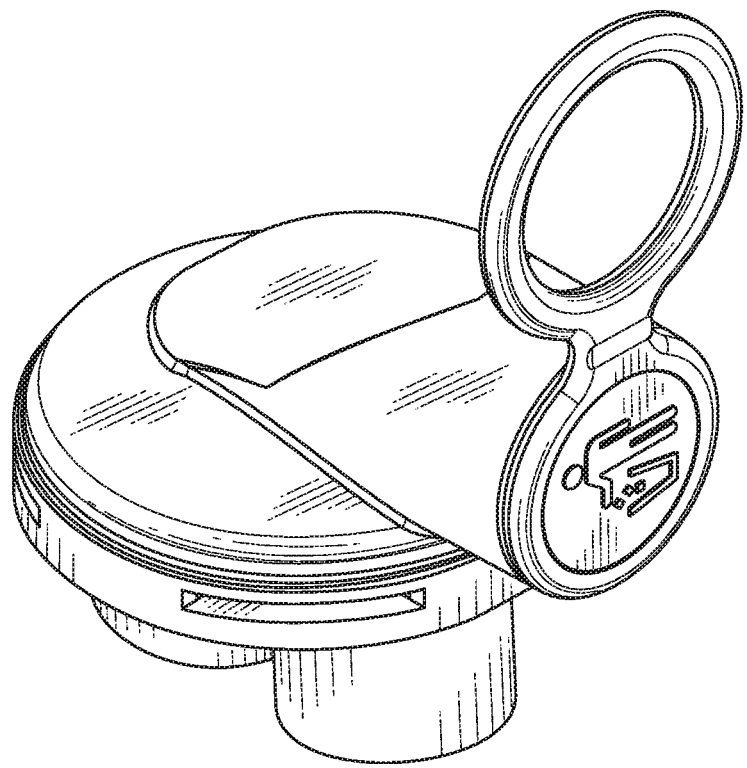
Figure 27C:
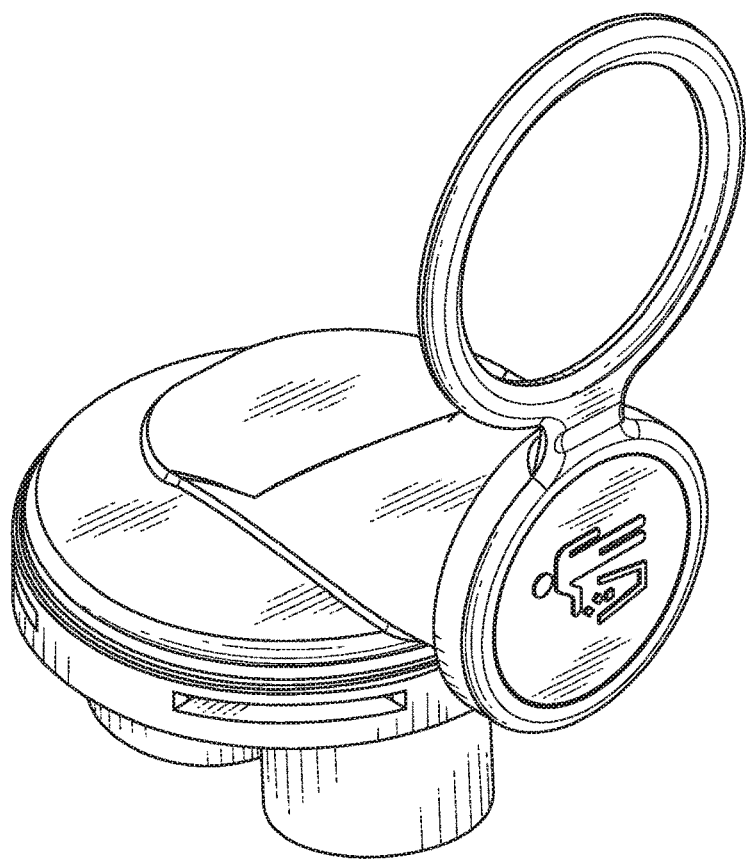
Figure 27D:
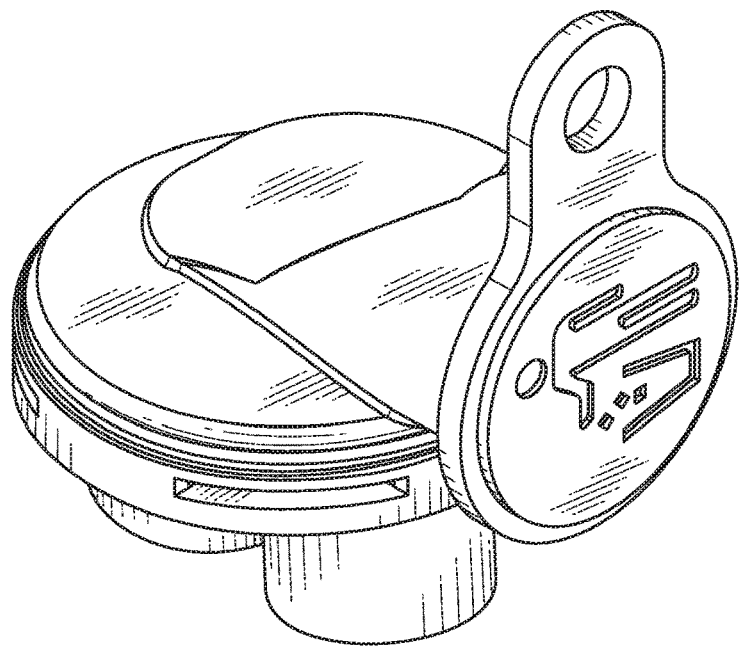
Figure 27E:
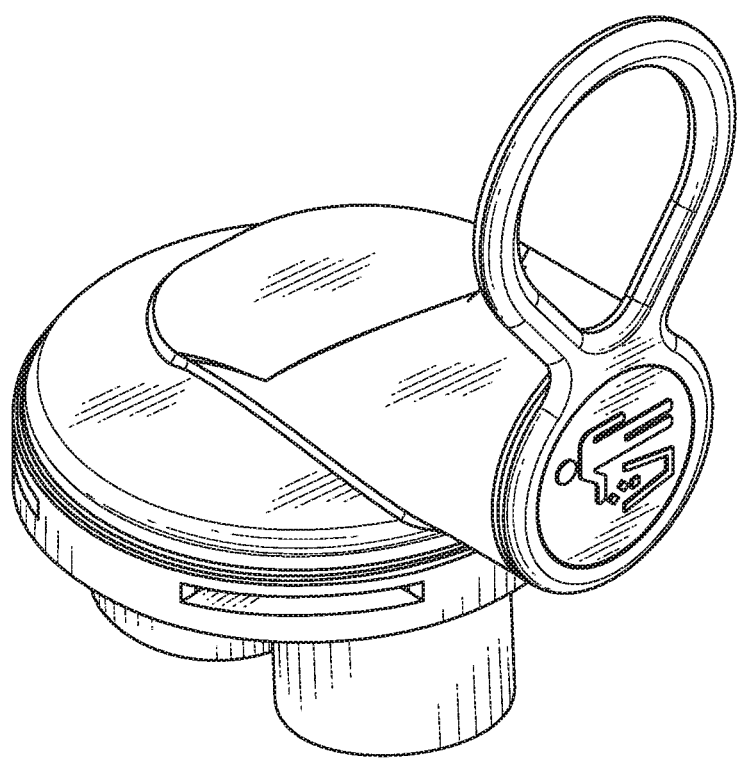

The hook 506 and flange 504 can have varying dimensions. For example, the embodiment of FIGS. 24A and 24B has a larger diameter hook 506 and larger diameter flange 504 than the embodiment of FIGS. 23A and 23B. If the end cap 500 of FIGS. 23A and 23B is connected to the Y-piece 124 having an inner shell 124a and an outer shell 124b, the flange 504 covers only the inner shell 124a as shown in FIG. 23B. The flange 504 of the end cap 500 of FIGS. 24A and 24B covers both the inner shell 124a and the outer shell 124b as shown in FIG. 24B. FIGS. 25A and 26A illustrate additional embodiments of end caps 500, and FIGS. 25B and 26B illustrate the end caps of FIGS. 25A and 26A, respectively, coupled to the Y-piece 124. FIGS. 27A-27E illustrate the end caps of FIGS. 19, 23A, 24A, 25A, and 26A, respectively, coupled to an alternative version of the Y-piece 124. The Y-piece 124 of FIGS. 27A-27E can be used for an infant patient.

Example Operational Modes and Features

Figure 30A:
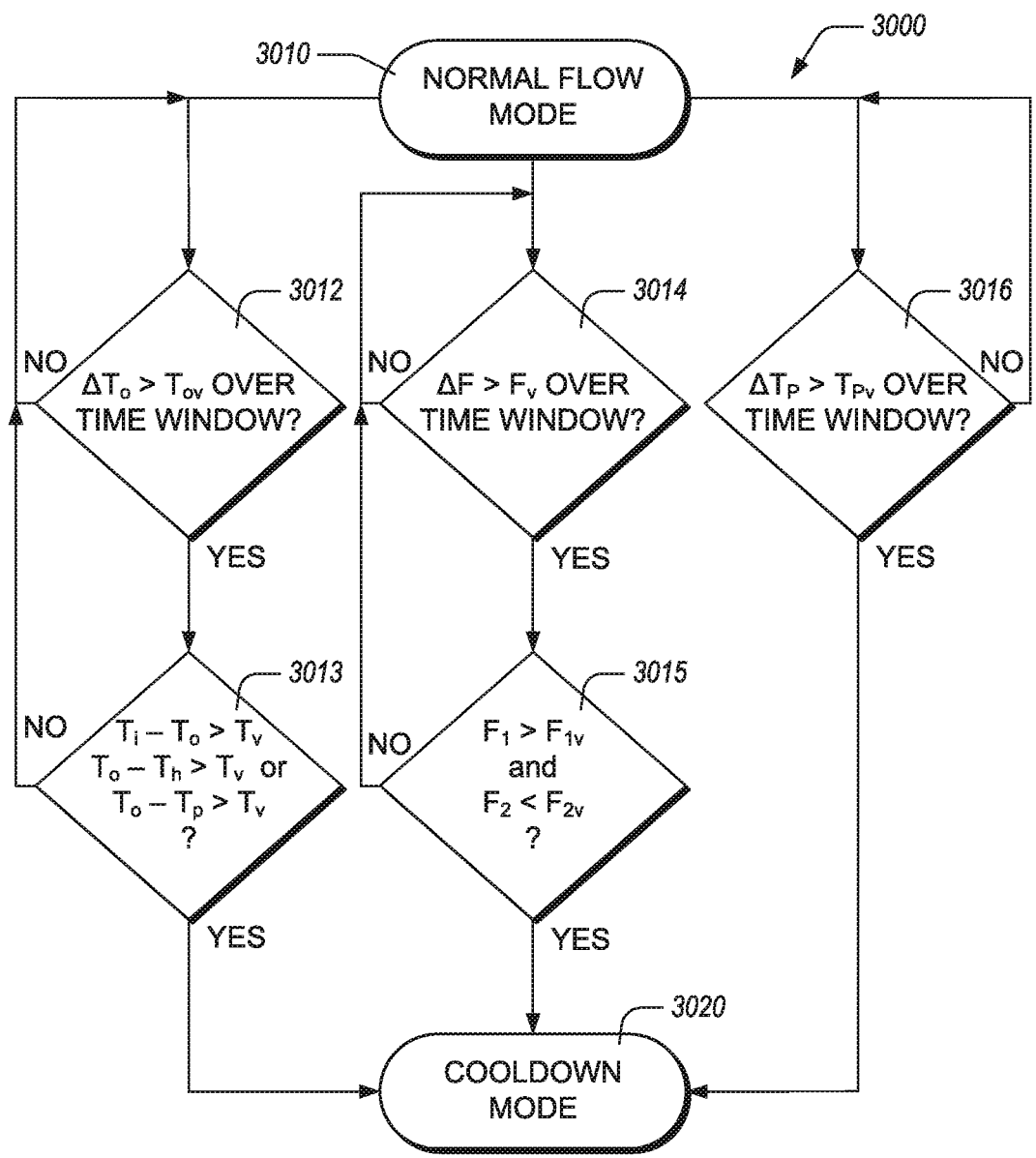
FIGS. 30A-30C illustrate flow charts of an example operational method of a humidification system wherein the method is configured to detect when a breathing circuit is connected improperly.
Figure 30B:
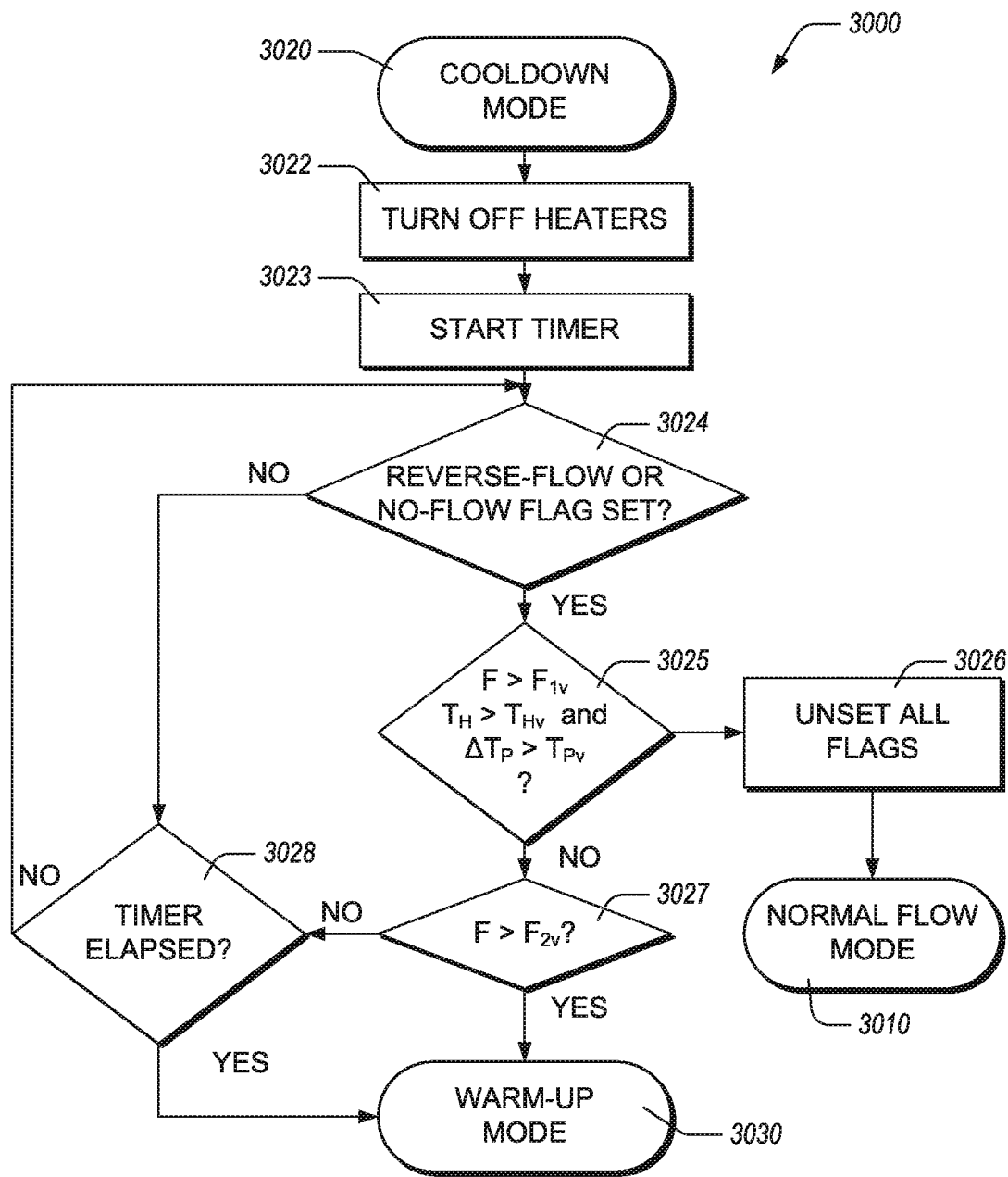
Figure 30C:
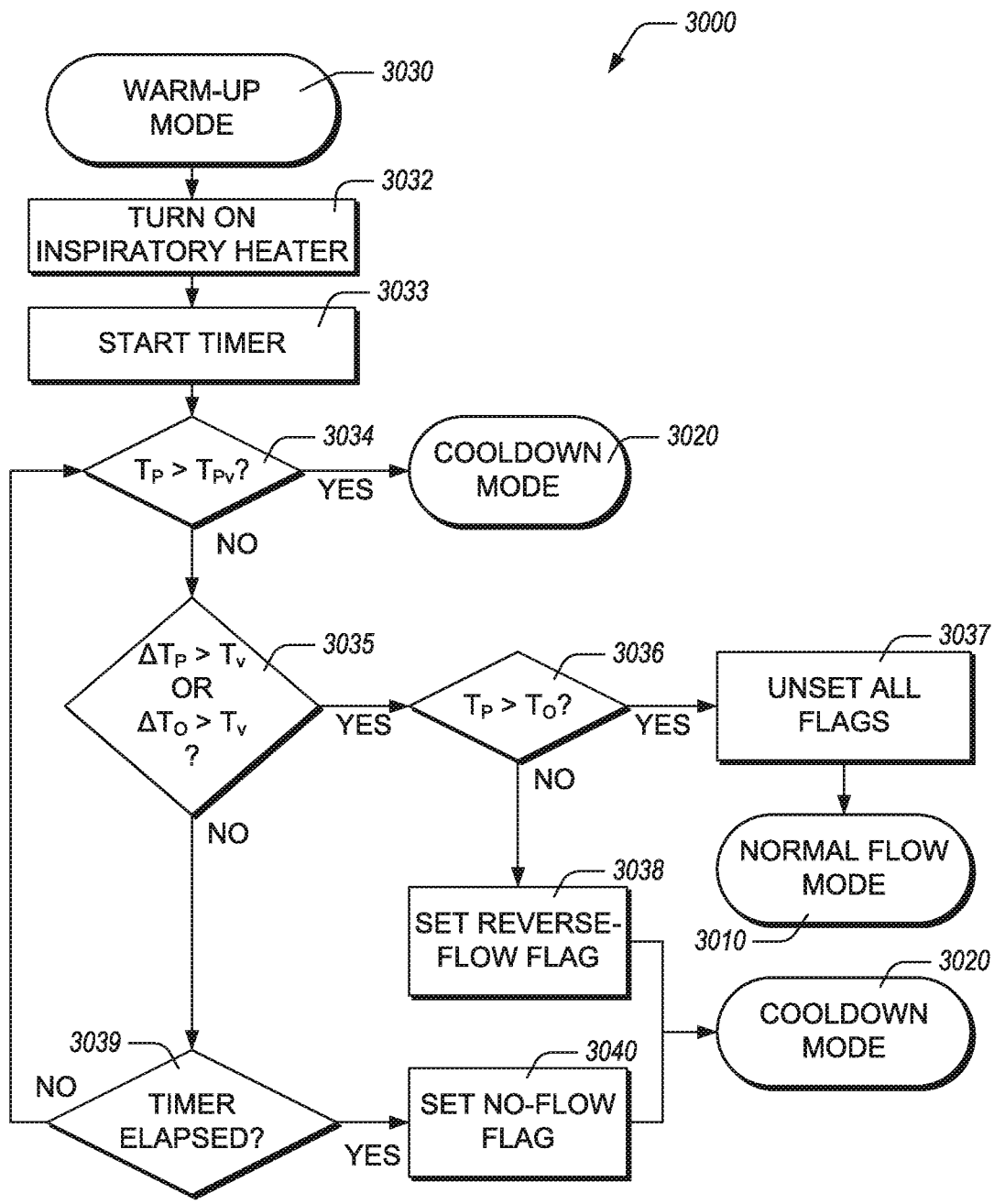

FIGS. 30A-C illustrate flow charts of an example operational method 3000 of a humidification system wherein the method is configured to detect when a breathing circuit is connected improperly, such as when the breathing circuit is connected and provides a flow the reverse of a normal flow. In some embodiments, the operational method can also be configured to detect when there is no flow due to a portion of the breathing circuit being disconnected. A reverse flow can be when the flow of air is reverse to the normal flow of air under normal operating circumstances, such as when an expiratory conduit is coupled to an output of a blower or ventilator, a dry line is coupled from an inlet port of a chamber to an inlet of the blower or ventilator, and an inspiratory conduit is coupled from a patient interface to an outlet port of the chamber. For ease of description, the steps of the method 3000 will be described as being performed by the humidification system, such as the humidification system 100 described herein. It is to be understood, however, that one or more hardware and/or software components of the humidification system can be configured to perform any portion or combination of the steps of the method 3000.

The humidification system can be configured to operate in a first mode 3010, which can be referred to as a normal flow mode, a flow chart of which is illustrated in FIG. 30A. During the normal flow mode, the humidification system can monitor operating conditions in a passive manner to detect potential flow problems and to test for unusual flow conditions, or flow anomalies. If such conditions are detected, the humidification system can be configured to change operating modes to attempt to determine the cause of the problems and/or anomalies. The humidification system can monitor conditions described herein with reference to blocks 3012, 3014, and 3016 asynchronously, independently, and/or concurrently.

In block 3012, the humidification system monitors parameters of the flow of gases to detect whether there is a rise in temperature at the chamber outlet port. If the temperature at the chamber outlet port increases by more than a designated temperature over a period of time, then the humidification system can be configured to signal this condition to other components of the system. In some embodiments, the designated temperature can be, for example and without limitation, at least about 2° C., at least about 2.5° C., or at least about 3° C. and the period of time can be at least about 30 sec., at least about 1 min., or at least about 2 min. One purpose of testing this condition is to see whether energy is being carried away from the chamber. When the flow of gas is not operating regularly, the temperature at the chamber outlet port may increase as energy is not being carried away from the chamber as expected.

If the condition in block 3012 is satisfied, the humidification system further tests for heating anomalies in the system in block 3013. For example, the humidification system can test whether the inlet port temperature, Ti, exceeds the outlet port temperature, To, by a designated temperature value, Tv. Similarly, the humidification system can test whether the outlet port temperature, To, exceeds the heater plate temperature, Tp, by a designated temperature value, Tv. Likewise, the humidification system can test whether the outlet port temperature, To, exceeds the patient-end temperature, Tp, by a designated temperature value, Tv. In certain implementations, the designated temperature value, Tv, can be the same for each of the above tests or it can be different for each one. In some implementations, the designated temperature can be, for example and without limitation, at least about 1° C., at least about 1.5° C., at least about 2° C., or at least about 2.5° C. Each of the above temperature anomalies can indicate that the flow of gases is not behaving as expected. If the condition in block 3013 is satisfied, the humidification system can enter a second mode 3020, which can be referred to as a cool down mode.

In block 3014, the humidification system can be configured to monitor parameters of the flow of gases to detect whether there is a decrease in flow over a time period. If the flow of gases decreases suddenly, then it can indicate that a conduit has been disconnected or connected incorrectly. As a first test, the humidification system can monitor the flow of gases to detect a relatively large decrease in flow over a relatively short period of time (for example, the change in flow is greater than a designated flow value, Fv). In some embodiments, the humidification system can monitor the flow of gases by taking instantaneous measurements of flow rate. In some embodiments, the humidification system can monitor the flow of gases by taking filtered measurements of flow rate, such as time-averaged measurements. For example and without limitation, the humidification system can signal that there is a sudden decrease in flow when the flow decreases by at least about 60%, by at least about 50%, or by at least about 40%. Similarly, the humidification system can signal that there is a sudden decrease in flow when the flow decreases by a specified amount over a designated time period that is less than or equal to about 30 sec., less than or equal to about 20 sec., less than or equal to about 10 sec., less than or equal to about 5 sec., or less than or equal to about 3 sec.

If the condition in block 3014 is satisfied, the humidification system can test whether the flow has dropped from a flow value exceeding a first flow value, F1, to a flow value below a second flow value, F2, in block 3015. The first and second flow values can be selected to ensure that flow values are being tested that are not subject to relatively high variability under normal operating conditions. For example, at low flow rates (for example, less than about 1 Lpm), the flow rate can regularly fluctuate by about 50% over relatively short periods of time. In some implementations, the first flow value, F1, can be at least about 5 Lpm, at least about 6 Lpm, at least about 7 Lpm, or at least about 8 Lpm. In certain implementations, the second flow value, F2, can be less than or equal to about 4 Lpm, less than or equal to about 3.5 Lpm, less than or equal to about 3 Lpm, or less than or equal to about 2.5 Lpm. In some embodiments, the humidification system can be configured to ignore the low flow signal when the change in flow has been requested by a user or when the system expects the flow to decrease. The above flow change anomaly can indicate that the flow of gases is not behaving as expected. If the condition in block 3015 is satisfied, the humidification system can enter the second mode 3020.

In block 3016, the humidification system monitors parameters of the flow of gases to detect whether there is a drop in temperature at the patient end of the inspiratory conduit. If the temperature at the patient end decreases by more than a designated temperature over a period of time, then the humidification system can be configured to signal this condition to other components of the system. In some embodiments, the designated temperature can be, for example and without limitation, at least about 0.5° C., at least about 1° C., or at least about 1° C. and the period of time can be at least about 30 sec., at least about 1 min., or at least about 2 min. One purpose of testing this condition is to see whether energy is being carried to the patient end. When the flow of gas is not operating regularly, the temperature at the patient end may decrease as energy is not being carried to the patient end as expected. The above temperature change anomaly can indicate that the flow of gases is not behaving as expected. If the condition in block 3016 is satisfied, the humidification system can enter the second mode 3020.

When entering the second mode 3020 from the first mode 3010, it may be that a reverse-flow flag or a no-flow flag has not been set and the humidification system will operate in the second mode 3020 for a full duration of a timer set in that mode. This may be desirable to stabilize the temperature of the gases throughout the humidification system and associated circuits, to improve the accuracy of subsequent temperature measurements.

FIG. 30B illustrates a flow chart of the second mode 3020, which may be referred to as a cooldown mode or a heater-off testing mode. While operating in the second mode 3020, the humidification system can deactivate one or more or all of the heaters to allow the system to cool down and to stabilize the temperature of the gases. The humidification system can be configured to monitor parameters of the flow of gases during the second mode 3020 to determine when and/or whether to exit the second mode 3020 and/or which mode of operation to perform upon exiting the second mode.

In block 3022, the humidification system is configured to turn off the heaters in the system (for example, heater plate, heater wires, etc.). In block 3023, the humidification system is configured to start a timer that determines a maximum amount of time to remain in the second mode of operation 3020 before exiting to another operation mode. The timer can be set to run for at least about 1 min., at least about 1.5 min., at least about 2 min., or at least about 4 min. In block 3024, the humidification system tests whether a reverse-flow flag or a no-flow flag has been set. The respective flags may be set in the third mode 3030, described herein. If no flags have been set, the humidification system cools down for a prescribed amount of time before entering the third mode 3030. This may be useful when temperatures have increased to levels that have been deemed undesirable, as described herein, such as when the gas temperature is high enough that it may injure a user.

If at least one flag is set as discovered in block 3024, the humidification system in block 3025 tests whether the flow exceeds a first designated flow value, Flv, the heater plate temperature, Tp, exceeds a designated temperature, Tpv, and the patient-end temperature, Te, increases more than a designated patient-end temperature change, Tev. If each of these conditions is satisfied, the humidification system can unset all flags in block 3026 and enter the first mode 3010, or normal flow mode. These conditions can be configured to indicate that flow has likely returned to a normal flow mode so that the full length of the timer set in block 3023 need not run before resuming normal operations. This can speed up a return to normal operating conditions, reducing interruption to therapy delivery. The first designated flow value, Flv, can be, for example and without limitation, at least about 1.5 Lpm, at least about 2 Lpm, at least about 2.5 Lpm, or at least about 3 Lpm. The designated temperature, Tpv, can be, for example and without limitation, at least about 43° C., at least about 45° C., at least about 50° C., or at least about 53° C. The designated patient-end temperature change, Tev, can be, for example and without limitation, at least about 1° C., at least about 1.5° C., at least about 2° C., or at least about 2.5° C. The designated patient-end temperature change can be measured as a change in patient-end temperature over a period of time where an initial patient-end temperature can be the measured temperature at the start of the second mode 3020, at the end of the previous operating mode, or the temperature taken at the start of a sliding time window (for example, the temperature 20 seconds ago, 30 seconds ago, 40 seconds ago, etc.).

If the conditions in block 3025 are not satisfied, the humidification system can be configured to monitor the flow in block 3027 to detect whether the flow exceeds a second designated flow value, F2v. When the flow exceeds the second designated flow value, this can indicate that the conduit has been connected properly but that further testing may be preferable to ensure proper connection of the conduit. In certain implementations, the second designated flow value, F2v, can be, for example and without limitation, at least about 2 Lpm, at least about 3 Lpm, at least about 4 Lpm, or at least about 5 Lpm. If this condition is satisfied, the humidification system can proceed to the third mode 3030, or warm-up mode, without requiring the timer set in block 3023 to expire. This can speed up the process of determining whether the breathing circuit is connected properly and reduce interruption to normal therapy delivery.

If the condition in block 3027 is not satisfied, the humidification system can be configured to check whether the timer set in block 3023 has elapsed. If it has, the humidification system can enter the third mode 3030, or warm-up mode. If it has not, the humidification system can return to block 3024 to test whether the flow flags are set.

FIG. 30C illustrates a flow chart of the third mode 3030, which may be referred to as a warm-up mode or a heater-on testing mode. In block 3032, the humidification system turns on one or more heaters in the inspiratory conduit. In some embodiments, the heater wire in the inspiratory conduit can be run at about 100% duty cycle for the duration of the third mode 3030. In some embodiments, the heater wire in the inspiratory conduit can be run using a control function calculated to produce a predetermined power output level. In some embodiments, the heater wire in the inspiratory conduit can be run using a control function that is varied based on the measured gases flow rate. In block 3033, the humidification system is configured to start a timer that determines a maximum amount of time to remain in the third mode of operation 3030 before exiting to another operation mode.

In block 3034, the humidification system tests whether the temperature of the gas at the patient end exceeds a designated temperature, Tev. This can be done to increase patient safety and to reduce a likelihood of burning or injuring a user by providing gases that are too hot. If the patient-end temperature exceeds the designated temperature, Tev, the humidification system can re-enter the second mode 3020, or the cooldown mode, to allow the temperature of the gases to decrease to acceptable and/or safe levels. In some implementations, the designated temperature, Tev, can be, for example and without limitation, at least about 42° C., at least about 42.5° C., at least about 43° C., or at least about 45° C. This condition can be monitored frequently and/or continuously by the humidification system to allow the system to exit the third mode if the temperature exceeds the designated temperature. When this condition is triggered, no flags may be set such that the humidification system will operate in the second mode 3020 for the full duration of the timer set in that mode.

If the condition is not satisfied in block 3034, the humidification system tests in block 3035 whether the patient-end temperature or the chamber outlet temperature has increased by a designated temperature increase value, Tiv, over a time period. Where there is an increase, this can indicate that the conduits are connected and that there is a flow of gases along the inspiratory conduit. In certain implementations, the designated temperature increase value, Tiv, can be, for example and without limitation, at least about 1° C., at least about 1.5° C., at least about 2° C., or at least about 2.5° C. In some embodiments, the designated temperature increase value applied to the patient-end temperature may be different from the designated temperature increase value applied to the chamber outlet temperature. The designated temperature increase value can be measured as a change in temperature over a period of time where an initial temperature can be the measured temperature at the start of the third mode 3030, at the end of the previous operating mode, or the temperature taken at the start of a sliding time window (for example, the temperature 20 seconds ago, 30 seconds ago, 40 seconds ago, etc.).

If the condition is satisfied in block 3035, the humidification system in block 3036 determines whether the patient-end temperature exceeds the chamber outlet temperature. In some embodiments, the humidification system can determine whether the patient-end temperature exceeds the chamber outlet temperature by a designated temperature difference. For example, the designated temperature difference can be, for example and without limitation, at least about 0° C., at least about 1° C., at least about 2° C., or at least about 2.5° C. When this is the case, it can indicate that the flow of gases is as expected and the humidification system can unset all flags in block 3037 and resume normal therapy by returning to the first mode 3010. If the condition is not satisfied, it can indicate that the flow of gases is reverse to what is expected because temperature is increasing from the patient to the chamber outlet, indicating that the flow of gases is flowing from the patient to the chamber outlet. If this is the case, the humidification system can set the reverse-flow flag in block 3038 and return to the second mode 3020, or the cool down mode. The humidification system can also cause a warning, alarm, notification, or the like to occur to signal to a user that the conduits are potentially connected incorrectly.

If the condition in block 3035 is not satisfied, the humidification system can determine whether the time set in block 3033 has expired. If it has, the humidification system can set the no-flow flag in block 30340 and return to the second mode 3020, or the cool down mode. The humidification system can also cause a warning, alarm, notification, or the like to occur to signal to a user that the conduits are potentially disconnected. The conditions in blocks 3034 and 3035 may not be satisfied when a conduit is disconnected because there will be no significant or substantial increase in temperature at the chamber outlet or the patient-end as gas is not flowing into the chamber to be heated therein.

Figure 31:
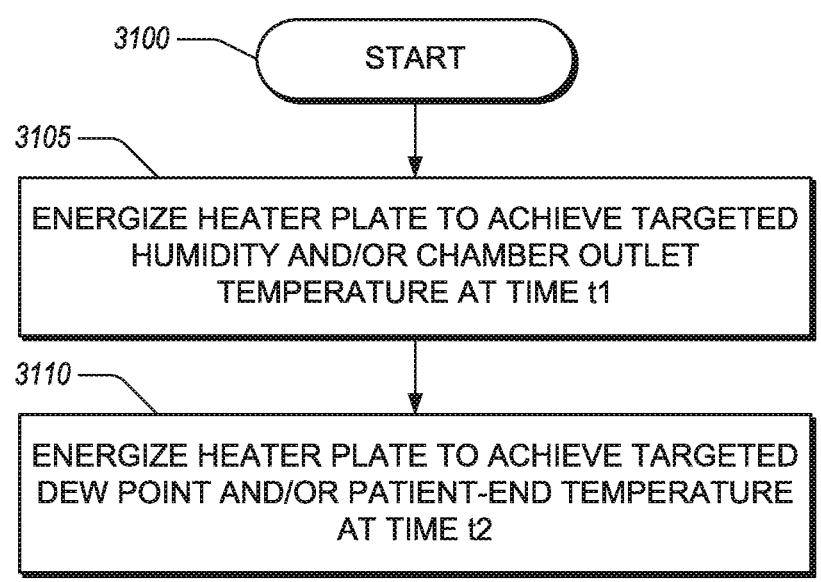
FIG. 31 illustrates a flow chart of an example method for providing a humidified gas to a patient or user, wherein the startup procedure is configured to gradually increase the temperature of the gas.

FIG. 31 illustrates a flow chart of an example method 3100 for providing a humidified gas to a user, wherein the startup procedure is configured to gradually increase the temperature of the gas. This can increase patient comfort and compliance as it may be uncomfortable for a user to receive gas that is heated relatively quickly. For ease of description, the steps of the method 3100 will be described as being performed by the humidification system, such as the humidification system 100 described herein. It is to be understood, however, that one or more hardware and/or software components of the humidification system can be configured to perform any portion or combination of the steps of the method 3100.

In block 3105, the humidification system energizes the heater plate to achieve a targeted dew point of flowing gases at a first targeted time. The humidification system can monitor a temperature of the gas at the chamber outlet and/or a temperature of the gas at the patient end and/or a temperature of the heater plate and/or an amount of power provided to the heater plate in order to calculate an estimate of the dew point of the gas. In certain implementations, the humidification system measures ambient temperature, gas inlet temperature, or the like to determine the humidity of the gas. In some embodiments, the humidification system is configured to achieve the targeted humidity after a period of at least about 5 min. and/or less than or equal to about 40 min., at least about 10 min. and/or less than or equal to about 30 min., or at least about 12 min. and/or less than or equal to about 20 min. The humidification system can use a targeted chamber outlet set point that changes over time to achieve the targeted humidity. The targeted humidity can be at least about 0.5 mg/L, at least about 1 mg/L, or at least about 2 mg/L. In some embodiments, the targeted chamber outlet temperature set point after the first targeted time can be at least about 24° C. and/or less than or equal to about 35° C., at least about 25° C. and/or less than or equal to about 28° C., or at least about 25.5° C. and/or less than or equal to about 26.5° C. The increase in temperature can be configured to be relatively slow so as to increase patient comfort and to achieve a targeted humidity during this first phase.

In block 3110, the humidification system energizes the heater plate using the patient-end temperature as a set point to achieve a therapeutic gas humidity and/or temperature. The humidification system can be configured to change the targeted set point as a function of time to achieve a gentle slope of temperature increase and to achieve the targeted therapeutic gas parameters after a second period of time or at the end of a specified, targeted, or desired duration after startup. For example, the targeted total amount of time to achieve the therapeutic gas parameters can be have a particular value, and the durations of the second targeted time and the first targeted time can be configured to total the targeted total amount of time. In some embodiments, the humidification system is configured to achieve the targeted therapeutic gas parameters after a period of at least about 30 min. and/or less than or equal to about 1.5 hrs, at least about 45 min. and/or less than or equal to about 1.25 hrs, or at least about 55 min. and/or less than or equal to about 65 min. In some embodiments, where the total targeted time is about an hour, the first targeted time can be 15 min. and the second targeted time can be 45 min., the first targeted time can be 30 min. and the second targeted time can be 30 min., or the first targeted time can be 10 min. and the second targeted time can be 50 min. The total targeted time can be at least about 30 min. and/or less than or equal to about 2 hrs, at least about 45 min. and/or less than or equal to about 1.5 hrs, at least about 55 min. and/or less than or equal to about 65 min. The increase in temperature can be configured to be relatively slow so as to increase patient comfort and to achieve a therapeutic humidity and temperature during this second phase. In some embodiments, the targeted temperature of the gas (for example, the patient-end set point) can be about 37° C. for an invasive mode or an Optiflow™ mode and about 31° C. for a non-invasive mode.

In some embodiments, the humidification system can be configured to adjust a chamber outlet set point based at least in part on an inlet port temperature. As the ambient temperature changes, the efficiency at which humidity can be passed to a gas changes. To accommodate for this relationship, the humidification chamber can be configured to adjust a chamber outlet set point by adding a chamber outlet set point offset to a targeted chamber outlet set point. By compensating for the inlet gas temperature, more consistent gas humidity can be achieved. The humidification system can use the chamber inlet temperature reading to determine a chamber outlet set point offset and adjust the chamber outlet set point by the determined offset. This may be advantageous where the humidification system is targeting a dew point of the gas rather than merely a gas temperature. The change in the chamber outlet set point can affect the amount of power delivered to the heater plate to achieve the desired gas dew point while accommodating for the gas temperature at the chamber inlet. In some embodiments, the functional relationship between the chamber outlet set point offset and the inlet port temperature can be determined empirically for a particular gas and breathing circuit configuration. In some embodiments, this adjustment can limit overshoot of an estimated dew point. In some implementations, this adjustment can be independent of flow rate.

The humidification system can be configured to update a user interface and control algorithm based at least in part on an identified breathing circuit. The breathing circuit can include a component that provides or results in a signal read by the humidification system. The value or characteristics of the signal can indicate the type of breathing circuit connected (for example, adult circuit, neonatal circuit, etc.) and the operation of the humidification system can be adjusted accordingly. For example, based on an ID resistor value in the circuit, the humidification system can decide whether to use a second heater driver for an expiratory conduit or for a second zone in an inspiratory conduit. The humidification system can be configured to limit operational or functional capabilities based on the breathing circuit attached. For example, in an infant mode, the humidification system can limit the available operating therapies whereas in an adult mode, the humidification system can provide more operating therapies. In some embodiments, a cartridge can be configured to be used with a number of different modes or the cartridge can be particular to a mode. Where the cartridge is configured for use with a number of modes, plugging in a particular breathing circuit can cause the cartridge to operate based on the breathing circuit. This can allow for the humidification system to be a plug and play system by allowing a number of different breathing circuits to be used and plugged in and providing an appropriate operating environment and therapies to the user based at least in part on the breathing circuit.

In some embodiments, the humidification system includes a safety circuit configured to reduce or prevent mal-functioning associated with providing power to the multiple heaters in multiple zones when operating in an infant mode or dual-zone heating mode. The humidification system can be configured to operate where the inspiratory conduit passes through multiple zones, proving a plurality of heating zones within the inspiratory tube. To operate the plurality of heaters in the heating zones, a power supply can be used to provide alternating current, or positively and negatively biased electrical voltages in turn. These currents and/or biased voltages can be controlled by switches in the humidification system. Closing both switches to allow both directions of current or both positively and negatively biased voltages at the same time can damage the system. The humidification system can include a latch that opens a main relay when the system (for example, through a software or hardware malfunction) activates incompatible heater drivers (for example, both sets of switches are activated where there are two zones).

In some embodiments, the humidification system is configured to maintain a short-term storage of running state that is configured to survive a momentary power outage or fault. For example, for a power outage of less than about 1 min., less than about 30 sec., or less than about 15 sec., the running state can be stored so that when operation resumes, the therapy that was running at the time of the power outage of fault resumes.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A humidification system for humidifying respiratory gases provided to a patient, the humidification system comprising:
   a heater plate;
   a flat heating element configured to heat the heater plate, the flat heating element comprising a non-conductive core and a filament wound around the non-conductive core, the filament having an at least partially flat cross-sectional shape with a first flat surface facing towards the non-conductive core and a second flat surface facing away from the non-conductive core, the flat heating element comprising a single layer of the filament on each side of the non-conductive core;
   a base supporting the heater plate and configured to receive a portion of a removable chamber that is configured to hold a liquid; and
   one or more springs applying an upward force to the heater plate and urging the heater plate into contact with the removable chamber
   wherein the heater plate comprises a first surface at a periphery of the heater plate, a second surface at least partially surrounded by the first surface, and a recess defined within the second surface that is recessed relative to the first surface and the second surface, the recess configured to receive the heating element therein.

2. The humidification system of claim 1, wherein the upward force is about 35 Newtons (N).

3. The humidification system of claim 1, comprising a spring assembly comprising:
   a first spring assembly platform supporting a base of the spring; and
   a screw secured to and extending downward from a bottom of the heater plate, wherein a body of the screw passes through an opening of the first spring assembly platform and a head of the screw is below the first spring assembly platform, wherein the opening of the first spring assembly platform is large enough to allow the screw body to pass through the opening without resistance but not large enough to allow the screw head to pass through the opening.

4. The humidification system of claim 3, comprising a spring preloading assembly comprising a second spring assembly platform located below the first spring assembly platform, the second spring assembly platform including an opening that is large enough to allow the screw body to pass through the opening without resistance but not large enough to allow the screw head to pass through the opening.

5. The humidification system of claim 1, wherein the one or more springs are preloaded so that when the chamber is inserted into the base, the heater plate is required to travel 1-3 mm without diminishing the upward force exerted by the springs on the heater plate.

6. The humidification system of claim 1, wherein the flat heating element comprises a first end and a second end electrically connected to a respective one of a first connector and a second connector located on opposite sides of the filament wound around the non-conductive core, the system further comprising a first wire and a second wire electrically connected to a respective one of the first connector and the second connector; a first insulatory piece providing electrical insulation for the first end, the first connector, and the first wire; and a second insulatory piece providing electrical insulation for the second end, the second connector, and the second wire.

7. The humidification system of claim 6, further comprising an insulation layer, wherein at least one of the first insulatory piece or the second insulatory piece is clamped to the insulation layer.

8. The humidification system of claim 6, wherein the first insulatory piece comprises a first insulatory piece associated with the first end, the first connector, and the first wire and a second insulatory piece associated with the second end, the second connector, and the second wire.

9. The humidification system of claim 8, wherein each of the first insulatory piece and the second insulatory piece comprise an annular flange.

10. The humidification system of claim 1, comprising at least two insulation layers between the filament and the heater plate.

11. The humidification system of claim 1, wherein an upper wall defines a continuous top surface of the base that only partially surrounds a perimeter of the heater plate.

12. The humidification system of claim 11, wherein the base further includes a rim edge extending downward from one end of the upper wall, the one end being away from a side wall of the base, and
wherein, when the removable chamber is disposed in the base, the heater plate is configured to press upward on the removable chamber while the rim edge is configured to resist an upward movement of a lip of the removable chamber, the lip protruding beyond a body of the removable chamber.

13. The humidification system of claim 11, wherein the upper wall is configured to substantially enclose at least a portion of the heater plate.

14. The humidification system of claim 1, wherein the one or more springs are preloaded so that when the chamber is inserted into the base, the heater plate is allowed to travel downward without diminishing the upward force exerted by the springs on the heater plate.

15. The humidification system of claim 1, wherein the base comprises a side wall that at least partially surrounds the heater plate and an upper wall that extends inwardly from the side wall towards the heater plate to create a space beneath the upper wall configured to receive a portion of a removable chamber that is configured to hold a liquid.

16. A heating assembly in a humidification system, the heating assembly comprising:
a heating plate;
a non-conductive core;
a base supporting the heating plate and configured to receive a portion of a removable chamber that is configured to hold a liquid; and
an at least partially flat filament configured to heat the heating plate, the at least partially flat filament wound around the non-conductive core, the filament having a first flat surface facing towards the non-conductive core and a second flat surface facing away from the non-conductive core;
wherein a combination of the at least partially flat filament and the non-conductive core cooperate to form a flat heating element that is configured to heat the heating plate in use, the flat heating element comprising a single layer of the filament on each side of the non-conductive core,
wherein the heating plate comprises a first surface at a periphery of the heating plate, a second surface at least partially surrounded by the first surface, and a recess defined within the second surface that is recessed relative to the first surface and the second surface, the recess configured to receive the heating element therein.

17. The heating assembly of claim 16, wherein the at least partially flat filament provides higher heating power at lower temperatures than a round filament of equivalent cross-sectional area.

18. The heating assembly of claim 16, wherein the heating assembly is configured to heat liquid sufficient to humidify a gas flow of 80 liters per minute (Lpm) at 37 degrees Celsius.

19. The heating assembly of claim 16, comprising at least one insulation layer between the at least partially flat filament and the heating plate.

20. The heating assembly of claim 16, comprising a back plate, a first insulation layer between the at least partially flat filament and the back plate, and a second insulation layer between the at least partially flat filament and the heating plate.

21. The heating assembly of claim 20, comprising an insulator piece positioned on the first insulation layer, the insulator piece configured to insulate a wire connecting a power source to the heating assembly.

22. The heating assembly of claim 21, the insulator piece comprising a flange clamped to the first insulation layer.

23. The heating assembly of claim 21, the insulator piece comprising a ceramic material.

24. The heating assembly of claim 21, the insulator piece comprising a T-shape.

25. The heating assembly of claim 21, wherein the insulator piece fills at least one opening on the back plate.

26. The heating assembly of claim 16, comprising an insulation layer surrounding the at least partially flat filament.

27. The heating assembly of claim 26, wherein the insulation layer forms part of at least a 0.4 mm layer of insulation.

28. The heating assembly of claim 26, wherein the insulation layer comprises a pair of insulation layers, each layer being 0.2 mm thick.

29. The heating assembly of claim 16, wherein a spacing between each winding of the at least partially flat filament is about 0.3 mm.

* * * * *